(12) United States Patent
Cheroutre et al.

(10) Patent No.: US 11,951,128 B2
(45) Date of Patent: Apr. 9, 2024

(54) COMPOSITIONS AND METHODS FOR THE ISOLATION AND/OR GENERATION OF SPECIFIC CD4+ AND CD8+ T-CELL SUBSETS

(71) Applicant: LA JOLLA INSTITUTE FOR ALLERGY AND IMMUNOLOGY, La Jolla, CA (US)

(72) Inventors: Hilde Cheroutre, La Jolla, CA (US); Nicolas Thiault, La Jolla, CA (US); Alexandre Larange, La Jolla, CA (US); Hitoshi Iwaya, La Jolla, CA (US)

(73) Assignee: LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 560 days.

(21) Appl. No.: 16/635,015

(22) PCT Filed: Aug. 2, 2018

(86) PCT No.: PCT/US2018/045072
§ 371 (c)(1),
(2) Date: Jan. 29, 2020

(87) PCT Pub. No.: WO2019/028295
PCT Pub. Date: Feb. 7, 2019

(65) Prior Publication Data
US 2021/0128614 A1 May 6, 2021

Related U.S. Application Data

(60) Provisional application No. 62/540,501, filed on Aug. 2, 2017, provisional application No. 62/540,498, filed on Aug. 2, 2017.

(51) Int. Cl.
| | | |
|---|---|---|
| *A61K 35/17* | (2015.01) | |
| *A61K 31/203* | (2006.01) | |
| *A61P 35/00* | (2006.01) | |
| *C07K 14/495* | (2006.01) | |
| *C07K 14/54* | (2006.01) | |
| *C07K 14/705* | (2006.01) | |
| *C07K 14/73* | (2006.01) | |
| *C07K 16/28* | (2006.01) | |

(52) U.S. Cl.
CPC ............ *A61K 35/17* (2013.01); *A61K 31/203* (2013.01); *A61P 35/00* (2018.01); *C07K 14/495* (2013.01); *C07K 14/54* (2013.01); *C07K 14/70514* (2013.01); *C07K 14/70517* (2013.01); *C07K 16/2809* (2013.01); *C07K 16/2818* (2013.01)

(58) Field of Classification Search
CPC .... A61K 35/17; A61K 31/203; C12N 5/0636; C07K 14/495; C07K 14/54
See application file for complete search history.

(56) References Cited

U.S. PATENT DOCUMENTS

2012/0142109 A1\* 6/2012 Katayama ............ C12N 5/0636
435/325
2014/0294793 A1\* 10/2014 Littman ............... C12N 5/0637
435/375

OTHER PUBLICATIONS

Tsujimura et al. Positive Selection of gamma delta CTL by TL Antigen Expressed in the Thymus. Journal of Experimental Medicine 184.6 (1996):2175-2184 (Year: 1996).\*
Paul (Fundamental Immunology, 3rd Edition, Raven Press, New York, Chapter 8, pp. 292-295, 1993 (Year: 1993).\*
MacCallum et al. (Journal of Molecular Biology, 262:732-745, 1996 (Year: 1996).\*
Casset et al. (Biochemical and Biophysical Research Communications, 307:198-205, 2003 (Year: 2003).\*
Vajdos et al. (Journal of Molecular Biology, Jul. 5, 2002;320(2):415-28 (Year: 2002).\*
Sela-Culang et al. 2013 The structural basis of antibody-antigen recognition; Frontiers in Immunology 4(302):1-13 (Year: 2013).\*
International Search Report and the Written Opinion issued in PCT/US2018/045072 dated Nov. 8, 2018, 10 pages.
Tsujimura K. et al. "Thymus leukemia antigen (TL)-specific cytotoxic T lymphocytes recognize the α1/α2 domain of TL free from antigenic peptides". International immunology, 2003, 15(11): 1319-1326, abstract.
Tsujimura K. et al., "Positive selection of gamma delta CTL by TL antigen expressed in the thymus." Journal of Experimental Medicine, 1996, 184(6: 2175-2184, abstract, p. 2176-2180.
A. Larange, et al., "Retinoic Acid and Retinoic Acid Receptors as Pleiotropic Modulators of the Immune System," Annual Review of Immunology, 2016 vol. 34, pp. 369-394.
A. Leishman, et al., "T Cell Responses Modulated Through Interaction Between CD8αα and the Nonclassical MHC Class I Molecule, TL," Science, 2001, vol. 294, pp. 1936-1939. Downloaded from https://www.science.org on Oct. 3, 2023.
D. Mucida, et al., "TGFß and Retinoic Acid Intersect in Immune-Regulation," Cell Adhesion & Migration, vol. 1, Issue 3, 2007, pp. 142-144.
H. Cheroutre, et al., "Doubting the TCR Coreceptor Function of CD8αα," Immunity Review, 2008, pp. 149-159.

\* cited by examiner

*Primary Examiner* — Vanessa L. Ford
*Assistant Examiner* — Sandra Dillahunt
(74) *Attorney, Agent, or Firm* — Foley & Lardner LLP

(57) ABSTRACT

The present disclosure relates to particular subsets of CD4+ and CD8+ T-cells, methods of isolating and generating these cells, compositions comprising these cells, and methods of treatment of a tumor or cancer by administering these cells alone or in combination with each other and/or additional therapies.

8 Claims, 28 Drawing Sheets
Specification includes a Sequence Listing.

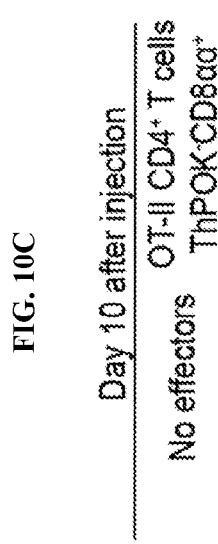
FIG. 10C
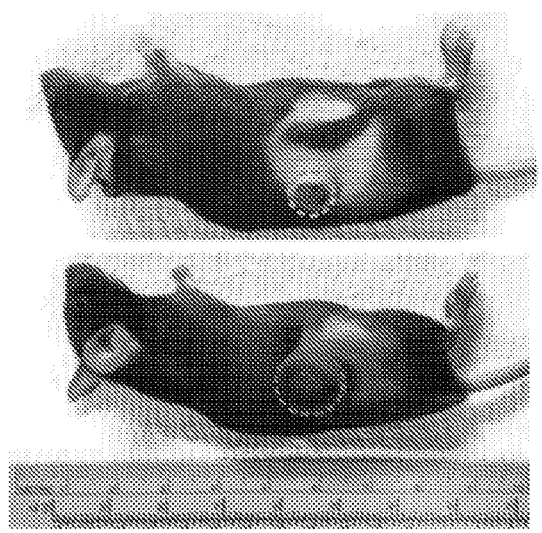
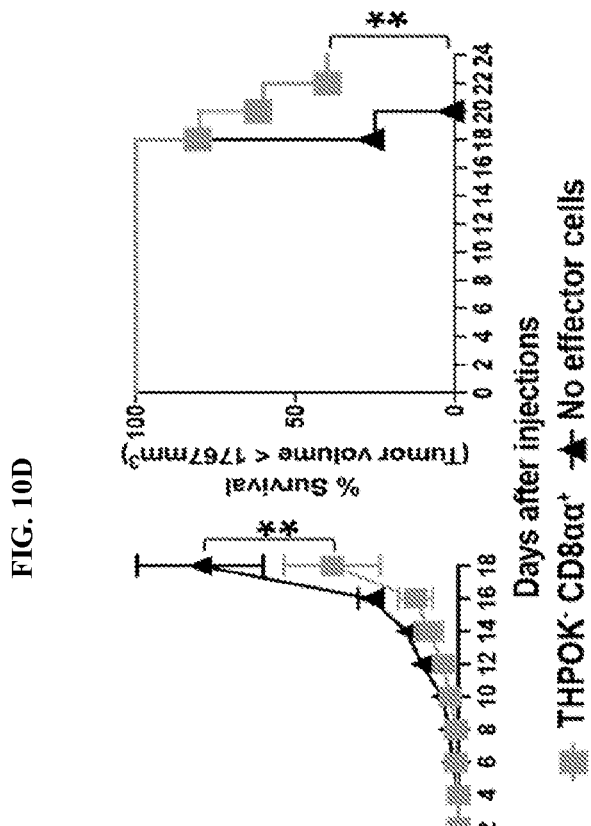
FIG. 10D

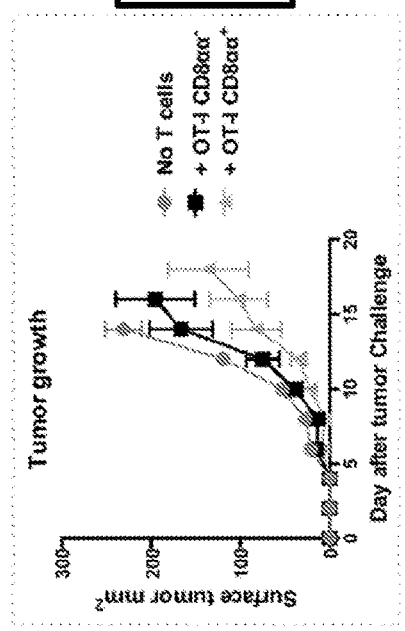
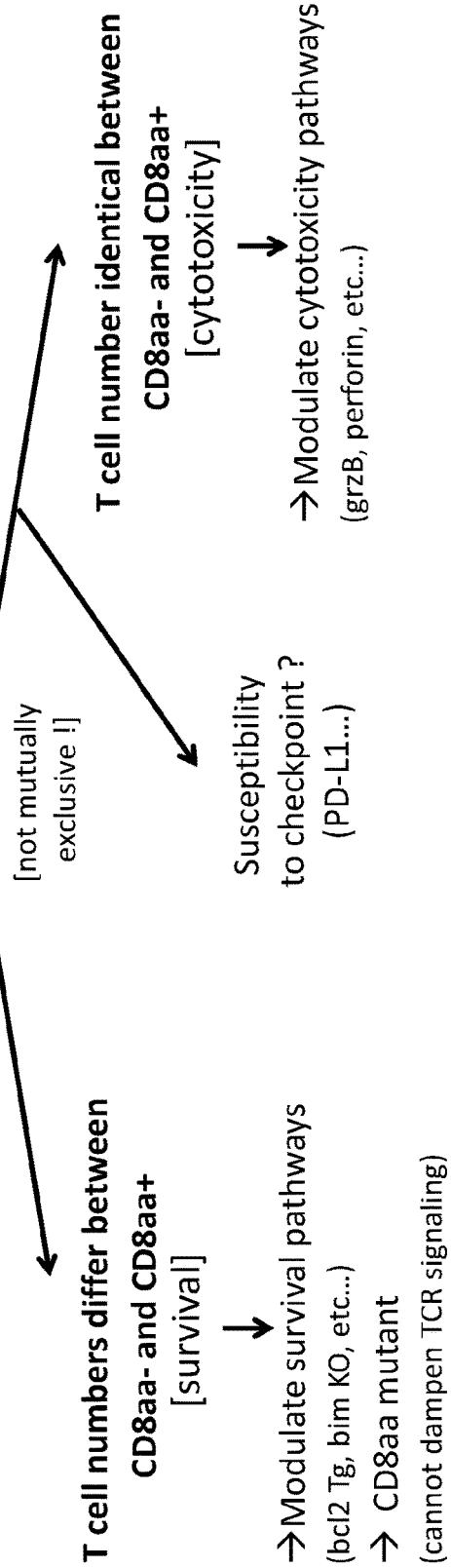
FIG. 24

COMPOSITIONS AND METHODS FOR THE ISOLATION AND/OR GENERATION OF SPECIFIC CD4+ AND CD8+ T-CELL SUBSETS

CROSS-REFERENCE TO RELATED PATENT APPLICATIONS

This application is a national stage application filed under 35 U.S.C. § 371 of PCT/US2018/045072, filed Aug. 2, 2018, which claims the benefit under 35 U.S.C. § 119(e) to U.S. Provisional Application No. 62/540,501, filed Aug. 2, 2017, and U.S. Provisional Application No. 62/540,498, filed Aug. 2, 2017, the contents of each of which are hereby incorporated by reference in its entirety.

STATEMENT REGARDING GOVERNMENT SUPPORT

This invention was made with government support under National Institutes of Health (NIH) Grant Nos. U01AI125957-0, R01AI106298-01A1, R01 AI050265-12. The government has certain rights in the invention.

SEQUENCE LISTING

The instant application contains a Sequence Listing which has been submitted electronically in ASCII format and is hereby incorporated by reference in its entirety. Said ASCII copy, created on Oct. 27, 2020, is named 116639-0222_SL.txt and is 17,392 bytes in size.

BACKGROUND

The immune system has evolved an intricate system of checks and balances to simultaneously protect the body from a diverse array of foreign pathogens while promoting tolerance that protects against attack of one's own cells or tissues.

Regulatory CD4+ T-cells (T-regs) are central mediators of immune tolerance playing an important role in preventing self-reactivity including inflammation. Impaired T-reg function can lead to the development and progression of autoimmune disorders. While T-regs are beneficial in preventing the development of autoimmunity, they are detrimental in preventing the immune system from fighting cancer. The mutations within cancerous cells that lead to uncontrolled cellular growth and dysfunction may be viewed as "self" and thus T-reg are geared to also suppress self-antigen-based anti-tumor immune responses. Many developments endeavor to turn off T-regs in the tumor environment, but targeting and silencing tumor-specific T-regs carry significant challenges and safety concerns.

SUMMARY

Central memory T-cells ($T_{CM}$) and resident effector memory T-cells ($T_{REM}$) are subsets of memory T-cells. $T_{CM}$ (KLRG1$^{Lo}$/IL-7R$^{hi}$ CD8ab) are central memory T-cells that are not functionally differentiated; they circulate through secondary lymphoid tissues. During a secondary challenge with the antigen to which they are directed, $T_{CM}$ have robust proliferation, transition into effectors, and migrate into non-lymphoid tissue. $T_{REM}$ are effector memory T-cells that are functionally differentiated. $T_{REM}$ can reside long term in non-lymphoid tissues, such as the mucosal epithelium. During a secondary challenge with the antigen to which they are directed, $T_{REM}$ display immediate effector function and enhanced efficiency.

The present disclosure relates to particular subsets of CD4+ and CD8+ T-cells, methods of isolating and generating these cells, compositions comprising these cells, and methods of treatment of a tumor or cancer by administering these cells alone or in combination with other therapies.

Aspects of this disclosure relate to a method of generating a population of tumor-specific CD4+ cytotoxic T-cells the method comprising, or alternatively consisting essentially of, or yet further consisting of, contacting a population of tumor-specific CD4+ T-cells with an effective amount of a combination comprising retinoic acid, TGF-β, and IL-27, thereby generating tumor-specific CD4+ cytotoxic T-cells. In some embodiments, the retinoic acid, the TGF-β, and the IL-27 of the combination are administered concurrently or sequentially. In some embodiments, the combination or one or more components thereof are administered to the population of tumor-specific CD4+ T-cells more than once, e.g., twice or thrice or more often as desired. In some embodiments, the combination comprising retinoic acid, TGF-β, and IL-27 comprises greater than about 5 ng/mL, less than about 25 ng/mL, or between about 5 ng/mL to about 25 ng/mL of IL-27; greater than, less than, or about 5 ng/mL or between about 2 ng/mL to about 10 ng/mL of TGF-β, and/or greater than about 100 nM, less than about 500 nM, or between about 100 nM to about 500 nM of retinoic acid, and concentrations within these ranges. All the indicated concentrations are the final concentrations in solution. In some embodiments, the aforementioned combination comprising retinoic acid, TGF-β, and IL-27 further comprises acetate and/or anti-IL-4.

The CD4+ cytotoxic T-cells prepared by the methods disclosed herein express CD4 on their surface and, are ThPOK$^-$ (downregulated) (conversely to naïve CD4+ T-cells which express THPOK). These CD4+ cytotoxic T-cells can also be characterized by CD8αα expression (having both CD8αα+ and CD8αα- subsets), downregulation of Gata3, and upregulation of Runx3 (in some subsets) and Tbet (in some subsets). CD4+ cytotoxic T-cells are also generally PD-1$^-$ (negative) and Lag3$^-$ (negative). The cells and/or populations of cells can be labeled (e.g., detectably labeled) for ease of purification or monitoring of the cells and/or populations.

Further aspects relate to a population of tumor-specific CD4+ cytotoxic T-cells prepared by the method disclosed herein. The CD4+ cytotoxic T-cells prepared by the methods disclosed herein express CD4 on their surface and, are ThPOK$^-$ (downregulated) (conversely to naïve CD4+ T-cells which express THPOK). These CD4+ cytoxic T-cells can also be characterized by CD8αα expression (having both CD8αα+ and CD8αα- subsets), downregulation of Gata3, and upregulation of Runx3 (in some subsets) and Tbet (in some subsets). CD4+ cytotoxic T-cells are also generally PD-1- and Lag3-; i.e. PD1 and Lag3 are not expressed by in vitro differentiated CD4 cytotoxic T-cells. Naïve CD4 T-cells do not express those molecules.

Still further aspects relate to a method of treating a tumor or cancer, and/or augmenting an immune response in a subject in need thereof, the method comprising, or alternatively consisting essentially of, or yet further consisting of, administering an effective amount of a population or composition as disclosed herein to the subject, thereby treating the tumor or the cancer or augmenting an immune response. In some embodiments, the method comprises, or alternatively consists essentially of, or yet further consists of, administering in sequence (a) an effective amount of (i) a population of immune cells comprising one or more of CD8+ T-cells (optionally CD8αα+ T-cells), double-negative T-cells (CD3+, CD4−, CD8−), and NK T-cells and/or (ii) IFNγ and (b) a population of tumor-specific CD4+ cytotoxic T-cells or a composition comprising said population.

Also provided is a kit for generating and expanding a population of tumor-specific CD4+ cytotoxic T-cells, optionally, comprising retinoic acid, TGF-β, and IL-27, and instructions for use. In some embodiments, the kit further comprises acetate and/or anti-IL-4.

Aspects of this disclosure relate to a method of isolating an anti-tumor CD8+ cytotoxic T-cell, the method comprising, or alternatively consisting essentially of, or yet further consisting of, contacting a population of cells suspected of comprising the anti-tumor cytotoxic CD8+ T-cell with a thymus leukemia ("TL") tetramer and isolating the T-cell bound to the TL tetramer. Also provided herein is an isolated anti-tumor CD8+ cytotoxic T-cell bound or coupled to TL tetramer. In a further aspect, the method further comprises or alternatively consists essentially of, or yet further consists of, isolating or separating the cell from the tetramer. In other embodiments, the tetramer may be internalized and degraded and/or may separate from the cell without a further method step. In some embodiments, the method yet further comprises or alternatively consists essentially of, or yet further consists of, culturing the anti-tumor CD8+ cytotoxic T-cells under conditions for expansion of the anti-tumor CD8+ cytotoxic T-cell to a clonal population, thereby generating a clonal population of the anti-tumor CD8+ cytotoxic T-cells. In some embodiments, the method yet further comprises or alternatively consists essentially of, or yet further consists of, modifying the anti-tumor CD8+ cytotoxic T-cells to express an engineered T-cell receptor, such as a chimeric antigen receptor, on the cell surface. The resulting anti-tumor CD8+ cytotoxic T-cells—whether isolated, yet further expanded, and/or yet further engineered—have diagnostic, prognostic and therapeutic uses as described herein. Not to be bound by theory, it is believed that the population of anti-tumor CD8+ cytotoxic T-cells generated by the methods described herein have superior anti-tumor activity than other populations of T-cells.

The population of cells suspected of comprising the anti-tumor cytotoxic CD8+ T-cell comprises CD8+ T-cells. The anti-tumor cytotoxic CD8+ T-cell is a cytotoxic T-cell and/or a precursor thereof which is CD8+ and expresses CD8αα on its surface.

Further aspects of the disclosure relate to a population of anti-tumor CD8+ cytotoxic T-cells prepared by the methods disclosed herein, i.e., anti-tumor CD8+ cytotoxic T-cells that bind to a TL tetramer. Still further aspects relate to a composition comprising one or more of: the anti-tumor CD8+ cytotoxic T-cell bound to the TL tetramer; the isolated anti-tumor CD8+ cytotoxic T-cell; and the clonal population of anti-tumor CD8+ cytotoxic T-cells, and a carrier, optionally a pharmaceutically acceptable carrier. In one aspect, the one or more anti-tumor CD8+ cytotoxic T-cell bound to the TL tetramer; the isolated anti-tumor CD8+ cytotoxic T-cell; the substantially homogeneous; and the clonal population of anti-tumor CD8+ cytotoxic T-cells, are present in the composition in a therapeutically effective amount. In some embodiments, the composition further comprises or alternatively consists essentially of one or more of CD4+ cytotoxic T-cells and an immune checkpoint inhibitor, that also can be present in a therapeutically effective amount.

Additional aspects relate to a method of treating a tumor or cancer or eliciting an anti-tumor immune response in a subject in need thereof, the method comprising, or alternatively consisting essentially of, or yet further consisting of, administering an effective amount of any one of the population, substantially homogeneous population of cells, clonal population, or composition disclosed herein. In some embodiments, the method further comprises or alternatively consists essentially of, or yet further consists of, administering an effective amount of one or more cytoreductive therapy and/or immunotherapy to the subject. In some embodiments, the method comprises contacting a cancer or tumor cell isolated from the subject with an effective amount of the therapy, and assaying for the growth inhibition effect of the cell population or the compositions, prior to administration of the cell populations or compositions to the subject. In some embodiments, the method comprises assaying for the therapeutic effect of the therapy, after administration of the therapy to the subject. The subject can be any animal, e.g., a mammal such as a human subject.

Still further aspects relate to diagnostic methods using a TL tetramer. For example, provided herein is a method of selecting a treatment for a tumor or cancer in a subject in need thereof, comprising: administering a plurality of detectably labeled TL tetramers to the subject, detecting the TL tetramers in the subject to determine the concentration of anti-tumor CD8+ cytotoxic T-cells, and selecting the appropriate cytoreductive and/or immunotherapy from the measured concentration of the cells detected. In some method aspects, the subject is a mammal, optionally a canine, equine, feline, or a human patient.

Also provided is a kit for generating, detecting and expanding a population of high affinity anti-tumor CD8+ cytotoxic T-cells generated according the method of isolation described herein comprising a TL tetramer and instructions for use.

BRIEF DESCRIPTION OF THE DRAWINGS

10⁶ B16-OVA tumor cells. Tumor growth was measured as indicated over a period of two weeks

FIG. 10C shoes photographs of tumors examined in animals that were anesthetized briefly with isofluorane 14 days after cell implantation. FIG. 10D depicts tumor volume and survival in the respective panels. The left panel shows the volume of B16-OVA tumor implanted in Rag2−/− mice injected or not with reprogrammed CD8αα CD4 OT-II cells. The right panel shows a survival curve of each group of mice after tumor challenge. **P<0.01 by T-test for tumor volume (left) and log-rank test for survival analysis (right). n=4-5 mice per group. Data are representative of three independent experiments.

FIG. 24 shows a flowchart of studies for development of the disclosed technology.

DETAILED DESCRIPTION

Figure 1:
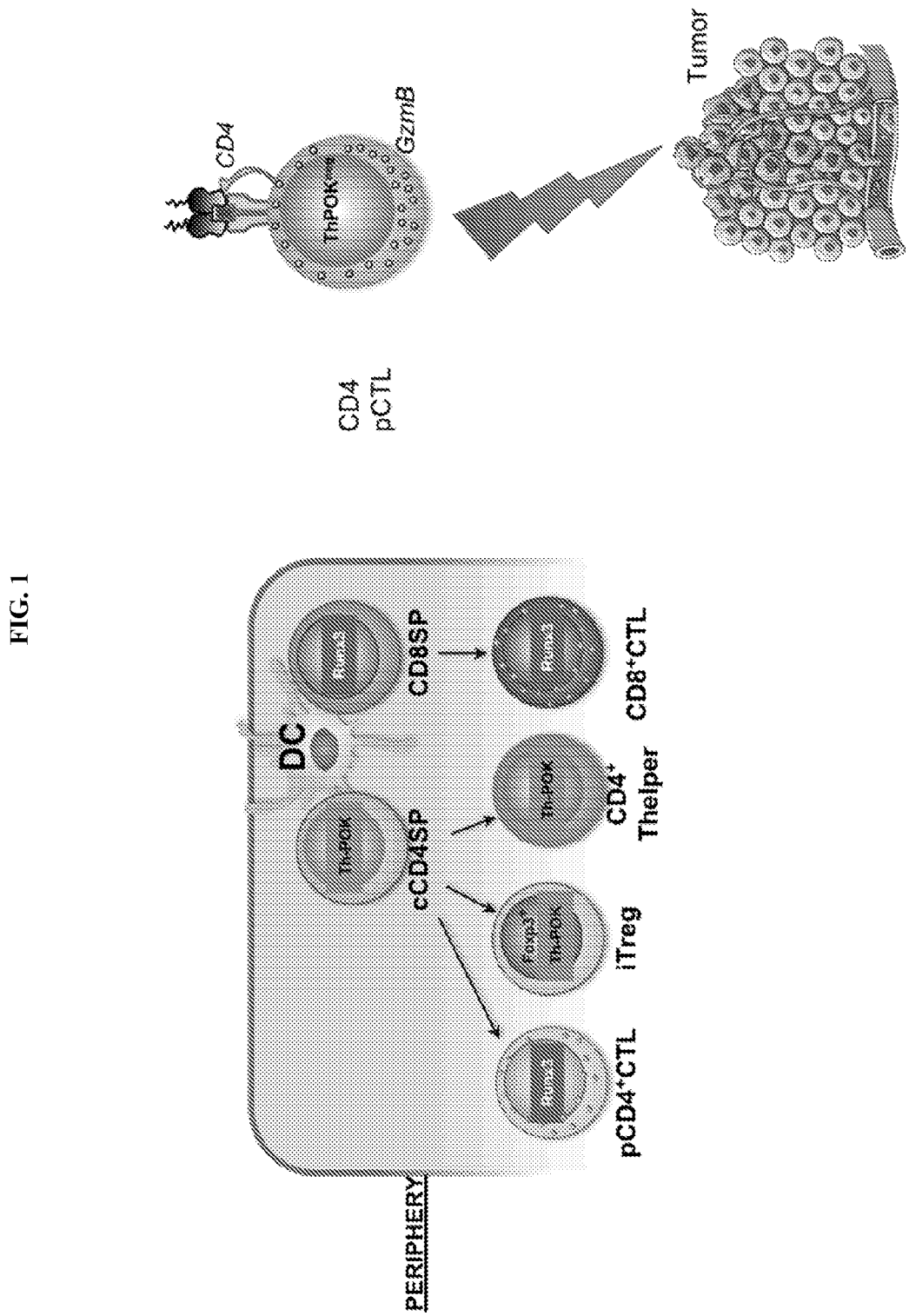
FIG. 1 is a schematic of the different T-cells subtypes found in the periphery. Differentiation thereof is an antigen-dependent process.
Figure 2:
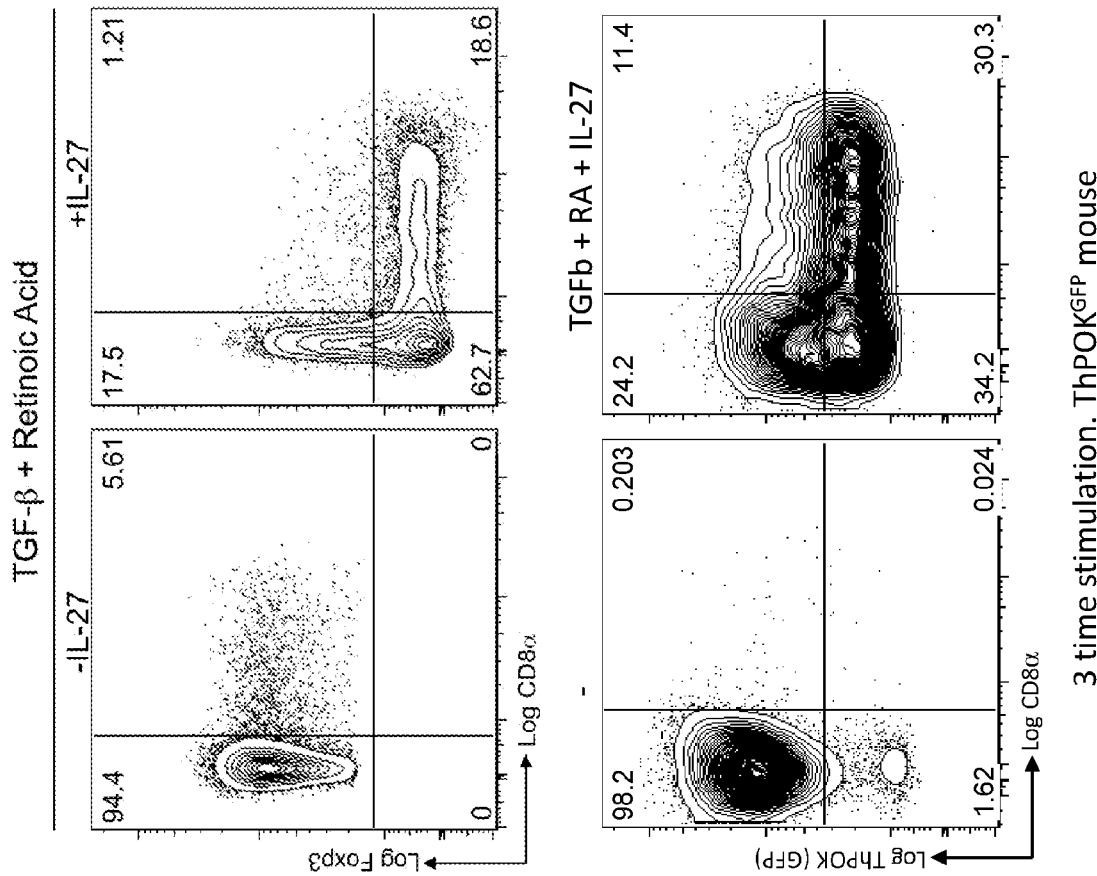
FIG. 2 demonstrates that a combination comprising retinoic acid, TGF-β, and IL-27 ("RABI27") can successfully reprogram CD4+ effector/Treg cells to cytotoxic T-cells. Naïve spleen CD4 T helper cells were stimulated in vitro with anti-CD3/28 and with (either TGFb/RA or TGFb/RA/IL27) or without cytokines for 3 cycles of each 3 days. Activated cells were then analyzed for Foxp3 or Thpok expression and cell surface expression of CD8α.
Figure 3:
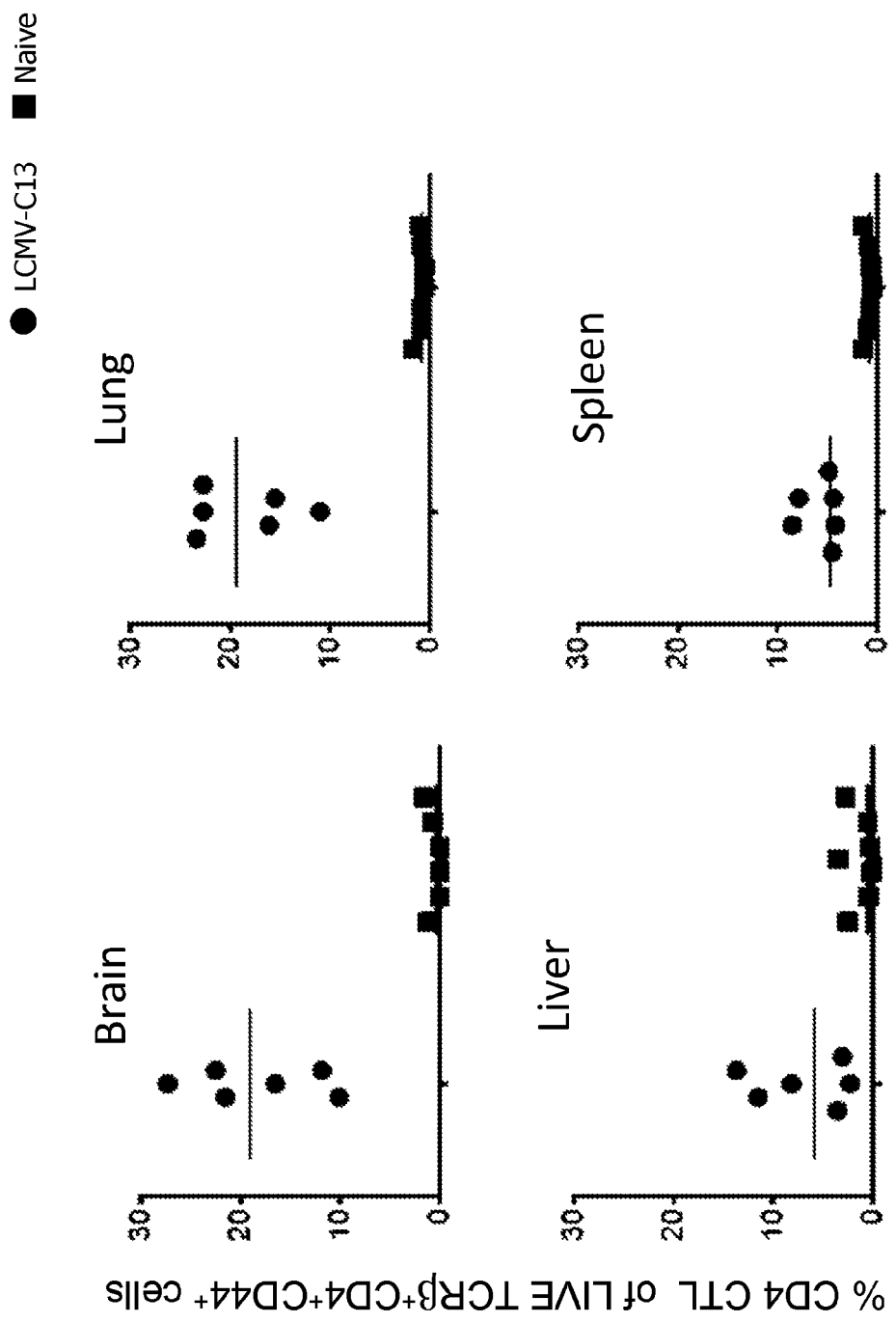
FIG. 3 shows CD4+ cytotoxic T-cell (CTL) reprogramming occurs in peripheral tissues in response to chronic (viral) stimulation. Mature CD4+ T helper cells reprogram to CTL in response to a chronic viral infection. Naïve mice were infected with LCMV (clone 13). Four weeks post infection CD4+ T-cells were isolated from various tissues and analyzed for the presence of reprogrammed CD4+ CTL (ThPOK negative) among antigen-experienced (CD44+) CD4+ T-cells.

It is to be understood that the present disclosure is not limited to particular aspects described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meanings as commonly understood by one of ordinary skill in the art to which this technology belongs. Although any methods and materials similar or equivalent to those described herein can be used in the practice or testing of the present technology, the preferred methods, devices and materials are now described. All technical and patent publications cited herein are incorporated herein by reference in their entirety. Nothing herein is to be construed as an admission that the present technology is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Green and Sambrook eds. (2012) Molecular Cloning: A Laboratory Manual, 4th edition; the series Ausubel et al. eds. (2015) Current Protocols in Molecular Biology; the series Methods in Enzymology (Academic Press, Inc., N.Y.); MacPherson et al. (2015) PCR 1: A Practical Approach (IRL Press at Oxford University Press); MacPherson et al. (1995) PCR 2: A Practical Approach; McPherson et al. (2006) PCR: The Basics (Garland Science); Harlow and Lane eds. (1999) Antibodies, A Laboratory Manual; Greenfield ed. (2014) Antibodies, A Laboratory Manual; Freshney (2010) Culture of Animal Cells: A Manual of Basic Technique, 6th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Herdewijn ed. (2005) Oligonucleotide Synthesis: Methods and Applications; Hames and Higgins eds. (1984) Transcription and Translation; Buzdin and Lukyanov ed. (2007) Nucleic Acids Hybridization: Modern Applications; Immobilized Cells and Enzymes (TRL Press (1986)); Grandi ed. (2007) In Vitro Transcription and Translation Protocols, 2nd edition; Guisan ed. (2006) Immobilization of Enzymes and Cells; Perbal (1988) A Practical Guide to Molecular Cloning, 2nd edition; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Lundblad and Macdonald eds. (2010) Handbook of Biochemistry and Molecular Biology, 4th edition; and Herzenberg et al. eds (1996) Weir's Handbook of Experimental Immunology, 5th edition.

Throughout this disclosure, various publications, patents and published patent specifications are referenced by an identifying citation. All publications, patent applications, patents, and other references mentioned herein are expressly incorporated by reference in their entirety, to the same extent as if each were incorporated by reference individually. In case of conflict, the present specification, including definitions, will control.

Definitions

As used herein, the singular forms "a", "an", and "the" include plural referents unless the context clearly dictates otherwise. Thus, for example, reference to "a peptide" includes a plurality of peptides, including mixtures thereof. The term "at least one" intends one or more.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about." It also is to be understood, although not always explicitly stated, that the reagents described herein are merely exemplary and that equivalents of such are known in the art.

As used herein, the term "about" is used to indicate that a value includes the standard deviation of error for the device or method being employed to determine the value. The term "about" when used before a numerical designation, e.g., temperature, time, amount, and concentration, including range, indicates approximations which may vary by (+) or (−) 15%, 10%, 5%, 3%, 2%, or 1%.

As used herein, the term "administer" and "administering" are used to mean introducing the therapeutic agent (e.g., polynucleotide, vector, cell, modified cell, population) into a subject. The therapeutic administration of this substance serves to attenuate any symptom, or prevent additional symptoms from arising. When administration is for the purposes of preventing or reducing the likelihood of developing a tumor or cancer, the substance is provided in advance of any visible or detectable symptom or after thereof. The therapy can be combined with other known anti-cancer therapies and can be administered as a first-line, second-line, third-line, fourth line, or fifth-line therapy. Routes of administration include, but are not limited to, intravenous, by infusion, oral (such as a tablet, capsule or suspension), topical, transdermal, intranasal, vaginal, rectal, subcutaneous intravenous, intra-arterial, intramuscular, intraosseous, intraperitoneal, epidural and intrathecal.

As used herein, the term "animal" refers to living multi-cellular vertebrate organisms, a category that includes, for example, mammals and birds. The term "mammal" includes both human and non-human mammals. The terms "subject," "host," "individual," and "patient" are as used interchangeably herein to refer to human and veterinary subjects, for example, humans, animals, non-human primates, dogs, cats, sheep, mice, horses, and cows. In some embodiments, the subject is a human. In some aspects, the subject is suffering from a disease or condition to be treated by one of the methods disclosed herein.

A "composition" typically intends a combination of the active agent, e.g., a population of T-cells, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Further examples of composition components include but are not limited to cryoprotectants and preservatives. Non-limiting examples of suitable cryoprotectants for use in the compositions disclosed herein include DMSO and/or glycerol mixed with FBS (fetal bovine serum); polyvinyl-pyrrolidone, ethylene glycol or polyethylene glycol (PEG), methanol, and methyl acetamide. Non-limiting examples of preservatives for use in the compositions disclosed herein include DMSO, sodium benzoate, calcium propionate, sodium azide, ethanol, and fetal bovine serum.

Carriers also include pharmaceutical excipients and additives proteins, peptides, amino acids, lipids, and carbohydrates (e.g., sugars, including monosaccharides, di-, tri-, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/ antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

As used herein, the term "comprising" or "comprises" is intended to mean that the compositions and methods that include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed disclosure, such as compositions for treating or preventing cancer or tumor. "Consisting of" shall mean excluding more than trace elements of other ingredients and substantial method steps. Embodiments defined by each of these transition terms are within the scope of this disclosure.

As used herein, the term "autologous," in reference to cells refers to cells that are isolated and infused back into the same subject (recipient or host). "Allogeneic" refers to non-autologous cells.

"Immune cells" include all cells that are produced by hematopoietic stem cells (HSC) including, but not limited to, HSCs, white blood cells (leukocytes), lymphocytes (including T-cells, B cells, and natural killer (NK) cells) and myeloid-derived cells (neutrophils, eosinophils, basophils, monocytes, macrophages, dendritic cells). "Leukocytes" include but are not limited to lymphocytes, granulocytes, monocytes, and macrophages.

As used herein, the term "T-cell," refers to a type of lymphocyte that matures in the thymus. T-cells play an important role in cell-mediated immunity and are distinguished from other lymphocytes, such as B cells, by the presence of a T-cell receptor (TCR) on the cell surface. T-cells may either be isolated or obtained from a commercially available source. "T-cell" includes all types of immune cells expressing CD3. Non-limiting examples of T-cells and markers for isolation thereof including naïve T-cells (CCR7+, CD45RA+), double-negative T-cells (CD3+, CD4−, CD8−), CD4+ T-cells (such as but not limited to T-helper ("Th") cells such as: T-regulatory cells, Tregs (CD25+), Th1 cells (CDCR3+, CCR5+), Th2 cells (CXCR4+, CCR3+, CCR4+, CCR5+, CCR7+, CD30+), Th17 cells (CD4+, IL-17A+) and naïve CD4+ T-cells (CD4+, CD45RA+, CD62L+)), CD8+ T-cells, natural killer T-cells, central memory T-cells (CCR7+, CD45RA−), effector memory T-cells (CCR7−, CD45RA−), and gamma-delta T-cells. Natural killer T-cells (NKT) co-express NK-cell markers and a semi-invariant T-cell receptor (TCR). They are implicated in the regulation of immune responses associated with a broad range of diseases. Non-limiting examples of commercially available T-cell lines include lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™), TALL-104 cytotoxic human T-cell line (ATCC #CRL-11386). Further examples include but are not limited to mature T-cell lines, e.g., such as Deglis, EBT-8, HPB-MLp-W, HUT 78, HUT 102, Karpas 384, Ki 225, My-La, Se-Ax, SKW-3, SMZ-1 and T34; and immature T-cell lines, e.g., ALL-SIL, Be13, CCRF-CEM, CML-T1, DND-41, DU. 528, EU-9, HD-Mar, HPB-ALL, H-SB2, HT-1, JK-T1, Jurkat, Karpas 45, KE-37, KOPT-K1, K-T1, L-KAW, Loucy, MAT, MOLT-1, MOLT 3, MOLT-4, MOLT 13, MOLT-16, MT-1, MT-ALL, P12/ Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4; 11 (ATCC CRL-1873), CCRF-CEM (ATCC CRM-CCL-119); and cutaneous T-cell lymphoma lines, e.g., HuT78 (ATCC CRM-TIB-161), MJ[G11] (ATCC CRL-8294), HuT102 (ATCC TIB-162). Null leukemia cell lines, including but not limited to REH, NALL-1, KM-3, L92-221, are a another commercially available source of immune cells, as are cell lines derived from other leukemias and lymphomas, such as K562 erythroleukemia, THP-1 monocytic leukemia, U937 lymphoma, HEL erythroleukemia, HL60 leukemia, HMC-1 leukemia, KG-1 leukemia, U266 myeloma. Non-limiting exemplary sources for such commercially available cell lines include the American Type Culture Collection, or ATCC, (http://www.atcc.org/) and the German Collection of Microorganisms and Cell Cultures (https://www.dsmz.de/).

A "cytotoxic cell" intends a cell that is capable of killing other cells or microbes. Examples of cytotoxic cells include but are not limited to CD8+ T-cells, certain CD4+ T-cells, double-negative T-cells, gamma delta T-cells, natural-killer (NK) cells, NK T-cells, and neutrophils, which cells are capable of mediating cytotoxicity responses.

As used herein, the term "CD4+ cytotoxic T-cells" refers to a population of T-cells that express CD4 on their surface and, generally, are ThPOK⁻ (downregulated). These CD4+ cytotoxic T-cells can also be characterized by CD8αα expression, downregulation of Gata3, and upregulation of Runx3 and Tbet. Sequences for the mentioned transcription factors and surface proteins are provided at the following accession numbers: ThPOK (Uniprot: O15156 (human); Q64321 (mouse); also known as ZBTB7B), Gata3 (Uniprot: P23771 (human); P23772 (mouse); P23825 (chicken)), Runx3 (Uniprot: Q13761 (human); Q64131 (mouse); Q91ZK1 (rat)); Tbet (Uniprot: Q9UL17 (human); Q5PSB0 (mouse); E1UGZ0 (rainbow trout), also known as TBX21), CD4 (Uniprot: P01730 (human); P06332 (mouse); P33705 (dog)), and CD8α (Uniprot: P01732 (human); P01731 (mouse); P33706 (dog), CD8αα being a homodimer of this protein). It should be understood that these sequences are non-limiting and that detection of any of these transcription factors and/or surface proteins may employ or target suitable isoforms, fragments, and biological equivalents thereof; further homologous and/or orthologous sequences for relevant species can be found through the Uniprot database, www.uniprot.org.

The term "CD4+ T-cells" refers to T-cells that express CD4 on their surface and, generally, are ThPOK+(upregulated); these cells include naïve CD4+ T-cells, Th1 T-cells, Th17 T-cells, and T-regulatory cells. It is well understood that surface markers, e.g., CD8αα and CD4, can be identified by antibodies to the listed surface markers, i.e., an anti-CD8α antibody or an anti-CD4 antibody. When used in this context the prefix "anti-" and the descriptor "antibody" refer to an antibody, fragment, derivative, or biological equivalent thereof that recognizes or binds the recited protein, e.g., anti-CD4 antibody recognizes and binds CD4. As used herein, the term "CD8+ cytotoxic T-cell" refers to a cytotoxic T-cell and/or a precursor thereof which is CD8+ and expresses CD8αα on its surface. The CD8αα surface expression is an indicator that these CD8+ cytotoxic T-cells have high affinity to the antigen against which they were generated. For example, those CD8+ cytotoxic T-cell generated against a tumor antigen are necessarily tumor-specific. An "anti-tumor CD8+ cytotoxic T-cell" is understood to be tumor specific. As noted above, this tumor specificity may either be based on the antigen against which the CD8+ cytotoxic T-cell was generated or may be present as a result of an engineered T-cell receptor, such as a chimeric antigen receptor.

As used herein, "CD8αα" refers to a homodimer of CD8α (also known as CD8a) that may be expressed on the surface of certain T-cells. Non-limiting exemplary amino acid sequences for CD8α can be found in the Uniprot database under accession numbers P01732 (human CD8α); P01731 (mouse CD8α); P33706 (dog CD8α); other homologs of the same may be found in the Uniprot database, i.e., at www.uniprot.org. "CD8αβ " refers to a heterodimer of CD8α and CD8β (also known as CD8b) that is expressed on the surface of CD8+ T-cells. Non-limiting exemplary amino acid sequences for CD8β can be found in the Uniprot database under accession numbers P10966 (human CD80); P10300 (mouse CD80); P79336 (cat CD80); other homologs of the same may also be found in the Uniprot database, i.e., at www.uniprot.org. As used herein, "anti-CD8α" and "anti-CD80" refer to antibodies or fragments, derivatives, or biological equivalents thereof that recognizes and bind to CD8α and CD80, respectively. These may be recombinantly expressed, generated by exposing antibody producing cells to CD8α or CD80, or other means known in the art, using for example, the proteins described herein. Further they can be purchased from commercial vendors, such as but not limited to Becton Dickinson.

When used herein in reference to one or more cell populations, the term "substantially homogenous" refers to a population that comprises at least 60%, alternatively, at least 65%, or alternatively, at least 70%, or alternatively, at least 75%, or alternatively, at least 80%, or alternatively at least 85%, or alternatively, at least 90%, or alternatively at least 95% or alternatively at least 98% of the same cell type or the same marker profile. In contrast, the term "clonal" describing a cell population, refers to cells that are genetically identical, i.e. 100% of the same cell type and all originating from a single ancestor.

As used herein, the term "label" intends a directly or indirectly detectable cell, compound or composition that is conjugated directly or indirectly to the cell or composition to be detected or isolated, e.g., N-terminal histidine tags (N-His), HA tag, FLAG tag, 6XHis (SEQ ID NO: 1) tag, magnetically active isotopes, e.g., 115Sn, 117Sn and 119Sn, a non-radioactive isotopes such as 13C and 15N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals (6th ed). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In another aspect, the fluorescent label is functionalized to facilitate covalent attachment to a cellular component present in or on the surface of the cell or tissue such as a cell surface marker. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, self-antigens, protozoa and other parasitic antigens, tumor/cancer antigens, antigens involved in autoimmune disease, allergy and graft rejection, toxins, and other miscellaneous antigens.

As used herein, "tumor-specific" used in reference to a cell that specifically recognizes an antigen, epitope, or fragment thereof displayed by or associated with a tumor or cancer. Non-limiting, exemplary tumor antigens, epitopes, or fragments thereof may be determined for a particular tumor or cancer based on the epitope screening techniques, mechanisms, and methods described herein. The tumor specificity of a cell can occur naturally, be engineered, or stimulated. For example, tumor-specific Tregs, other T-helper cells, or effector T-cells may be found naturally in the tumor microenvironment. Alternatively, T-cells may be modified to express an engineered TCR designed to be tumor-specific. Another option is to stimulate TCRs with repeated exposure to an antigen.

As used herein, the term "engineered T-cell receptor" refers to a molecule comprising the elements of (a) an extracellular antigen binding domain, (b) a transmembrane domain, and (c) an intracellular signaling domain. In some aspects, an engineered T-cell receptor is a genetically modified TCR, a modified TCR, a recombinant TCR, a transgenic TCR, a partial TCR, a chimeric fusion protein, a chimeric antigen receptor ("CAR"), a first generation CAR, a second generation CAR, a third generation CAR, or a fourth generation CAR (also known as a "TRUCK"). In some aspects, the engineered T-cell receptor comprises an antibody or a fragment of an antibody. In particular aspects, the engineered T-cell receptor is a genetically modified TCR or a CAR.

The term "chimeric antigen receptor" (CAR), as used herein, refers to a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is also known as a "T-body", "chimeric receptor", or "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell. In certain embodiments, the intracellular domain may comprise, alternatively consist essentially of, or yet further comprise one or more costimulatory signaling domains in addition to the primary signaling domain. The "transmembrane domain" means any oligopeptide or polypeptide known to span the cell membrane and that can function to link the extracellular and signaling domains. A chimeric antigen receptor may optionally comprise a "hinge domain" which serves as a linker between the extracellular and transmembrane domains. Non-limiting exemplary polynucleotide sequences that encode for components of each domain are disclosed herein, e.g.: Hinge domain: IgG1 heavy chain hinge sequence: CTCGAGCCCAAATCTTGTGACAAAACTCACACATGCCCACCGTGCCCG (SEQ ID NO: 2); Transmembrane domain: CD28 transmembrane region: TTTTGGGTGCTGGTGGTGGTTGGTGGAGTCCTGGCTTGCTATAGCTTGCTAGTAA CAGTGGCCTTTATTATTTTCTGGGTG (SEQ ID NO: 3); Intracellular domain: 4-1BB costimulatory signaling region: AAACGGGGCAGAAAGAAACTCCTGTATATATTCAAACAACCATTTATGAGACCA GTACAAACTACTCAAGAGGAAGATGGCTGTAGCTGCCGATTTCCAGAAGAAGAA GAAGGAGGATGTGAACTG (SEQ ID NO: 4); Intracellular domain: CD28 costimulatory signaling region: AGGAGTAAGAGGAGCAGGCTCCTGCACAGTGACTACATGAACATGACTCCCCGC CGCCCCGGGCCCACCCGCAAGCATTACCAGCCCTATGCCCCACCACGCGACTTCG CAGCCTATCGCTCC (SEQ ID NO: 5); Intracellular domain: CD3 zeta signaling region: AGAGTGAAGTTCAGCAGGAGCGCAGACGCCCCCGCGTACCAGCAGGGCCAGAAC CAGCTCTATAACGAGCTCAATCTAGGACGAAGAGAGGAGTACGATGTTTTGGAC AAGAGACGTGGCCGGGACCCTGAGATGGGGGGAAAGCCGAGAAGGAAGAACCC TCAGGAAGGCCTGTACAATGAACTGCAGAAAGATAAGATGGCGGAGGCCTACAG TGAGATTGGGATGAAAGGCGAGCGCCGGAGGGGCAAGGGGCACGATGGCCTTTA CCAGGGTCTCAGTACAGCCACCAAGGACACCTACGACGCCCTTCACATGCAGGC CCTGCCCCCTCGCTAA (SEQ ID NO: 6).

Further embodiments of each exemplary domain component include other proteins that have analogous biological function that share at least 70%, or alternatively at least 80% amino acid sequence identity, preferably 90% sequence identity, more preferably at least 95% sequence identity with the proteins encoded by the above disclosed nucleic acid sequences. Further, non-limiting examples of such domains are provided herein.

An "effective amount" or "efficacious amount" is an amount sufficient to achieve the intended purpose, non-limiting examples of such include: initiation of the immune response, modulation of the immune response, suppression of an inflammatory response and modulation of T-cell activity or T-cell populations. In one aspect, the effective amount is one that functions to achieve a stated therapeutic purpose, e.g., a therapeutically effective amount. As described herein in detail, the effective amount, or dosage, depends on the purpose and the composition, and can be determined according to the present disclosure.

As used herein, "treating" or "treatment" of a disease or condition in a subject refers to (1) inhibiting or reducing or preventing the symptoms or disease or condition from occurring in a subject that is predisposed or does not yet display symptoms of the disease; (2) inhibiting, reducing or preventing the disease or condition or arresting its development; or (3) ameliorating or causing regression of the disease or condition or the symptoms of the disease or condition. As understood in the art, "treatment" is an approach for obtaining beneficial or desired results, including clinical results. For the purposes of the present technology, beneficial or desired results can include one or more, but are not limited to, prevention, alleviation or amelioration of one or more symptoms, diminishment of extent of a condition (including a disease), stabilized (i.e., not worsening) state of a condition (including disease), prevention, delay or slowing of condition (including disease), progression, amelioration or palliation of the condition (including disease), states and remission (whether partial or total), whether detectable or undetectable. In one aspect, the term "treatment" excludes prevention.

"Cytoreductive therapy," as used herein, refers to cancer therapy aimed at debulking a cancerous tumor. Such therapy includes but is not limited to chemotherapy, cryotherapy, and radiation therapy. Agents that act to reduce cellular proliferation are known in the art and widely used. Chemotherapy drugs that kill cancer cells only when they are dividing are termed cell-cycle specific. These drugs include agents that act in S-phase, including topoisomerase inhibitors and anti-metabolites.

Toposiomerase inhibitors are drugs that interfere with the action of topoisomerase enzymes (topoisomerase I and II). During the process of chemo treatments, topoisomerase enzymes control the manipulation of the structure of DNA necessary for replication, and are thus cell cycle specific. Examples of topoisomerase I inhibitors include the camptothecan analogs listed above, irinotecan and topotecan. Examples of topoisomerase II inhibitors include amsacrine, etoposide, etoposide phosphate, and teniposide.

Antimetabolites are usually analogs of normal metabolic substrates, often interfering with processes involved in chromosomal replication. They attack cells at very specific phases in the cycle. Antimetabolites include folic acid antagonists, e.g., methotrexate; pyrimidine antagonist, e.g., 5-fluorouracil, foxuridine, cytarabine, capecitabine, and gemcitabine; purine antagonist, e.g., 6-µmercaptopurine and 6-thioguanine; adenosine deaminase inhibitor, e.g., cladribine, fludarabine, nelarabine and pentostatin; and the like.

Plant alkaloids are derived from certain types of plants. The vinca alkaloids are made from the periwinkle plant (Catharanthus rosea). The taxanes are made from the bark of the Pacific Yew tree (taxus). The vinca alkaloids and taxanes are also known as antimicrotubule agents. The podophyllotoxins are derived from the May apple plant. Camptothecan analogs are derived from the Asian "Happy Tree" (Camptotheca acuminata). Podophyllotoxins and camptothecan analogs are also classified as topoisomerase inhibitors. The plant alkaloids are generally cell-cycle specific.

Examples of these agents include vinca alkaloids, e.g., vincristine, vinblastine and vinorelbine; taxanes, e.g., paclitaxel and docetaxel; podophyllotoxins, e.g., etoposide and tenisopide; and camptothecan analogs, e.g., irinotecan and topotecan.

Cryotherapy includes, but is not limited to, therapies involving decreasing the temperature, for example, hypothermic therapy.

Radiation therapy includes, but is not limited to, exposure to radiation, e.g., ionizing radiation, UV radiation, as known in the art. Exemplary dosages include, but are not limited to, a dose of ionizing radiation at a range from at least about 2 Gy to not more than about 10 Gy and/or a dose of ultraviolet radiation at a range from at least about 5 J/m$^2$ to not more than about 50 J/m$^2$, usually about 10 J/m$^2$.

"Immunotherapy," as used herein, refers to cancer therapies that enhance the immune response to a tumor or cancer. Such therapy includes but is not limited to adoptive cell therapies, such as those utilizing CAR T-cells, CD4+ or CD8+ cytotoxic cells, natural killer cells, or equivalents thereof; monoclonal antibodies and immunoconjugate based therapies designed to target and destroy tumors and/or cancer cells; cytokine therapy, such as interferon gamma ("IFNγ") treatment; and vaccination.

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer Institute website at www.cancer.gov. Typically, a patient is given a subsequent chemotherapy regimen because the patient did not show a positive clinical or sub-clinical response to the first line therapy or the first line therapy has stopped.

As used herein, the term "acetate" refers to a salt or ester of acetic acid, containing the anion CH$_3$COO— or the group OCCH$_3$. A non-limiting exemplary structure of acetate (ion) is depicted below and can be accessed with CAS Registry No. 71-50-1:

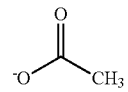

As used herein, the term "retinoic acid" refers to a metabolite of vitamin A (retinol) sometimes referred to as "vitamin A acid" or "RA" and having the chemical formula C$_{20}$H$_{28}$O$_2$, as well as pharmaceutically acceptable salts and biological equivalents thereof. A non-limiting exemplary structure of retinoic acid is depicted below and can be accessed with CAS Registry No. 302-79-4:

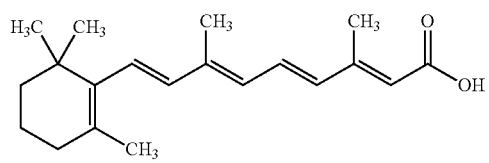 [SMILES: CC1=C(/C=C/C(C)=C/C=C/C(C)=C/C(=O)O)C(C)(C)CCC1]

As used herein, the term "TGF-β" refers to all isoforms of the multifunctional homodimeric cytokine belonging to the transforming growth factor superfamily referred to by this name or "transforming growth factor beta," "TGFB," or other variations thereof, as well as fragments and biological equivalents thereof. Generally, TGF-β is capable of complexing with other factors to form a serine/threonine kinase complex and binds to TGF-β receptors, which generally comprise both type 1 and type 2 receptor subunits. This binding can activate a signaling cascade, which results in downstream immune effects. Non-limiting exemplary amino acid sequences for TGF-β can be found in the Uniprot database under accession numbers P01137 (human TGFB1), P04202 (murine TGFB1), P17246 (rat TGFB1), P61812 (human TGFB2), P27090 (mouse TGFB2), Q07257 (TGFB2), P10600 (human TGFB3), Q99K17 (murine TGFB3), and Q07258 (rat TGFB3); other homologs of the same may also be found in the Uniprot database, i.e., at www.uniprot.org. TGF-β can be produced in vivo and isolated or in vitro, e.g., using a recombinant expression system and/or TGF-β producing cell line. Alternatively, it may be purchased through a variety of commercially available sources, e.g., Sigma Aldrich, Thermo-Fisher, R&D Systems, Abcam, Bio-Rad, Milipore, and a variety of other commercial vendors of biological products.

As used herein, the term "IL-27" refers to all isoforms of the heterodimeric cytokine referred to by this name or "Interleukin 27," "IL27," or other variations thereof, as well as fragments, subunits, and biological equivalents thereof. Equivalents of IL-27 include other members of the IL-12 family, such as but not limited to IL-12, IL-23, and IL-35. Members of this family are characterized by being made a heterodimeric complex comprising an α chain (p19, p28, or p35, in humans) and αβ chain (p40 or Ebi3, in humans); this feature is unique to members of the IL-12 family of cytokines. The amino acid and polynucleotide sequences are known in the art and recorded on publicly accessible databases. Generally, IL-27 is expressed by antigen presenting cells and interacts with its corresponding receptor—IL-27R. The interaction between IL-27 and IL-27R can affect signaling pathways including JAK-STAT and p38 MAPK pathways and can result in downstream immune effects. Non-limiting exemplary amino acid sequences of IL-27 can be found in the Uniprot database under accession numbers Q8NEV9 (human IL-27 alpha subunit), Q8K3I6 (murine IL-27 alpha subunit), Q14213 (human IL-27 beta subunit), and O35228 (murine IL-27 beta subunit); other homologs of the same may also be found in the Uniprot database, i.e., at www.uniprot.org. IL-27 can be produced in vivo and isolated or in vitro, e.g., using a recombinant expression system and/or IL-27 producing cell line. Alternatively, it may be purchased through a variety of commercially available sources, e.g., Thermo-Fisher, R&D Systems, Abcam, Miltenyi, and a variety of other commercial vendors of biological products.

As used herein, the term "TL tetramer" refers to a tetramer comprising four units of non-classical MHC class I thymus leukemia antigen ("TL") and biological equivalents thereof, e.g., multimers with comparable function and specificity to CD8αα. A non-limiting exemplary method of generating such a tetramer is provided in Leishman et al. (2001) Science 294(5548):1936-1939. In this method, a baculovirus expression system is used. Soluble TL (T18d) heavy chain was amplified by the polymerase chain reaction and cloned ahead of the BirA tag coding sequence into the Sal I/Bam HI sites of the mCD1/b2-microglobulin (b2m) pBacp10pH expression vector, replacing the CD1d heavy chain. The vectors were transfected and tetramers were produced. An non-limiting exemplary method of this transfection and production involves the following steps. The expression vector is cotransfected with linearized baculovirus DNA into cells (Invitrogen) using a reagent. Recombinant virus is collected, amplified, and cloned by serial dilution method. The virus with highest level of secretion is used for protein production. Soluble protein is produced by infecting adherenT-cells supernatant was harvested after the infection, dialyzed, and purified. The resulting purified product can be tetramerized by adding neutravidin-PE at a specific molar ratio. "TL" refers to all isoforms of the non-classical MHC class I antigen referred to as thymus leukemia antigen and homologs and biological equivalents thereof. A non-limiting exemplary amino acid sequence of TL can be found in the Uniprot database under accession number Q62324 (murine TL); a non-limiting exemplary DNA sequence is disclosed in Fisher (1985), "Structure of a Gene Encoding a Murine Thymus Leukemia Antigen, and Organization of Tla Genes in the BALB/c Mouse." J. Exp. Med. 162(2):528-545; human, canine, feline, and other mammalian homologs of the same may also be found in the Uniprot database, i.e., at www.uniprot.org. TL can be produced in vivo or ex vivo and isolated or in vitro, e.g., using a recombinant expression system and/or TL producing cell line. Alternatively, it may be purchased through a variety of commercially available sources. Non-limiting examples of sequences used to generate a TL tetramer include:

```
>sp|P01899|HA11_MOUSE H-2 class I histo-
compatibility antigen, D-B alpha chain
OS = Mus musculus OX= 10090 GN = H2-D1
PE = 1 SV = 2
                                    (SEQ ID NO: 7)
MGAMAPRTLLLLLAAALAPTQTRAGPHSMRYFETAVSRPGLEEPRYISVG

YVDNKEFVRFDSDAENPRYEPRAPWMEQEGPEYWERETQKAKGQEQWFRV

SLRNLLGYYNQSAGGSHTLQQMSGCDLGSDWRLLRGYLQFAYEGRDYIAL

NEDLKTWTAADMAAQITRRKWEQSGAAEHYKAYLEGECVEWLHRYLKNGN

ATLLRTDSPKAHVTHHPRSKGEVTLRCWALGFYPADITLTWQLNGEELTQ

DMELVETRPAGDGTFQKWASVVVPLGKEQNYTCRVYHEGLPEPLTLRWEP

PPSTDSYMVIVAVLGVLGAMAIIGAVVAFVMKRRRNTGGKGGDYALAPGS

QSSEMSLRDCKA and equivalents thereof;

Unitprot ID Q62324 MOUSE thymus leukemia
antigen (fragment)
                                    (SEQ ID NO: 8)
GNGDDNTAAY QNEREHLSLT LGLNLRHSGW KLG and equivalents thereof;

>NP_032234.3 MOUSE H-2 class I histo-
compatibility antigen, TLA(B) alpha
chain precursor
                                    (SEQ ID NO: 9)
MRMGTMVPGTLLILLAASQGQTQTCPGSHSLRYFYTALSRPAISEPWYIA

VGYLDDTQFVRFNSSGETATYKLSAPWVEQEGPEYWARETEIVTSNAQFF

RENLQTMLDYYNLSQNGSHTIQVMYGCEVEFFGSLFRAYEQHGYDGRDYI

ALNEDLKTWTAADTAAEITRSKWEQAGYTELRRTYLEGPCKDSLLRYLEN

RKKTQECTDPPKTHVTHHPRPEGYVTLRCWALRFYPADITLTWQLNGEEL

IQDTELVETRPAGDGTFQKWAAVVVPLGKEQKYTCHVYHEGLPEPLTLRW

EPPQTSMPNRTTVRALLGAMIILGFMSGSVMMWMRKNNGGNGDDNTAAYQ

NEREHLSLSPRAESEALGVEAGMKDLPSAPPLVS and equivalents thereof;
```

```
>sp|P14432.2|HA1T_MOUSE H-2 class I histo-
compatibility antigen, TLA(B) alpha chain
                                  (SEQ ID NO: 10)
MRMGTPVPGTLLILLAASQGQTQTCPGSHSLRYFYTALSRPAISEPWYIA

VGYLDDTQFVRFNSSGETATYKLSAPWVEQEGPEYWARETEIVTSNAQFF

RENLQTMLDYYNLSQNGSHTIQVMYGCEVEFFGSLFRAYEQHGYDGPDYI

ALNEDLKTWTAADTAAEITRSKWEQAGYTELRRTYLEGPCKDSLLRYLEN

RKKTQECTDPPKTHVTHHPRPEGYVTLRCWALRFYPADITLTWQLNGEEL

IQDTELVETRPAGDGTFQKWAAVVVPLGKEQKYTCHVYHEGLPEPLTLRW

EPPQTSMPNRTTVRALLGAMIILGFMSGSVMMWMRKNNGGNGDDNTAAYQ

NEREHLSLDPRAESEALGVEAGMKDLPSAPPLVS and equivalents thereof.

>AAA76608.2 HUMAN HLA-A2
                                  (SEQ ID NO: 11)
MAVMAPRTLVLLLSGALALTQTWAGSHSMRYFFTSVSRPGRGEPRFIAVG

YVDDTQFVRFDSDAASQRMEPRAPWIEQEGPEYWDGETRKVKAHSQTHRV

DLGTLRGYYNQSEAGSHTVQRMYGCDVGSDWRFLRGYHQYAYDGKDYIAL

KEDLRSWTAADMAAQTTKHKWEAAHVAEQLRAYLEGTCVEWLRRYLENGK

ETLQRTDAPKTHMTHHAVSDHEATLRCWALSFYPAEITLTWQRDGEDQTQ

DTELVETRPAGDGTFQKWAAVVVPSGQEQRYTCHVQHEGLPKPLTLRWEP

SSQPTIPIVGIIAGLVLFGAVITGAVVAAVMWRRKSSDRKGGSYSQAASS

DSAQGSDVSLTACKV and equivalents thereof;
and

>tr|P79495|P79495_HUMAN HLA-A2 antigen
(Fragment)
                                  (SEQ ID NO: 12)
FFTSVSRPGRGEPRFIAVGYVDDTQFVIM)SDAASQRMEPRAPWIEQEGP

EYWDGETRKVKAHSQTHRVDLGTLRGYYNQSEAGSHTVQRMCGCDVGSDW

RFLRGYHQYAYDGKDYIALKEDLRSWTAADMAAQTTKHKWEAAHVAEQLR

AYLEGTCVEWLRRYLE and equivalents thereof.
```

As used herein, the term "anti-TL" refers to an antibody or a fragment, derivative, or biological equivalent thereof that recognizes and binds to TL. Anti-TL may be recombinantly expressed, generated by exposing antibody producing cells to TL, or other means known in the art, using for example, the proteins described herein. Further anti-TL can be purchased from commercial vendors.

As used herein, the term "IL-2" or "IL2" or "Interleukin 2" refers to a cytokine known for function in immune tolerance and immunity and understood to be involved in the body's response to microbial infection. Non-limiting exemplary amino acid sequences of IL-2 can be found in the Uniprot database under accession numbers P60568 (human IL-2) and P04351 (murine IL-2); other homologs of the same may also be found in the Uniprot database, i.e., at www.uniprot.org. IL-2 can be produced in vivo and isolated or in vitro, e.g., using a recombinant expression system and/or IL-2 producing cell line. Alternatively, it may be purchased through a variety of commercially available sources, e.g., Thermo-Fisher, Sigma Aldrich, and a variety of other commercial vendors of biological products.

As used herein, the term "IL-4" or "IL4" or "Interleukin 4" refers to a cytokine known for function in activation of B-cells and other cell types, as well as a costimulator of DNA-synthesis, an inducer of MHC class II expression on resting B-cells, and an effector/regulator of IgE and CD23 expression. Non-limiting exemplary amino acid sequences of IL-4 can be found in the Uniprot database under accession numbers P05112 (human IL-4) and P07750 (murine IL-4); other homologs of the same may also be found in the Uniprot database, i.e., at www.uniprot.org. IL-4 can be produced in vivo and isolated or in vitro, e.g., using a recombinant expression system and/or IL-4 producing cell line. Alternatively, it may be purchased through a variety of commercially available sources, e.g., Thermo-Fisher, Sigma Aldrich, and a variety of other commercial vendors of biological products.

As used herein, the term "anti-IL-4" refers to an antibody or a fragment, derivative, or biological equivalent thereof that recognizes and binds to IL-4. Anti-IL-4 may be recombinantly expressed, generated by exposing antibody producing cells to IL-4, or other means known in the art, using for example, the proteins described herein. Further anti-IL-4 can be purchased from commercial vendors, such as but not limited to those listed above with respect to IL-4.

As used herein, the term "IL-7" or "IL7" or "Interleukin 7" refers to a hematopoetic growth factor and cytokine that functions in B-cell and T-cell development. Non-limiting exemplary amino acid sequences of IL-7 can be found in the Uniprot database under accession numbers P13232 (human IL-7) and P10168 (murine IL-7); other homologs of the same may also be found in the Uniprot database, i.e., at www.uniprot.org. IL-7 can be produced in vivo and isolated or in vitro, e.g., using a recombinant expression system and/or IL-7 producing cell line. Alternatively, it may be purchased through a variety of commercially available sources, e.g., Thermo-Fisher, Miltenyi, and a variety of other commercial vendors of biological products.

As used herein, the term "IL-15" or "IL15" or "Interleukin 15" refers to an IL-2-like cytokine which is known to induce cell proliferation of natural killer cells. Non-limiting exemplary amino acid sequences of IL-15 can be found in the Uniprot database under accession numbers Q8NEV9 P40933 (human IL-15) and P48346 (murine IL-15); other homologs of the same may also be found in the Uniprot database, i.e., at www.uniprot.org. IL-15 can be produced in vivo and isolated or in vitro, e.g., using a recombinant expression system and/or IL-15 producing cell line. Alternatively, it may be purchased through a variety of commercially available sources, e.g., Thermo-Fisher, Miltenyi, and a variety of other commercial vendors of biological products.

As used herein, the term "CD28" refers to all isoforms of a protein known to provide a co-stimulator signal for T-cell stimulation, sometimes referred to as "Cluster of Differentiation 28" or "T44," or a fragment or biological equivalent thereof. Non-limiting exemplary amino acid sequences of CD28 can be found in the Uniprot database under accession numbers P10747 (human CD28); Q9GKP3 (canine CD28); Q00609 (murine CD28); other homologs of the same may also be found in the Uniprot database, i.e., at www.uniprot.org. CD28 can be produced in vivo and isolated or in vitro, e.g., using a recombinant expression system and/or CD28 producing cell line. Alternatively, it may be purchased through a variety of commercially available sources, e.g., Thermo-Fisher, R&D Systems, Abcam, Adipogen, and a variety of other commercial vendors of biological products.

As used herein, the term "anti-CD28" refers to an antibody or a fragment, derivative, or biological equivalent thereof that recognizes and binds to CD28. Anti-CD28 may be recombinantly expressed, generated by exposing antibody producing cells to CD28, or other means known in the art, using for example, the proteins described herein. Further anti-CD28 can be purchased from commercial vendors, such as but not limited to those listed above with respect to CD28.

As used herein, the term "CD3" refers to all isoforms of a protein known to be a surface marker of T-cells, i.e., T-cell co-receptor, which is required for T-cell activation, sometimes referred to as "Cluster of Differentiation 3" or "T3 complex," or a fragment or biological equivalent thereof. Generally, CD3 is composed of four distinct polypeptide chains; epsilon (ε), gamma (γ), delta (δ) and zeta (ζ), that assemble and function as three pairs of dimers (εγ, εδ, ζζ). Non-limiting exemplary amino acid sequences of CD3 can be found in the Uniprot database under accession numbers P07766 (human CD3 epsilon chain), P09693 (human CD3 gamma chain), P04234 (human CD3 delta chain), P20963 (human CD3 zeta chain); P22646 (murine CD3 epsilon chain), P11942 (murine CD3 gamma chain), P04235 (murine CD3 delta chain), P24161 (murine CD3 zeta chain); Q95LI5 (simian CD3 epsilon chain), Q28074 (bovine CD3 gamma chain), Q95LI8 (simian CD3 delta chain), Q9XSJ9 (porcine CD3 zeta chain); other homologs of the same may also be found in the Uniprot database, i.e., at www.uniprot.org. CD3 can be produced in vivo and isolated or in vitro, e.g., using a recombinant expression system and/or CD3 producing cell line. Alternatively, it may be purchased through a variety of commercially available sources, e.g., Thermo-Fisher and a variety of other commercial vendors of biological products.

As used herein, the term "anti-CD3" refers to an antibody or a fragment, derivative, or biological equivalent thereof that recognizes and binds to CD3. Anti-CD3 may be recombinantly expressed, generated by exposing antibody producing cells to CD3, or other means known in the art, using for example, the proteins described above. Further anti-CD3 can be purchased from commercial vendors, such as but not limited to those listed above with respect to CD3.

As used herein, the term "IFNγ" or "interferon gamma" or "IFNg" refers to a soluble cytokine and the only member of the type II class of interferons. Non-limiting exemplary amino acid sequences of IFNγ can be found in the Uniprot database under accession numbers P01579 (human IFNγ) and P01580 (murine IFNγ); other homologs of the same may also be found in the Uniprot database, i.e., at www.uniprot.org. IFNγ can be produced in vivo and isolated or in vitro, e.g., using a recombinant expression system and/or IFNγ producing cell line. Alternatively, it may be purchased through a variety of commercially available sources, e.g., Thermo-Fisher, Sigma Aldrich, and a variety of other commercial vendors of biological products.

As used herein, "Lag3" or "lymphocyte-activation gene 3" or "CD223" or "cluster of differentiation 223" is a protein that is encoded by the Lag3 gene and belongs to the immunoglobulin (Ig) superfamily. Lag 3 is a cell surface protein that is expressed in a variety of cell types, including T-cells, natural killer cells, B cells, and plasmacytoid dendritic cells. Non-limiting exemplary amino acid sequences for Lag3 can be found in the Uniprot database under accession numbers P18627 (human Lag3) and Q61790 (murine Lag3); other homologs of the same may also be found in the Uniprot database, i.e., at www.uniprot.org. Detection of a cell expressing Lag3 can be identified using conventional techniques, such as the use of an anti-Lag3 antibody, which are commercially available, e.g., from a vendor such as BioLegend.

As used herein, "PD-1" or "programmed cell death protein 1" or "CD279" or "cluster of differentiation 279" is a protein that is encoded by the PD-1 gene and is a cell surface receptor belonging to the immunoglobulin (Ig) superfamily that plays a role in down-regulating immune functions, promoting self-tolerance, suppressing T-cell inflammatory activity, suppressing apoptosis by antigen specific T-cells in the lymph nodes, and reducing apoptosis of T-regs. PD-1 binds PD-L1 and PD-L2. Due to its immune regulatory function, PD-1 is often referred to as an immune checkpoint. Non-limiting exemplary amino acid sequences for PD-I can be found in the Uniprot database under accession numbers Q15116 (human PD-1), Q02242 (murine PD-1), U6CTF8 (mink PD-1); other homologs of the same may also be found in the Uniprot database, i.e., at www.uniprot.org. Detection of a cell expressing PD-1 can be identified using conventional techniques, such as the use of an anti-PD-1 antibody, which are commercially available, e.g., from a vendor such as Abcam.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement.

Applicants have provided herein the polypeptide and/or polynucleotide sequences for use in gene and protein transfer and expression techniques described below. It should be understood, although not always explicitly stated that the sequences provided herein can be used to provide the expression product as well as substantially identical sequences that produce a protein that has the same biological properties. These "biologically equivalent" or "biologically active" polypeptides are encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions. Specific polypeptide sequences are provided as examples of particular embodiments. Modifications to the sequences to amino acids with alternate amino acids that have similar charge. Additionally, an equivalent polynucleotide is one that hybridizes under stringent conditions to the reference polynucleotide or its complement. Alternatively, an equivalent polypeptide or protein is one that is expressed from an equivalent polynucleotide.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PC reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10× SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample; further, the expression level of multiple genes can be determined to establish an expression profile for a particular sample. The terms "upregulate" and "downregulate" and variations thereof when used in context of gene expression, respectively, refer to the increase and decrease of gene expression relative to a normal or expected threshold expression for cells, in general, or the sub-type of cell, in particular.

Modes of Carrying Out the Disclosure

The present disclosure relates to particular subsets of CD4+ and CD8+ T-cells, methods of isolating and generating these cells, compositions comprising these cells, and methods of treatment of a tumor or cancer by administering these cells alone or in combination with other therapies.

Aspects of this disclosure relate to a method of generating a population of tumor-specific CD4+ cytotoxic T-cells the method comprising, or alternatively consisting essentially of, or yet further consisting of, contacting a population of tumor-specific CD4+ T-cells with an effective amount of a combination comprising retinoic acid, TGF-β, and IL-27, thereby generating tumor-specific CD4+ cytotoxic T-cells. In some embodiments, the retinoic acid, the TGF-β, and the IL-27 of the combination are administered concurrently or sequentially. In some embodiments, the combination or one or more components thereof are administered to the population of tumor-specific CD4+ T-cells more than once, e.g., twice or thrice or more often as desired. In some embodiments, the combination comprising retinoic acid, TGF-β, and IL-27 comprises greater than about 5 ng/mL, less than about 25 ng/mL, or between about 5 ng/mL to about 25 ng/mL of I1-27; greater than, less than, or about 5 ng/mL or between about 2 ng/mL to about 10 ng/mL of TGF-β, and/or greater than about 100 nM, less than about 500 nM, or between about 100 nM to about 500 nM of retinoic acid, and concentrations within these ranges. In some embodiments, the aforementioned combination comprising retinoic acid, TGF-β, and IL-27 further comprises acetate and/or anti-IL-4.

The CD4+ cytotoxic T-cells prepared by the methods disclosed herein express CD4 on their surface and, are ThPOK$^-$ (downregulated). These CD4+ cytotoxic T-cells can also be characterized by CD8αα expression (having both CD8αα+ and CD8αα- subsets), downregulation of Gata3, and upregulation of Runx3 (in some subsets) and Tbet (in some subsets). CD4+ cytotoxic T-cells are also generally PD-1- (negative) and Lag3-(negative). The cells and/or populations of cells can be labeled (e.g., detectably labeled) for ease of purification or monitoring of the cells and/or populations.

In some embodiments, the population of tumor-specific CD4+ T-cells used as the source of cells for the method comprises one or more of naïve CD4+ T-cells, double-negative T-cells, Th1 T-cells, Th17 T-cells, and T-regulatory cells.

In some embodiments, the method further comprises contacting a population of tumor-specific CD4+ T-cells with an effective amount of anti-CD28 antibody, fragment or equivalent thereof and/or anti-CD3 antibody, fragment or equivalent thereof. In some embodiments, the anti-CD3 antibody, fragment or equivalent thereof is bound to a plate on which the population of tumor-specific CD4+ T-cells are plated. In further embodiments, the method further comprises contacting a population of tumor-specific CD4+ T-cells with an antigen, e.g., a tumor antigen. In further embodiments, the anti-CD28 antibody, fragment or equivalent thereof, optional antigen, and the combination comprising retinoic acid, TGF-β, and IL-27 are administered simultaneously or sequentially. In some embodiments, anti-CD28 antibody, fragment or equivalent thereof and, optionally, the antigen are administered once. In embodiments involving multiple administrations of the combination comprising retinoic acid, TGF-β, and IL-27, anti-CD28 antibody, fragment or equivalent thereof and/or anti-CD3 antibody, fragment or equivalent thereof and, optionally, the antigen are administered once, optionally concurrently or sequentially with the first administration of the combination comprising retinoic acid, TGF-β, and IL-27. In some embodiments, the anti-CD28 antibody, fragment or equivalent thereof is at a concentration greater than about 0.5 µg/mL, less than about 2 µg/mL, or between about 0.5 µg/mL and about 2 µg/mL, and concentration ranges in between. All the indicated concentrations are the final concentrations in solution. In some embodiments, anti-CD3 antibody, fragment or equivalent thereof and, optionally, the antigen is administered once.

In embodiments involving multiple administrations of the combination comprising retinoic acid, TGF-β, and IL-27, anti-CD3 antibody, fragment or equivalent thereof is administered more than once, e.g., twice or thrice or multiple times thereafter as necessary, optionally concurrently or sequentially with the administration of the combination comprising retinoic acid, TGF-β, and IL-27. In some embodiments, the anti-CD3 is at a concentration of greater than about 1 µg/mL, less than about 2 µg/mL, or between about 1 µg/mL and about 2 µg/mL, and concentration ranges in between. All the indicated concentrations are the final concentrations in solution.

In some embodiments, the method further comprises, or consists essentially of, or yet further consists of, contacting a population of tumor-specific CD4+ T-cells with an effective amount of IL-15, a fragment or an equivalent thereof. In some embodiments, IL-15 is at a concentration of about 50 ng/mL. As noted above, all concentrations are the final concentrations in solution. This may occur before or after generation of the tumor-specific CD4+ cytotoxic T-cells. In some embodiments, IL-15 is administered once. In embodiments involving multiple administrations of the combination comprising retinoic acid, TGF-β, and IL-27, IL-15 is administered, optionally concurrently or sequentially, with the final administration of the combination comprising retinoic acid, TGF-β, and IL-27.

In some embodiments, the population of tumor-specific CD4+ T-cells is isolated from an in vitro culture system comprising a tumor or tumor cell-line and a population comprising naïve and/or effector T-cells. In further embodiments, the population comprising naïve and/or effector T-cells is cultured in the presence of a tumor or tumor cell-line. In still further embodiments, the tumor or portion thereof has been surgically removed from an animal having a tumor or cancer or a fragment of the tumor, e.g., a tumor biopsy. In other embodiments, the population of tumor-specific CD4+ T-cells is isolated from a biological sample from an animal having a tumor that has been cultured or preserved. In further embodiments, the biological sample is a fluid sample from the microenvironment surrounding the tumor. In other embodiments, the biological sample is blood or peripheral blood mononuclear cells. In some embodiments, the animal is a human patient diagnosed with cancer.

Further aspects relate to a population of tumor-specific CD4+ cytotoxic T-cells prepared by the method disclosed herein. The CD4+ cytotoxic T-cells prepared by the methods disclosed herein express CD4 on their surface and, are ThPOK⁻ (downregulated) (conversely to naïve CD4+ T-cells which express THPOK). These CD4+ cytoxic T-cells can also be characterized by CD8αα expression (having both CD8αα+ and CD8αα- subsets), downregulation of Gata3, and upregulation of Runx3 (in some subsets) and Tbet (in some subsets). CD4+ cytotoxic T-cells are also generally PD-1− and Lag3−. Naïve CD4 T-cells do not express those molecules.

Still further aspects relate to a composition comprising the populations as described herein and a carrier. In further embodiments, the composition comprises an effective amount of (i) a population of immune cells comprising one or more of CD8+ T-cells (optionally CD8αα+ T-cells), double-negative T-cells (CD3+, CD4−, CD8−), and NK T-cells and/or (ii) IFNγ. In some embodiments, the carrier is a pharmaceutically acceptable carrier. In further aspect, the composition can comprise a cryoprotectant and/or preservative for the cells.

Still further aspects relate to a method of treating a tumor or cancer, and/or augmenting an immune response in a subject in need thereof, the method comprising, or alternatively consisting essentially of, or yet further consisting of, administering an effective amount of a population or composition as disclosed herein to the subject, thereby treating the tumor or the cancer or augmenting an immune response. In some embodiments, the method comprises, or alternatively consists essentially of, or yet further consists of, administering in sequence (a) an effective amount of (i) a population of immune cells comprising one or more of CD8+ T-cells (optionally CD8αα+ T-cells), double-negative T-cells (CD3+, CD4−, CD8−), and NK T-cells and/or (ii) IFNγ and (b) a population of tumor-specific CD4+ cytotoxic T-cells or a composition comprising said population.

In further embodiments, the method comprises or alternatively consists essentially of, or yet further consists of, administering one or more cytoreductive therapy and/or immunotherapy. In some embodiments, the subject is a mammal, optionally a canine, feline, or a human patient and the cells are species-specific to the subject being treated, and can further be autologous or allogeneic to the subject.

Also provided is a kit for generating and expanding a population of tumor-specific CD4+ cytotoxic T-cells, optionally, comprising retinoic acid, TGF-β, and IL-27, and instructions for use. In some embodiments, the kit further comprises acetate and/or anti-IL-4.

Aspects of this disclosure relate to a method of isolating an anti-tumor CD8+ cytotoxic T-cell, the method comprising, or alternatively consisting essentially of, or yet further consisting of, contacting a population of cells suspected of comprising the anti-tumor cytotoxic CD8+ T-cell with a thymus leukemia ("TL") tetramer and isolating the T-cell bound to the TL tetramer. Also provided herein is an isolated anti-tumor CD8+ cytotoxic T-cell bound or coupled to TL tetramer. In a further aspect, the method further comprises or alternatively consists essentially of, or yet further consists of, isolating or separating the cell from the tetramer. In other embodiments, the tetramer may be internalized and degraded and/or may separate from the cell without a further method step. In some embodiments, the method yet further comprises or alternatively consists essentially of, or yet further consists of, culturing the anti-tumor CD8+ cytotoxic T-cells under conditions for expansion of the anti-tumor CD8+ cytotoxic T-cell to a clonal population, thereby generating a clonal population of the anti-tumor CD8+ cytotoxic T-cells. In some embodiments, the method yet further comprises or alternatively consists essentially of, or yet further consists of, modifying the anti-tumor CD8+ cytotoxic T-cells to express an engineered T-cell receptor, such as a chimeric antigen receptor, on the cell surface. The resulting anti-tumor CD8+ cytotoxic T-cells—whether isolated, yet further expanded, and/or yet further engineered—have diagnostic, prognostic and therapeutic uses as described herein. Not to be bound by theory, it is believed that the population of anti-tumor CD8+ cytotoxic T-cells generated by the methods described herein have superior anti-tumor activity than other populations of T-cells.

The population of cells suspected of comprising the anti-tumor cytotoxic CD8+ T-cell comprises CD8+ T-cells. The anti-tumor cytotoxic CD8+ T-cell is a cytotoxic T-cell and/or a precursor thereof which is CD8+ and expresses CD8αα on its surface.

In some embodiments, the population of cells suspected of comprising the anti-tumor cytotoxic CD8+ T-cell has been exposed to a tumor or a tumor antigen in vivo or in vitro. In some embodiments, the population of cells suspected of comprising the anti-tumor cytotoxic CD8+ T-cell has been exposed to a tumor or a tumor antigen in vitro. In further embodiments, the exposure of the population of cells suspected of comprising the anti-tumor cytotoxic CD8+ T-cell comprises or alternatively consists essentially of, or yet further consists of, contacting the population of cells suspected of comprising the anti-tumor cytotoxic CD8+ T-cell with a tumor or antigen, e.g., a tumor antigen. Tumor antigens are known in the art, and include those categorized as lineage-restricted (usually expressed by a single cancer histotype), mutated (only expressed because of a mutation or alteration in transcription caused by cancer), posttranslationally altered, idiotypic (polymorphic, resulting from clonal aberrances), oncofetal (those typically expressed in fetal tissues and in cancerous somatic cells), oncoviral (encoded by tumorigenic, transforming viruses), overexpressed/accumulated (expressed by both normal and neoplastic tissue, but overexpressed in a cancer or tumor), or cancer-testis (expressed only by cancer cells and reproductive tissues, e.g., testis and placenta).

In some embodiments, the population of cells suspected of comprising the anti-tumor cytotoxic CD8+ T-cell is a purified population comprising only CD8+ T-cells. In some embodiments, the population of cells suspected of comprising the anti-tumor cytotoxic CD8+ T-cell is a population comprising or consisting essentially of $CD8+C_{44}^{low}$ T-cells.

In some embodiments, the population of cells suspected of comprising the anti-tumor cytotoxic CD8+ T-cell is from a commercially available source. In some embodiments, the population of cells suspected of comprising the anti-tumor cytotoxic CD8+ T-cell is from an in vitro culture system comprising a tumor or tumor cell-line and a population comprising naïve and/or effector T-cells. In further embodiments, the tumor is a tumor or tumor specimen surgically removed from an animal having a tumor or cancer or a fragment portion) thereof, e.g., a tumor biopsy. In other embodiments, the population of cells suspected of comprising the anti-tumor cytotoxic CD8+ T-cell is from a biological sample from an animal having a tumor. In further embodiments, the biological sample is a biological or fluid sample from the microenvironment surrounding the tumor. In some embodiments, the population of cells suspected of comprising the anti-tumor cytotoxic CD8+ T-cell are from an animal, optionally a mammal such as but not limited to a human patient diagnosed with a cancer. Non-limiting examples of such cancers include leukemia and cancers that produce solid tumors. In some embodiments, the population of cells suspected of comprising the cytotoxic CD8+ T-cell are isolated from the animal by a method comprising FACS or magnetic bead based sorting of the cells from a biological sample isolated from the animal.

In some embodiments, the cytotoxic CD8+ T-cell is isolated from the population of cells suspected of comprising the cytotoxic CD8+ T-cell produced by the methods of this disclosure is by a method comprising FACS or magnetic bead based sorting of the cells.

In some embodiments, the isolated cytotoxic T-cells are expanded to a substantially (greater than about 80% homogenous) population of cells or a clonal population. To expand the cells, the isolated cell or cells are cultured in an effective culture medium, such as but not limited to RPMI and DMEM, supplemented with an effective amount of one or more of BSA, L-glutamine, pen/strep, amino acids, and a cytokine, such as but not limited to IL-2, IL-7, IL-15, and IFNγ, for an appropriate amount of time and at an appropriate temperature. Also provided is the clonal and/or substantially homogeneous population of cells prepared by this method. The population can be at least 80% homogeneous, or at least 85%, or at least 90%, or at least 95%, homogeneous.

Further aspects of the disclosure relate to a population of anti-tumor CD8+ cytotoxic T-cells prepared by the methods disclosed herein, i.e., anti-tumor CD8+ cytotoxic T-cells that bind to a TL tetramer. Still further aspects relate to a composition comprising one or more of: the anti-tumor CD8+ cytotoxic T-cell bound to the TL tetramer; the isolated anti-tumor CD8+ cytotoxic T-cell; and the clonal population of anti-tumor CD8+ cytotoxic T-cells, and a carrier, optionally a pharmaceutically acceptable carrier. In one aspect, the one or more anti-tumor CD8+ cytotoxic T-cell bound to the TL tetramer; the isolated anti-tumor CD8+ cytotoxic T-cell; the substantially homogeneous; and the clonal population of anti-tumor CD8+ cytotoxic T-cells, are present in the composition in a therapeutically effective amount. In some embodiments, the composition further comprises or alternatively consists essentially of one or more of CD4+ cytotoxic T-cells and an immune checkpoint inhibitor, that also can be present in a therapeutically effective amount.

The compositions and cells as described herein are useful therapeutically. In one embodiment, a method of one or more of: treating a cancer, inhibiting the growth of a tumor or a cancer cell or reducing metastasis of the cancer or tumor cell is provided, the method comprising, or alternatively consisting essentially of, or yet further consisting of, contacting the cancer or tumor cell with an effective amount of any one of the population or composition disclosed herein. In some embodiments, the method further comprises measuring the growth inhibition of the tumor or cancer cell after contacting has occurred. In some embodiments, the contacting is in vitro or in vivo. The cells, populations and/or compositions can be detectably or otherwise labeled for ease of isolation and/or diagnostic use.

Additional aspects relate to a method of treating a tumor or cancer or eliciting an anti-tumor immune response in a subject in need thereof, the method comprising, or alternatively consisting essentially of, or yet further consisting of, administering an effective amount of any one of the population, substantially homogeneous population of cells, clonal population, or composition disclosed herein. In some embodiments, the method further comprises or alternatively consists essentially of, or yet further consists of, administering an effective amount of one or more cytoreductive therapy and/or immunotherapy to the subject. In some embodiments, the method comprises contacting a cancer or tumor cell isolated from the subject with an effective amount of the therapy, and assaying for the growth inhibition effect of the cell population or the compositions, prior to administration of the cell populations or compositions to the subject. In some embodiments, the method comprises assaying for the therapeutic effect of the therapy, after administration of the therapy to the subject. The subject can be any animal, e.g., a mammal such as a human subject.

In some embodiments, the species of the cell population or composition is identical to the subject being treated. In some embodiments, the cells are autologous or allogenic to the subject being treated. In some embodiments, the therapy is administered as a first-line therapy, a second-line therapy, a third-line therapy, a fourth-line therapy and or a fifth line-therapy. Modes of administration are known in the art and briefly described herein.

Still further aspects relate to diagnostic methods using a TL tetramer. For example, provided herein is a method of selecting a treatment for a tumor or cancer in a subject in need thereof, comprising: administering a plurality of detectably labeled TL tetramers to the subject, detecting the TL tetramers in the subject to determine the concentration of anti-tumor CD8+ cytotoxic T-cells, and selecting the appropriate cytoreductive and/or immunotherapy from the measured concentration of the cells detected. In some method aspects, the subject is a mammal, optionally a canine, equine, feline, or a human patient.

Also provided is a kit for generating, detecting and expanding a population of high affinity anti-tumor CD8+ cytotoxic T-cells generated according the method of isolation described herein comprising a TL tetramer and instructions for use.

I. Compositions and Methods for the Generation of Tumor-Specific CD4+ Cytotoxic T-Cells The present disclosure is based on the concept that T-reg, including tumor-specific T-regs, or other CD4 T helper cells can be reprogrammed from regulatory or T helper cells to killer cells under certain conditions and this plasticity represents a strategy to promote tumor specific CD4+ cytotoxic cell-mediated cancer killing. The combination of retinoic acid, TGF-β, and IL-27 or "RABI27" technology disclosed herein can transform T-regs, including anti-tumor specific CD4+ T-regs, or other CD4+ T helper cells into tumor-specific cytotoxic T-cells and represents a new approach over current therapeutic strategies that aim to target CD8+ T-cell mediated cancer killing. Furthermore, the conversion of anti-tumor CD4+ Treg or other CD4+ T helper cells to cytolytic cells prevents the anti-suppressive response of tumor-specific Tregs without modifying the Treg function of other Treg cells. Using a murine melanoma model, Applicant has demonstrated that tumor-specific CD4+ T helper cells can be isolated, reprogrammed ex vivo into anti-tumor killer cells and administered into tumor bearing mice to enable effective cancer killing. Additionally, the ability to isolate T-regs from tumor tissue and transform them into tumor-specific cytotoxic T-cell killers represents a major advancement towards a dual functioning therapy that simultaneously reduces tumor-mediated immune suppression and promotes tumor-specific killing. Furthermore, RABI27 can be combined with other cancer immunotherapies to effectuate a broader anti-cancer response, including the treatment with TL-tetramer detected and expanded high affinity anti-tumor CD8 effector T-cell therapy. Anti-tumor CD4+ cytotoxic cells from patients or derived from commercially available sources can be stored and administered during the occurrence or re-occurrence of cancer.

The initial lineage commitment to either CD4 or CD8 fate is made in the thymus during T-cells development. CD4+ CD8+ thymocytes with TCRs that interact with MHC II molecules differentiate into CD4+ T helper-cells, whereas ones that recognize MHC I molecules differentiate into CD8+ cytotoxic T-cells. This lineage commitment is also regulated by specific transcription factors. For example, GATA3 and ThPOK promote CD4+T helper fate, whereas Runx3 mediates the CD8+ CTL fate. Notably, GATA3 and ThPOK can modify Runx3 expression.

Applicant conducted a number of studies to understand CD4+ cell fates, and discovered that mature ThPOK-expressing CD4 T helper cells can reprogram to ThPOK negative but Runx3 positive CD4 CTL in the periphery Mucida et al. (2013) Nat. Immunol. 14(3):281-289, Reis et al. (2013) Nat. Immunol. 14(3):271-280. Specifically, in ThPOK$^{GFP}$ reporter mice it is expected that in a spleen or mLn CD4+ T helper cells express the master transcription factor, ThPOK whereas cytotoxic CD8+ T-cells express the CTL transcription factor, Runx3, instead. Applicant made a surprising observation that in the intestine a large fraction of CD4+ T helper cells do not express Thpok but instead express Runx3 and CD8α proteins, indicating that ThPOK negative CD4 T-cells might be CTL. Furthermore, the Applicant found that mice expressing a monoclonal population of OVA-specific CD4 T helper cells (OT II-TCR transgenic mice) exposed to OVA antigen in their diet, generated large numbers of OT-II CD4 T-cells that lost ThPOK expression but gained Runx3 expression instead. Together with the Runx3 expression these OVA-reactive CD4 T-cells reprogrammed to cytotoxic effector cells. Based on this finding, the Applicant concluded that reprogramming of CD4+ T helper-cells is driven by repeated exposure to their cognate antigen under non-inflammatory conditions. These reprogrammed ThPOK⁻ CD4+ T-cells are cytotoxic but, unlike cytotoxic CD8+ cells, they are not suppressed by Tregs.

Applicant further determined that after 1 week preparation by the methods, 5 to 30% of CD4+ cells express CD8αα. All the CD4+ cytotoxic T-cells lost ThPOK. In line with ThPOK downregulation, all the CD4+ cytotoxic T-cells lost Gata3; 30 to 80% of CD4+ T cells expressed Tbet; and 40 to 60% of the Tbet+CD4+ cells expressed Runx3.

Not to be bound by theory, since Tregs infiltrate tumors, it is suspected that tumor infiltrating Tregs must be tumor antigen-specific. Furthermore, it means tumors that are infiltrated by Tregs express MHC class II. Accordingly, strategically differentiating tumor-specific CD4+ T-cells such as tumor-infiltrating Tregs into CD4+ CTL provides a unique approach for treating cancer, effectively "turning bad into good."

Interestingly, Tregs reprogram into cytotoxic CD4+ T-cells in vivo in the intestine at steady state; thus, such strategic programing may be possible both in vitro and in vivo.

Methods of Generation of Cytotoxic CD4+ Cells

Aspects of this disclosure relate to a method of generating a population of tumor-specific CD4+ cytotoxic T-cells comprising, or alternatively consisting essentially of, or yet further consisting of, contacting a population of tumor-specific CD4+ T-cells with an effective amount of a combination comprising retinoic acid, TGF-β, and IL-27, thereby generating tumor-specific CD4+ cytotoxic T-cells. In some embodiments, the combination further comprises acetate and/or anti-IL-4.

The CD4+ cytotoxic T-cells prepared by the methods disclosed herein express CD4 on their surface and, generally, are ThPOK⁻ (downregulated). These CD4+ cytoxic T-cells can also be characterized by CD8αα expression, downregulation of Gata3, and upregulation of Runx3 and Tbet. CD4+ cytotoxic T-cells are also generally PD-1– and Lag3–. The CD4+ T-cells from which these cells may be generated using RABI27 express CD4 on their surface and, generally, are ThPOK+(upregulated); these cells include naïve CD4+ T-cells, Th1 T-cells, Th17 T-cells, and T-regulatory cells.

As is apparent to the skilled artisan, the cells and combination can be cultured in combination for an appropriate amount of time and temperature to generate the CD4+ cytotoxic T-cells. In some embodiments, the retinoic acid, the TGF-β, and the IL-27 of the combination are administered concurrently or sequentially. In some embodiments, the combination or one or more components thereof is administered to the population of tumor-specific CD4+

T-cells more than once, e.g., twice or thrice or multiple times thereafter as necessary. The desired phenotype of the culture can be determined by assaying for the appropriate marker as noted above for the cytotoxic cell population. These methods are known in the art and briefly described herein.

The tumor specific CD4+ T-cells used in the method to generate the cytotoxic CD4+ T-cells, can be from any appropriate species, e.g., mammal, such as canine, feline, equine, bovine and human. In some embodiments, the tumor is a solid tumor or a circulating tumor cell, which can be benign or malignant.

In some embodiments, the method further comprises contacting a population of tumor-specific CD4+ T-cells with an effective amount of anti-CD28 antibody, fragment or equivalent thereof and/or anti-CD3 antibody, fragment or equivalent thereof. In some embodiments, the anti-CD3 antibody, fragment or equivalent thereof is bound to a plate on which the population of tumor-specific CD4+ T-cells are plated. In further embodiments, the method comprises contacting a population of tumor-specific CD4+ T-cells with an antigen, e.g., a tumor antigen. In further embodiments, the anti-CD28 antibody, fragment or equivalent thereof, optional antigen, and the combination comprising retinoic acid, TGF-β, and IL-27 are administered concurrently or sequentially. In some embodiments, anti-CD28 antibody, fragment or equivalent thereof and, optionally, the antigen is administered once. In embodiments involving multiple administrations of the combination comprising retinoic acid, TGF-β, and IL-27, anti-CD28 antibody, fragment or equivalent thereof and, optionally, the antigen is administered once, optionally concurrently or sequentially with the first administration of the combination comprising retinoic acid, TGF-β, and IL-27. In some embodiments, the anti-CD28 antibody, fragment or equivalent thereof is at a concentration greater than about 0.5 µg/mL, less than about 2 µg/mL, or between about 0.5 µg/mL and about 2 µg/mL, and concentration ranges in between. In some embodiments, anti-CD3 antibody, fragment or equivalent thereof is administered once or with the same frequency as the combination comprising retinoic acid, TGF-β, and IL-27. In embodiments involving multiple administrations of the combination comprising retinoic acid, TGF-β, and IL-27, anti-CD3 antibody, fragment or equivalent thereof is administered more than once, e.g., twice or thrice or multiple times thereafter as necessary, optionally concurrently or sequentially with the administration of the combination comprising retinoic acid, TGF-β, and IL-27. In some embodiments, the anti-CD3 is at a concentration of greater than about 1 µg/mL, less than about 2 µg/mL, or between about 1 µg/mL and about 2 µg/mL, and concentration ranges in between.

In some embodiments, the method further comprises contacting a population of tumor-specific CD4+ T-cells with an effective amount of IL-15, fragment or equivalent thereof. In some embodiments, the IL-15 is at a final concentration in solution of 50 ng/mL. This may occur before or after generation of the tumor-specific CD4+ cytotoxic T-cells. In some embodiments, IL-15 is administered once. In embodiments involving multiple administrations of the combination comprising retinoic acid, TGF-β, and IL-27, IL-15 is administered, optionally concurrently or sequentially, with the final administration of the combination comprising retinoic acid, TGF-β, and IL-27.

In some embodiments, the combination comprises greater than about 5 ng/mL, less than about 25 ng/mL, or between about 5 ng/mL to about 25 ng/mL of Il-27; greater than, less than, or about 5 ng/mL or between about 2 ng/mL to about 10 ng/mL of TGF-β, and/or greater than about 100 nM, less than about 500 nM, or between about 100 nM to about 500 nM of retinoic acid, and concentration ranges in between.

Isolation of Cells

Methods for isolating a population of tumor-specific CD4+ T-cells are well known in the art.

In some embodiments, the population of tumor-specific CD4+ T-cells used for the methods comprises, or alternatively consists essentially of, or yet further consists of one or more of naïve CD4+ T-cells, Th1 T-cells, Th17 T-cells, and T-regulatory cells. The population can be purified, substantially homogeneous or heterogeneous. These cell types can be identified by their expression or lack of expression of identifying markers. Non-limiting examples of CD4+ T-cell types and markers by which they may be identified are provided herein, e.g., T-regulatory cells or Tregs (CD25+), Th1 cells (CDCR3+, CCR5+), Th2 cells (CXCR4+, CCR3+, CCR4+, CCR5+, CCR7+, CD30+), Th17 cells (CD4+, IL-17A+), and naïve CD4+ T-cells (CD4+, CD45RA+, CD62L+). Thus, conventional methods of immunoselection are suitable for the isolation of these cells. Non-limiting examples of immunoselection include but are not limited to flow cytometry, culture selection, and ELISA (enzyme linked immunosorbent assay), and variations thereof, known in the art.

In some embodiments, the population of tumor-specific CD4+ T-cells is isolated from an in vitro culture system comprising a tumor or tumor cell-line and a population comprising naïve and/or effector T-cells. In further embodiments, the cells are isolated from a tumor, and the tumor has been surgically removed from an animal cancer, e.g., a tumor biopsy. The tumor can be benign or malignant. In other embodiments, the population of tumor-specific CD4+ T-regulatory cells is isolated from a biological sample from an animal having a tumor such as blood, peripheral blood lymphocyte, lymph node or other appropriate biological sample. In further embodiments, the biological sample is a fluid sample from the microenvironment surrounding the tumor. In some embodiments, the animal is a human patient diagnosed with cancer. In some embodiments, the cancer is benign or malignant, optionally primary metastatic cancer. In some embodiments, the tumor is a solid tumor or a circulating tumor cell, which can be benign or malignant. The animal can be a mammal, such as a canine, equine, feline, bovine and human patient.

The compositions are contacted with the combination and optional combinations for an effective amount of time and under conditions such that the cytotoxic CD4+ cells are converted from the naïve cells. Cell culture techniques as well as methods to determine the presence of cytotoxic CD4+ cells are known in the art and briefly described herein. The cytotoxic CD4+ cells can be isolated from the culture and combined with appropriate carriers for therapy, e.g., a pharmaceutically acceptable carrier or other stabilizers and preservatives (e.g., glycerol) for preservation until needed for therapy. Alternatively, the cytotoxic CD4+ cells can be isolated from the culture and frozen down until needed in case of reappearance of the cancer.

Further aspects relate to populations of tumor-specific CD4+ cytotoxic T-cells prepared by the methods disclosed herein. These cells may optionally be isolated using immunoselection or genetic characterization. These cells generally express CD4 and CD8αα on the cell surface and have downregulated ThPOK and Gata3 expression and upregulated Tbet and Runx3 expression. These cells are also PD-1− and Lag3−.

Compositions, Methods, and Kits

Still further aspects relate to compositions comprising, or alternatively consisting essentially of, or yet further consisting of, this population of tumor-specific CD4+ cytotoxic T-cells, e.g., those prepared according to the method disclosed herein, and a carrier. In general, the CD4+ cytotoxic T-cells express CD4 on their surface and, are ThPOK− (downregulated). The CD4+ cytotoxic T-cells are also PD-1− and Lag3−. These CD4+ cytoxic T-cells can also be characterized by CD8αα expression, downregulation of Gata3, and upregulation of Runx3 and Tbet. Expression of transcription factors, e.g., ThPOK, Gata3, Runx3, and Tbet, may be detected using antibodies thereto and may also be detected, although alternate methods such as qPCR, protein tagging, or other means of detecting protein expression, as appropriate. The sequences for each of these transcription factors are known in the art—for example, both ThPOK is described by sequence and function under the following reference numbers GCID: GC01P15500, HGNC: 18668, Entrez Gene: 51043, Ensembl: ENSG00000160685, OMIM: 607646, and UniProtKB: 015156; Gata3, under GCID: GC10P008045, HGNC: 4172, Entrez Gene: 2625, Ensembl: ENSG00000107485, OMIM: 131320, and UniProtKB: P23771; Runx3, under GCID: GC01M024899, HGNC: 10473, Entrez Gene: 864, Ensembl: ENSG00000020633, OMIM: 600210, and UniProtKB: Q13761; and Tbet, under GCID: GC17P047733, HGNC: 11599, Entrez Gene: 30009, Ensembl: ENSG00000073861, OMIM: 604895, and UniProtKB: Q9UL17.

In some embodiments, the carrier is a pharmaceutically acceptable carrier.

Pharmaceutical compositions of the present invention may be administered in a manner appropriate to the disease to be treated or prevented. The quantity and frequency of administration will be determined by such factors as the condition of the patient, and the type and severity of the patient's disease, although appropriate dosages may be determined by clinical trials.

In further embodiments, the composition comprises an effective amount of (i) a population of immune cells comprising one or more of CD8+ T-cells (optionally CD8αα+ T-cells), double-negative T-cells (CD3+, CD4−, CD8−), and NK T-cells and/or (ii) IFNγ in addition to the population of cytotoxic tumor-specific CD4+ cytotoxic T-cells.

Not to be bound by theory, Applicant hypothesizes that the combination of IFNγ or an IFNγ producing cell such as but not limited to CD8+ cells or NK T-cells will upregulate MHC class II expression; thus, enhancing CD4+ cytotoxic T-cell activity. Thus, in one aspect, administration of an effective amount of the compositions of this disclosure can be used to upregulate MHC class II expression. For example, when administered alone, CD8+ T-cells attack, but eventually become restricted by PD-1, CDTLA-44, etc. However, when combined with CD4+ cytotoxic T-cells, the IFNγ production, e.g., by the CD8+ T-cells, can enhance MHC class II expression in a tumor; thus, allowing the CD4+ cytotoxic T-cells to "take over" once the CD8+ T-cells are restricted. NK T-cells and double-negative T-cells, which are innate IFNγ producers, can be used in a similar manner. In some embodiments, the CD8+ T-cells are CD8αα+ T-cells that are isolated using a TL tetramer, as disclosed herein below. In some embodiments, the NK T-cells may be alpha-galactosylceramide (a-GalCer) activated.

Still further aspects relate to a method of treating a tumor or cancer or augmenting an anti-tumor immune response in a subject in need thereof, comprising administering an effective amount of the population of CD4+ cytotoxic T-cells or composition comprising said population disclosed herein to the subject, thereby treating the tumor or the cancer. In some embodiments, said method comprises administering in sequence (a) an effective amount of (i) a population of immune cells comprising one or more of CD8+ T-cells (optionally CD8αα+ T-cells), double-negative T-cells (CD3+, CD4−, CD8−), and NK T-cells and/or (ii) IFNγ and (b) a population of tumor-specific CD4+ cytotoxic T-cells or a composition comprising said population.

In some embodiments, the subject is a mammal, optionally a canine, feline, or a human patient. In some embodiments, the cancer is benign or malignant. In some embodiments, the tumor is a solid tumor or a circulating tumor cell, which can be benign or malignant. In some embodiments, the species of the population or composition is identical to the subject being treated. In some embodiments, the cells are autologous or allogenic to the subject being treated. In some embodiments, the therapy is administered as a first-line therapy, a second-line therapy, a third-line therapy, a fourth-line therapy and or a fifth line-therapy.

In further embodiments, the method comprises administering one or more cytoreductive therapy and/or immunotherapy, optionally sequentially or concurrently with the population of CD4+ cytotoxic T-cells or composition comprising said population. In some embodiments, the immunotherapy comprises administration of one or more of CD8+ T-cells (optionally CD8αα+ T-cells), double-negative T-cells (CD3+, CD4−, CD8−), NK T-cells, and IFNγ. In further such embodiments, the one or more of CD8+ T-cells (optionally CD8αα+ T-cells), double-negative T-cells (CD3+, CD4−, CD8−), NK T-cells, and IFNγ may be administered in a manner, e.g., sequentially, or in an amount effective to enhance the MHC class II expression, as noted above. In some embodiments, this entails administering an effective amount of one or more of CD8+ T-cells (optionally CD8αα+ T-cells), double-negative T-cells (CD3+, CD4−, CD8−), NK T-cells, and IFNγ. In further such embodiments, the one or more of CD8+ T-cells (optionally CD8αα+ T-cells), double-negative T-cells (CD3+, CD4−, CD8−), NK T-cells, and IFNγ, first, and the population of CD4+ cytotoxic T-cells or composition comprising said population, second.

In some embodiments, the method comprises contacting a cancer or tumor cell isolated from the subject with an effective amount of the therapy, and assaying for the growth inhibition effect of the cell population or the compositions, prior to administration of the cell populations or compositions to the subject. In some embodiments, the method comprises assaying for the therapeutic effect of the therapy, after administration of the therapy to the subject.

One can determine if the therapy is effective by noting clinical and sub-clinical parameters such as a reduction in tumor burden or size in the subject being treated. This can be achieved by any appropriate method known in the art, e.g., by scan or immunological assay to measure tumor burden, such as but not limited to comparing pre- and post-treatment anti-CEA binding with a decrease being a positive result; determining the number of tumor-infiltrating T-cells or CD4+ T-cell activity in a subject, e.g., a human patient, with an upregulation being a positive result; measuring IL-10 response pre- and post-treatment with a reduction being a positive result. Assessing the success of such treatment can be accomplished to methods known in the art. The FDA Guidance for Industry: Clinical Trial Endpoints for the Approval of Cancer Drugs and Biologics also lists a number of exemplary endpoints such as but not limited to length of disease-free or progression-free survival, time to progression, objective response rate, and biomarker or symptom based endpoints for particular cancers. Additional endpoints include but are not limited to reduction in tumor number or tumor size.

Also provided is a kit for generating and expanding a population of tumor-specific CD4+ cytotoxic T-cells, optionally, comprising retinoic acid, TGF-β, and IL-27, and instructions for use.

II. Anti-Tumor CD8+ Cytotoxic T-cells and Methods of Isolation Thereof

In peripheral tissues there is an enrichment of $T_{REM}$ co-expressing the homodimeric CD8αα and the more common heterodimeric CD8αβ. CD8αα promotes the survival and differentiation of activated lymphocytes into memory CD8+ T-cells. Madakamutil et al. (2004) Science 304(5670): 590-593. Non-classical MHC class I thymus leukemia antigen (TL) is induced on many transformed cells, e.g., tumor cells. TL serves as a modulator of T-cell responses. Leishman et al. (2001) Science 294(5548):1936-1939. CD8αα is induced on CD8αβ+ T-cells with the strongest affinity for target antigen. It was found that activation-induced CD8αα expression on CD8αβ+ effector T-cells rescues them from TL-induced cell death (TCID) and activation induced cell death (ACID). Huang et al. (2011) Nat. Immunol. 12(11): 1086-1095. Thus, these cells represent highly effective candidates for the treatment of a tumor or cancer. Applicant has discovered that TL interacts more strongly with CD8αα than CD8αβ. Thus, TL tetramers, thus, serve as a way to identify and isolate a highly effective population of anti-tumor CD8+ cytotoxic T-cells, which express both CD8αα and CD8αβ.

Methods of Isolation

Aspects of this disclosure relate to a method of isolating an anti-tumor CD8+ cytotoxic T-cell, the method comprising, or alternatively consisting essentially of, or yet further consisting of, contacting a population of cells suspected of comprising the anti-tumor cytotoxic CD8+ T-cell with a thymus leukemia ("TL") tetramer and isolating the T-cell bound to the TL tetramer. Also provided herein is an isolated anti-tumor CD8+ cytotoxic T-cell bound or coupled to TL tetramer. In a further aspect, the method further comprises isolating or separating the cell from the tetramer. In other embodiments, the tetramer may be internalized and degraded and/or may separate from the cell without a further method step.

The population of cells suspected of comprising the anti-tumor cytotoxic CD8+ T-cell comprises CD8+ T-cells. The anti-tumor cytotoxic CD8+ T-cell is a cytotoxic T-cell and/or a precursor thereof which is CD8+ and expresses CD8αα on its surface.

In some embodiments, the cytotoxic CD8+ T-cell is isolated from the population of cells suspected of comprising the cytotoxic CD8+ T-cell by a method comprising FACS or magnetic bead based sorting of the cells from a biological sample isolated from the animal.

Sources of Cells

In some embodiments, the population of cells suspected of comprising the anti-tumor cytotoxic CD8+ T-cell has been exposed to a tumor or a tumor antigen in vitro or in vivo. In some embodiments, the population of cells suspected of comprising the anti-tumor cytotoxic CD8+ T-cell has been exposed to a tumor or a tumor antigen in vitro. In further embodiments, the exposure of the population of cells suspected of comprising the anti-tumor cytotoxic CD8+ T-cell comprises contacting the population of cells suspected of comprising the anti-tumor cytotoxic CD8+ T-cell with a tumor or tumor antigen.

In some embodiments, the population of cells suspected of comprising the anti-tumor cytotoxic CD8+ T-cell is a purified population comprising only CD8+ T-cells. In some embodiments, the population of cells suspected of comprising the anti-tumor cytotoxic CD8+ T-cell is CD8+$C_{44}^{low}$.

In some embodiments, the population of cells suspected of comprising the anti-tumor cytotoxic CD8+ T-cell is from a commercially available source. In some embodiments, the population of cells suspected of comprising the anti-tumor cytotoxic CD8+ T-cell is from an in vitro culture system comprising a tumor or tumor cell-line and a population comprising naïve and/or effector T-cells. In further embodiments, the tumor is a tumor surgically removed from an animal having a tumor or cancer or a fragment thereof, e.g., a tumor biopsy. In other embodiments, the population of cells suspected of comprising the anti-tumor cytotoxic CD8+ T-cell is from a biological sample from an animal having a tumor. In further embodiments, the biological sample is a fluid sample from the microenvironment surrounding the tumor. In some embodiments, the population of cells suspected of comprising the anti-tumor cytotoxic CD8+ T-cell of cells suspected of comprising the anti-tumor cytotoxic CD8+ T-cell are from an animal, optionally a mammal such as but not limited to a human patient diagnosed with a cancer. Non-limiting examples of such cancers include leukemia and cancers that produce solid tumors.

In some embodiments, the population of cells suspected of comprising the cytotoxic CD8+ T-cell are isolated from the animal by a method comprising FACS or magnetic bead based sorting of the cells from a biological sample isolated from the animal.

Methods of Expansion

In some embodiments, the method yet further comprises culturing the anti-tumor CD8+ cytotoxic T-cells under conditions for expansion of the anti-tumor CD8+ cytotoxic T-cell to a clonal population, thereby generating a clonal population of the anti-tumor CD8+ cytotoxic T-cells. In some embodiments, to expand the cells to a clonal population, the isolated cell or cells are cultured in an effective culture medium, such as but not limited to RPMI and DMEM, supplemented with an effective amount of one or more of BSA, L-glutamine, pen/strep, amino acids, and a cytokine, such as but not limited to IL-2, IL-7, IL-15, and IFNγ, for an appropriate amount of time and at an appropriate temperature. Also provided is the clonal population of cells prepared by this method. The population can be at least 80% homogeneous, or at least 85%, or at least 90%, or at least 95%, homogeneous.

Methods of Modification/Engineering

In some embodiments, the method yet further comprises modifying the anti-tumor CD8+ cytotoxic T-cells to express an engineered T-cell receptor, such as a chimeric antigen receptor, on the cell surface.

Such cell engineering methods are known in the art—for example, the engineered T-cell receptors may be introduced through traditional recombinant methods such as, but not limited to, transformation, transduction, or transformation or through "gene-editing" based approaches such as, but not limited to, methods employing TALENs and/or CRISPR-Cas based editing.

Compositions, Methods, and Kits

Not to be bound by theory, it is believed that the population of anti-tumor CD8+ cytotoxic T-cells generated by the methods described herein have superior anti-tumor activity than other populations of T-cells. Since an anti-tumor cytotoxic CD8+ T-cell is a cytotoxic T-cell and/or a precursor thereof which is CD8+ and expresses CD8αα on its surface, it is believed to have a proclivity towards survival/residence in the various tissues. Accordingly, the anti-tumor cytotoxic CD8+ T-cell would have improved cytotoxic potential to migrate to and become activated within tumors present in mucosal or peripheral tissues.

Accordingly, further aspects of the disclosure relate to a population of cells prepared by the method disclosed herein, i.e., tumor-specific CD8+ cytotoxic T-cells that bind to a TL tetramer. The anti-tumor CD8+ cells can be bound to the tetramer, isolated from the tetramer, or cultured and expanded to a clonal population of anti-tumor cytotoxic CD8+ T-cells.

Still further aspects relate to a composition comprising one or more of: the tetramer, the isolated cell, or the population and a carrier, optionally a pharmaceutically acceptable carrier.

Pharmaceutical compositions of the present invention may be administered in a manner appropriate to the disease to be treated or prevented. The quantity and frequency of administration will be determined by such factors as the condition of the patient, and the type and severity of the patient's disease, although appropriate dosages may be determined by clinical trials.

In some embodiments, the composition further comprises one or more of CD4+ cytotoxic T-cells and an immune checkpoint inhibitor. Some aspects relate to TL tetramer bound to an anti-tumor CD8+ T-cell, e.g., one isolated according to the method disclosed herein.

Diagnostic and Therapeutic Uses

Some aspects relate to a method of inhibiting the growth of a tumor or a cancer cell, comprising contacting the cell with an effective amount of any one of a population of cells prepared by the method disclosed herein, i.e., tumor-specific CD8+ cytotoxic T-cells that bind to a TL tetramer, optionally bound to the tetramer, isolated from the tetramer, or cultured and expanded to a clonal population of anti-tumor cytotoxic CD8+ T-cells; a clonal population thereof, or composition comprising said anti-tumor cytotoxic CD8+ T-cells disclosed herein. In some embodiments, the method further comprises administering the population of CD4+ cytotoxic T-cells or composition comprising said population disclosed herein.

In some embodiments, the method further comprises measuring the growth inhibition of the tumor or cancer cell by noting cell death or growth inhibition. The contacting can be in vitro or in vivo. When performed in vitro, the method is a means to identify if the cell population is a possible therapeutic for the patient, i.e., it can be utilized as a companion diagnostic or to assay for combination therapies to be used in parallel or sequentially with the disclosed compositions. When performed in vivo, the methods are novel and effective anti-tumor or anti-cancer therapies that can be used alone or in combination with other therapies known in the art and briefly described herein.

Additional aspects relate to a method of treating a tumor or cancer or eliciting an anti-tumor immune response in a subject in need thereof, comprising, or alternatively consisting essentially of, or yet further consisting of, administering an effective amount of any one of the population, clonal population, or composition disclosed herein. In some embodiments, the method further comprises administering one or more cytoreductive therapy and/or immunotherapy to the subject before, after or concurrently with the disclosed methods In some embodiments, the method comprises contacting a cancer or tumor cell isolated from the subject with an effective amount of the therapy, and assaying for the growth inhibition effect of the cell population or the compositions, prior to administration of the cell populations or compositions to the subject. In some embodiments, the method comprises assaying for the therapeutic effect of the therapy, after administration of the therapy to the subject.

This can be achieved by any appropriate method known in the art, e.g., by scan or immunological assay to measure tumor burden, such as but not limited to using anti-CEA. Assessing the success of such treatment can be accomplished to methods known in the art. The FDA Guidance for Industry: Clinical Trial Endpoints for the Approval of Cancer Drugs and Biologics lists a number of exemplary endpoints such as but not limited to length of disease-free or progression-free survival, time to progression, objective response rate, and biomarker or symptom based endpoints for particular cancers. Additional endpoints include but are not limited to reduction in tumor number or tumor size.

In some embodiments, the species of the cell population or composition is identical to the subject being treated. In some embodiments, the cells are autologous or allogenic to the subject being treated. In some embodiments, the therapy is administered as a first-line therapy, a second-line therapy, a third-line therapy, a fourth-line therapy and or a fifth line-therapy.

Still further aspects relate to diagnostic methods using a TL tetramer. For example, a method of selecting a treatment for a tumor or cancer in a subject in need thereof, comprising: administering a plurality of detectably labeled TL tetramers to the subject, detecting the TL tetramers in the subject to determine the concentration of anti-tumor CD8+ cytotoxic T-cells, and selecting the appropriate cytoreductive and/or immunotherapy from the measured concentration of the cells detected. In some method aspects, the subject is a mammal, optionally a canine, feline, or a human patient.

Further provided is a kit for generating detecting and expanding a population of high affinity anti-tumor CD8+ cytotoxic T-cells generated according the method of isolation described herein comprising a TL tetramer and instructions for use.

The following examples are intended to illustrate, and not limit the scope of this disclosure.

EXAMPLES

Figure 4:
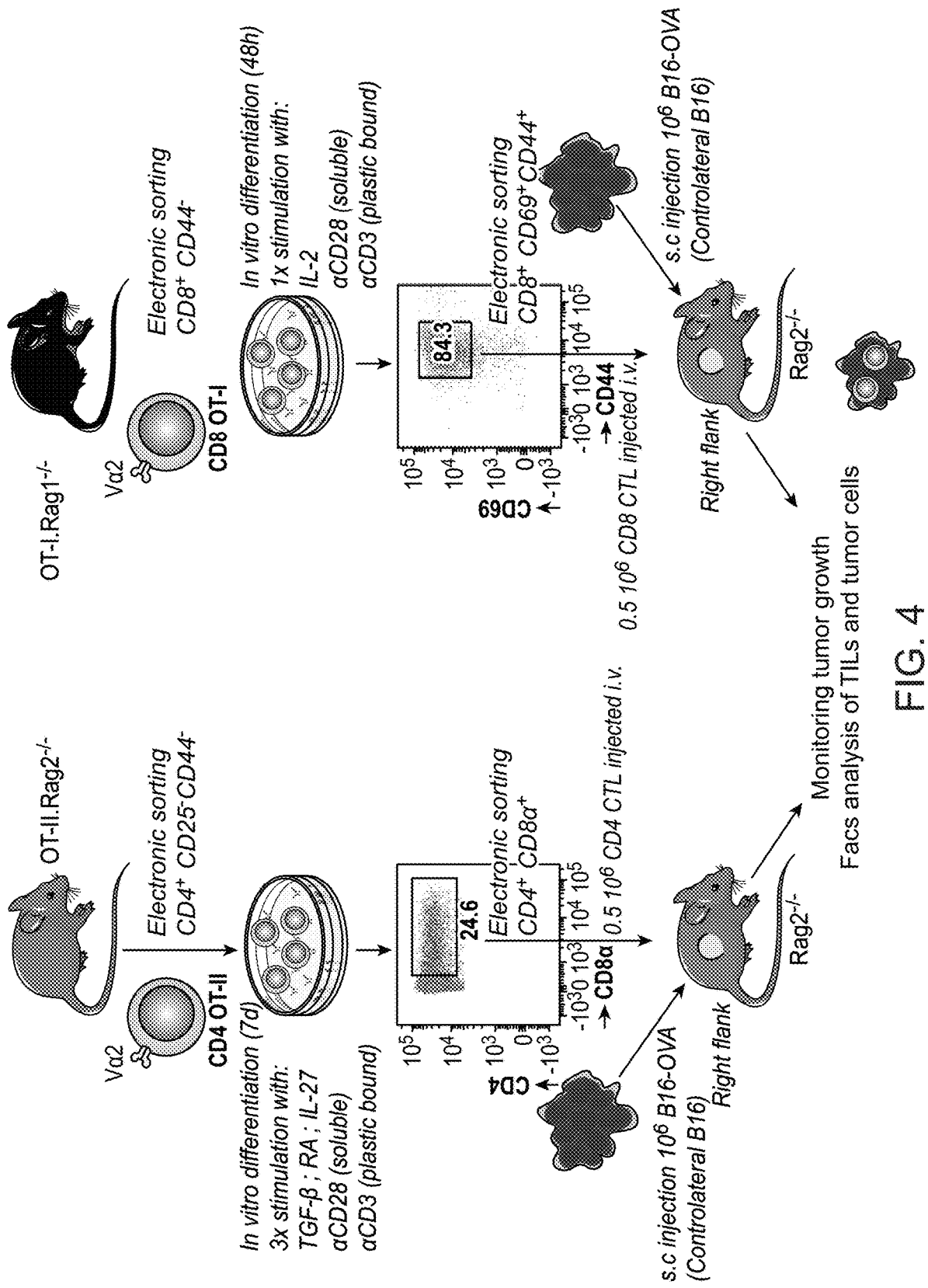
FIG. 4 is a flowchart depicting an experiment comparing the results of RABI27 treated CD4+ T-cells with CD8+ T-cells.
Figure 5:
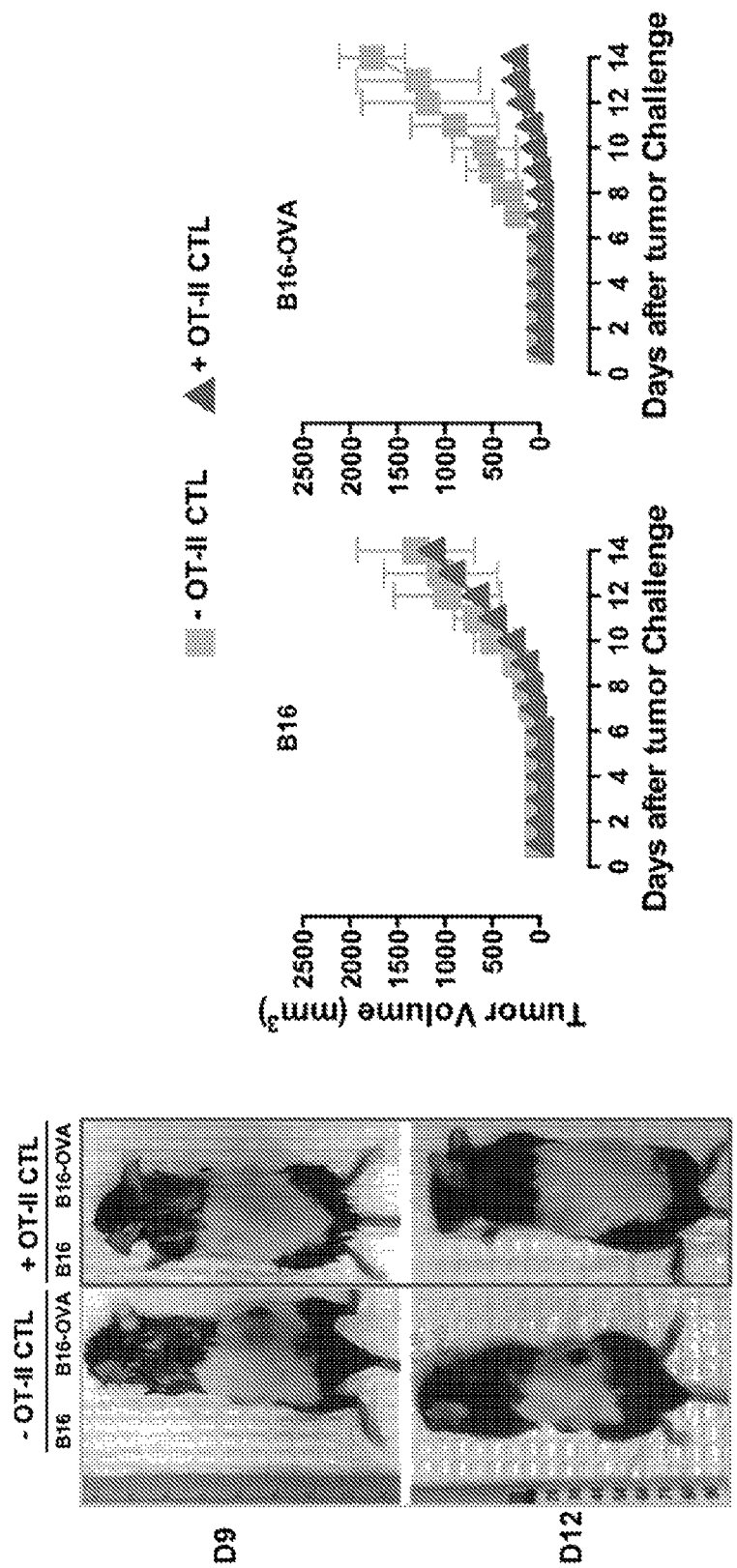
FIG. 5 demonstrates that in vitro RABI27-generated tumor-antigen specific CD4+ cytotoxic control tumor growth. OTII CD4 T-cells with specificity for OVA expressed by B16-OVA tumor cells (melanoma) were reprogrammed in vitro using the RABI27 method. After 3× RABI27 cycles, CD8α-expressing OTII CD4 T-cells were sorted and injected in C57B16 mice, which also received s.c.
Figure 6:
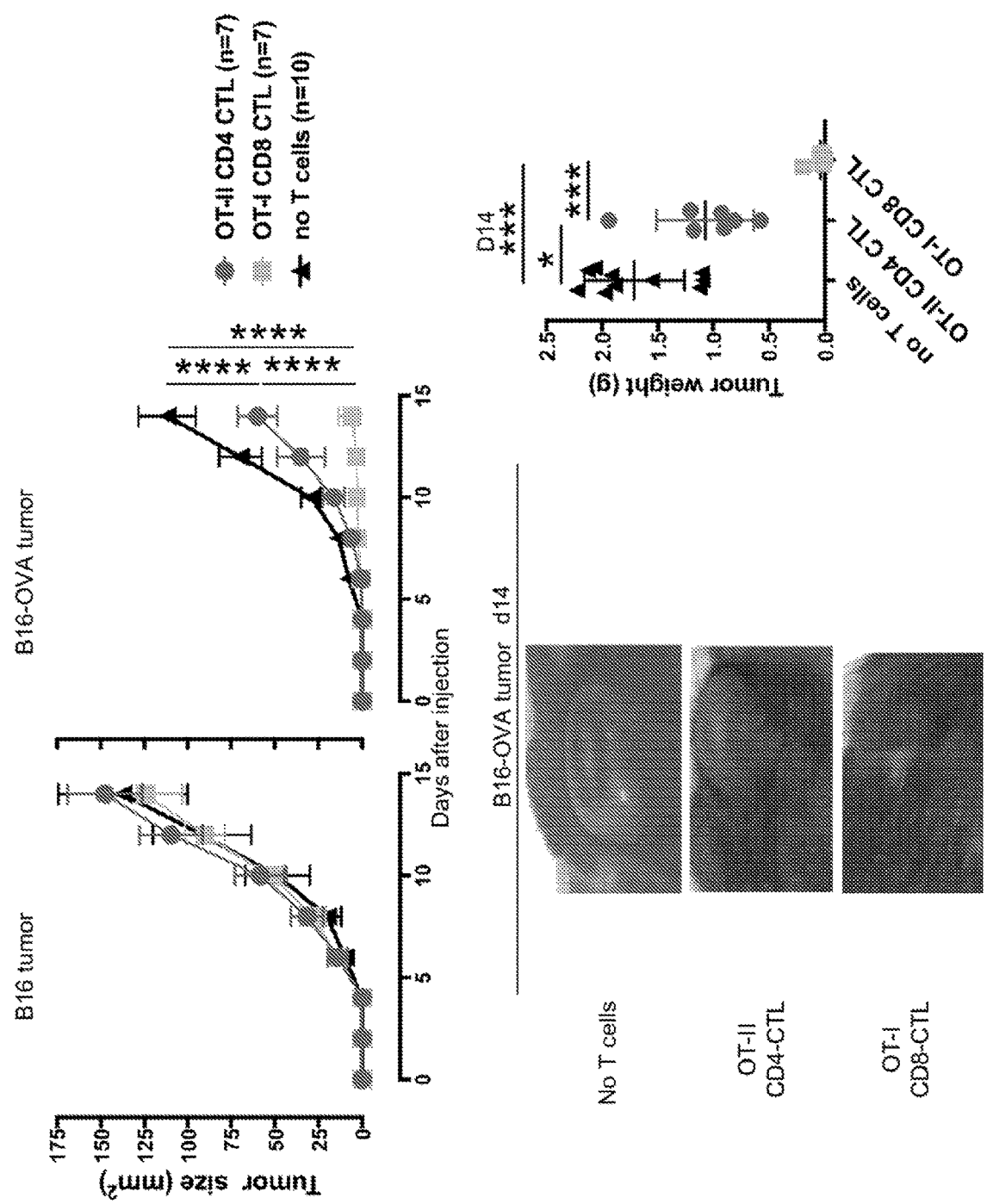
FIG. 6 shows tumor reduction after treatment with RAB127 treated CD4+ T-cells, CD8+ T-cells, and a control.
Figure 7:
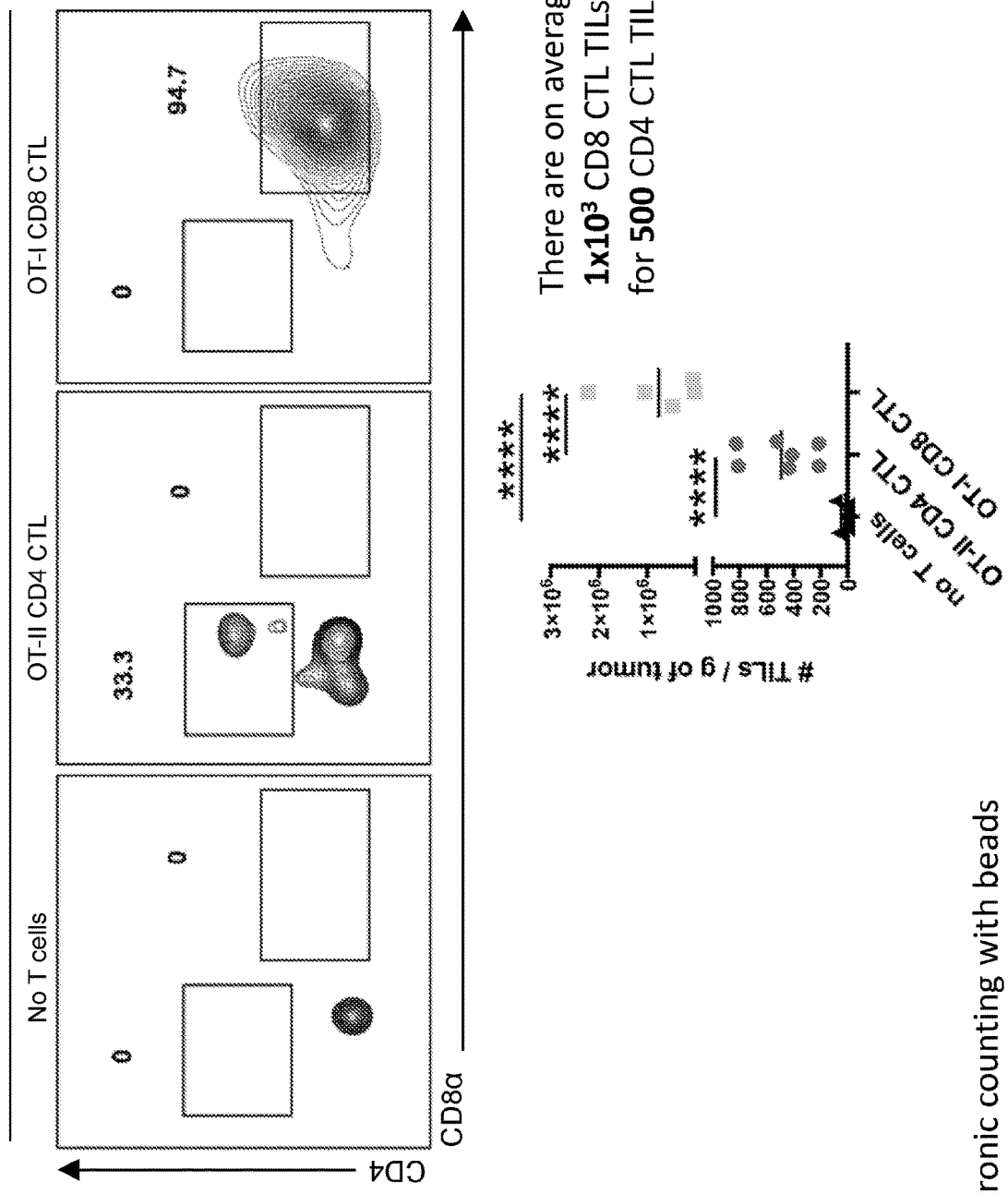
FIG. 7 shows plots of tumor infiltrating lymphocytes (TILs) by treatment group, harvested of day 14 of the experiment described in FIG. 5.
Figure 8:
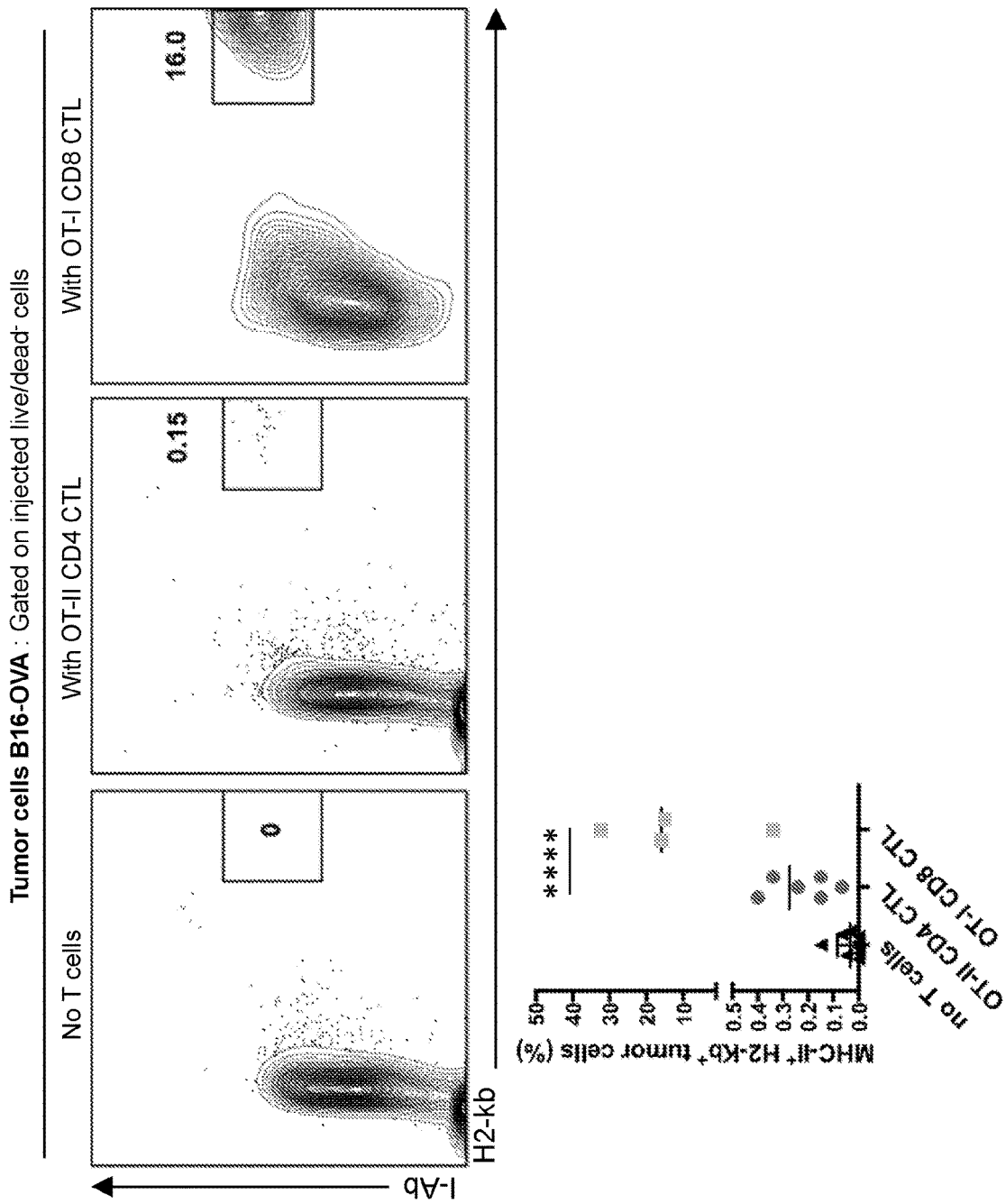
FIG. 8 shows that B16 tumor cells do not express MHC class II, but induce MHC class II (I-A$^b$) in response to IFNg (activated CD8 T-cells produce IFNg). The B16 tumor cells do not express MHC class II (left panel), therefore, transferred CD4 CTL can't see their Ag (OVA) on tumor (B16-OVA) cells. As a result, most transferred CD4 CTL died in vivo. In addition, activated anti-tumor specific CD8 CTL kill the tumor cells in response to detecting their Ag on the tumor cells presented by MHC class I (OVA Ag on the B16-OVA). In addition they also secrete IFNg which in turn upregulate MHC class II expression on the tumor cells (right panel). Anti-tumor reactive CD8 T-cells become restrained (induction of PD-1) or undergo TL- or activation-induced cell death. Therefore, a combination of anti-tumor CD8 T-cells (or NK T-cells or DN T-cells) and anti-tumor CD4 CTL which can kill tumor cells once MHC class II is induced, can be a powerful anti-tumor immunotherapy.
Figure 9:
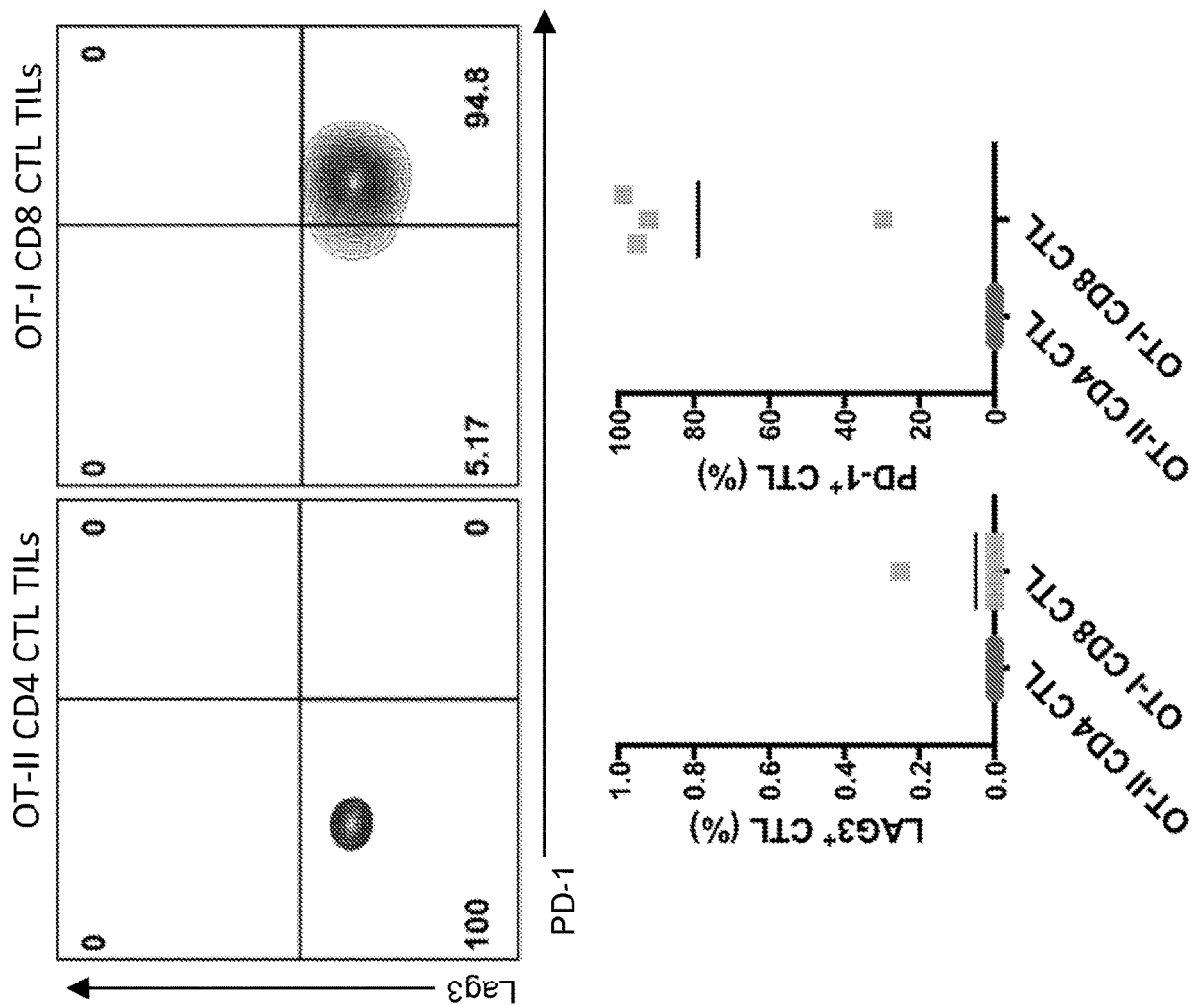
FIG. 9 shows that CD4+ tumor infiltrating lymphocytes do not express inhibitory molecules such as PD-I or Lag3.
Figure 10A:
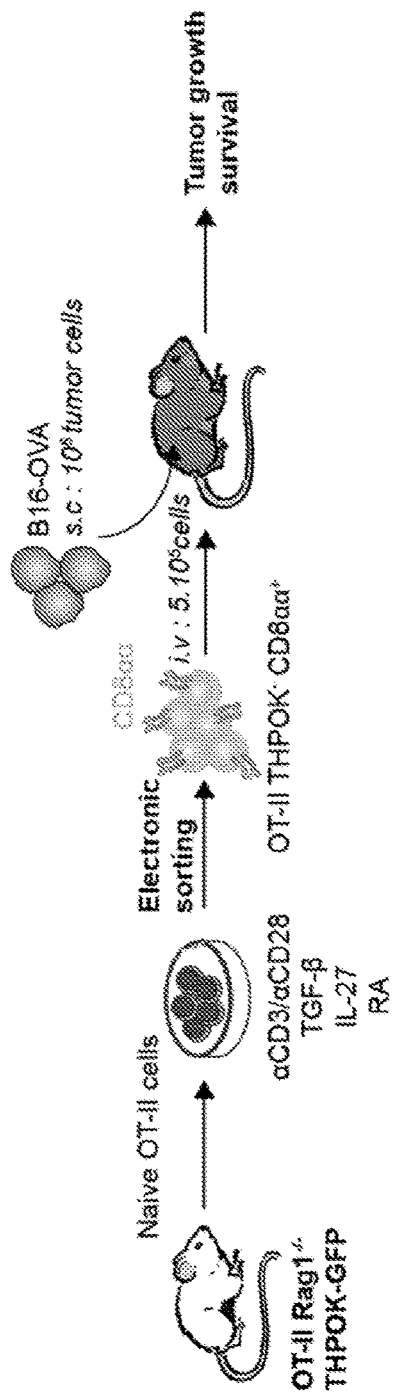
FIG. 10A shows naïve OT-II CD4 T-cells from Rag2−/− THIPOK-GFP were activated with anti-CD3 and anti-CD28 in presence of TGF-β, IL-27, and retinoic acid. After 8 days of culture, CD8αα+ ThPOK-GFP-live reprogrammed T-cells were sorted and transferred to Rag−/− mice injected the same day with B16-OVA melanoma tumors. Tumor volume and survival was then assessed every 2 days.
Figure 10B:
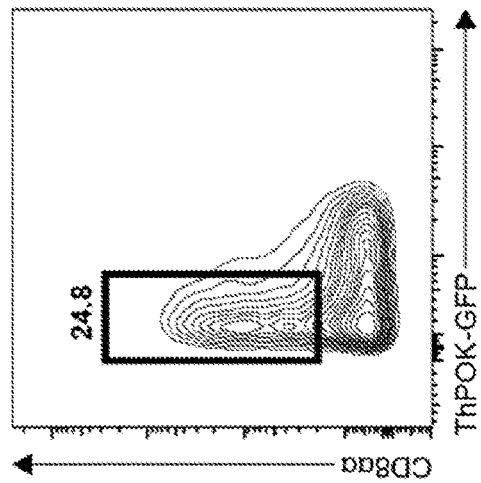
FIG. 10B shows flow cytometry analyzing expression of CD8α and Thpok in in vitro cultivated OT-II CD4 T-cells under CD4 CTL condition. Data are representative of at least 3 independent experiments. The gate shows the population sorted for injection.
Figure 11B:
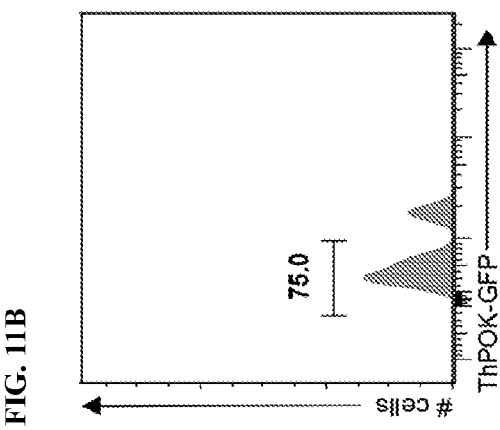
FIG. 11B shows flow cytometry analyzing expression of ThPOK on electronically gated CD45+Ot-II CD4+ tumor infiltrating lymphocytes. Data are representative of 7 biological replicates.
Figure 11A:
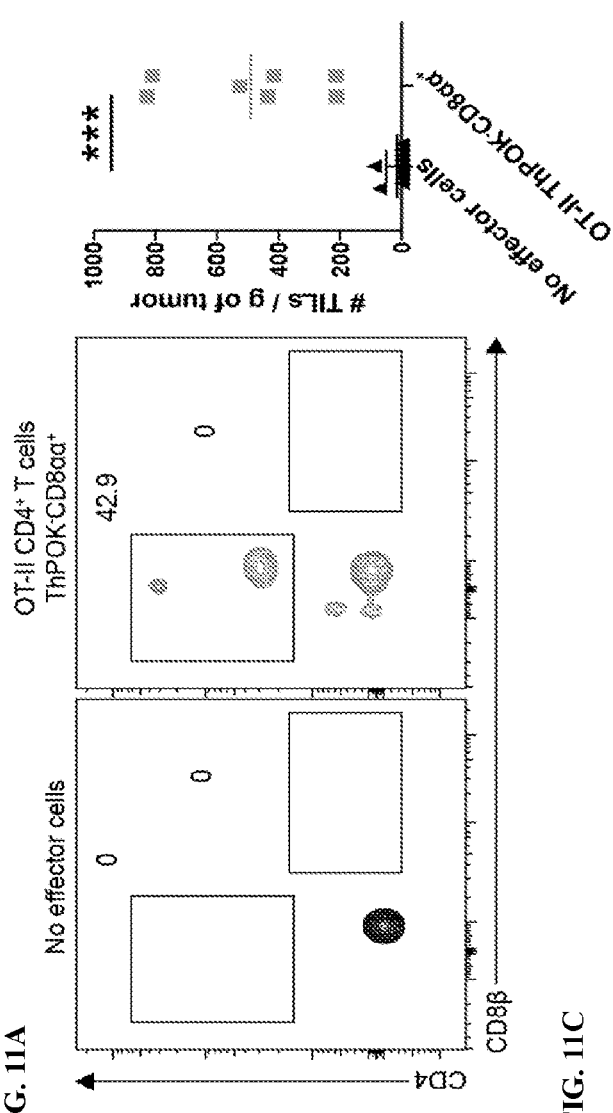
FIG. 11A has two panels. The left panel shows flow cytometry analyzing expression of CD4 and CD8β on electronically gated CD45+ tumor infiltrating lymphocytes. The right panel shows quantification of number of OT-II CD4+ tumor infiltrating lymphocytes relative to tumor weight. n=7-10 mice per group.
Figure 11C:
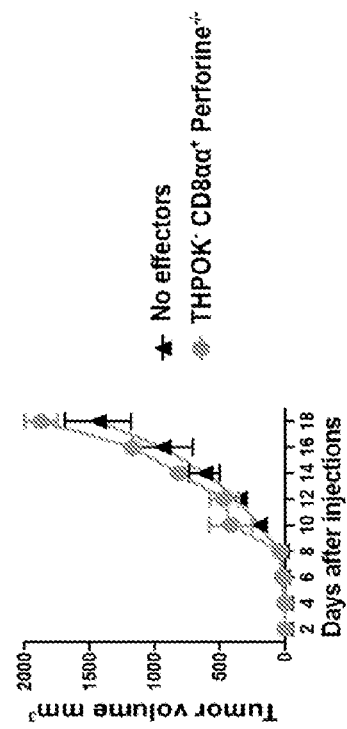
FIG. 11C shows data obtained as in FIG. 11A but where the naïve OT-II CD4 T are from Rag2−/− THPOK-GFP perforin−/− mice. Tumor volume was assessed over time. n=2-3 mice per group.
Figure 12:
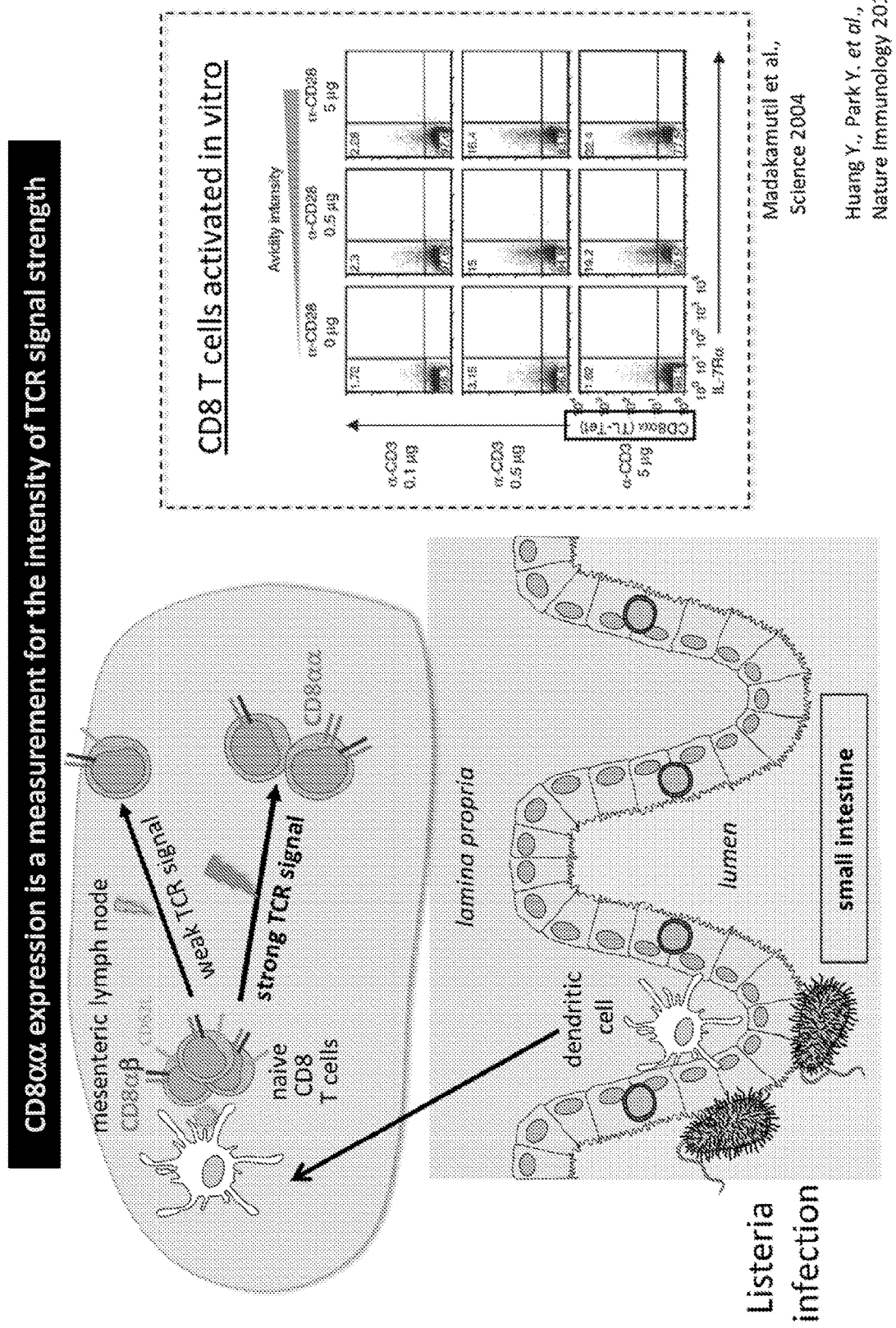
FIG. 12 shows schematics and data demonstrating that CD8αα expression is a measurement for the intensity of TCR signal strength. Not to be bound by theory, Applicant hypothesizes that CD8αα expression is induced by intensity of TCR signal strength.
Figure 13:
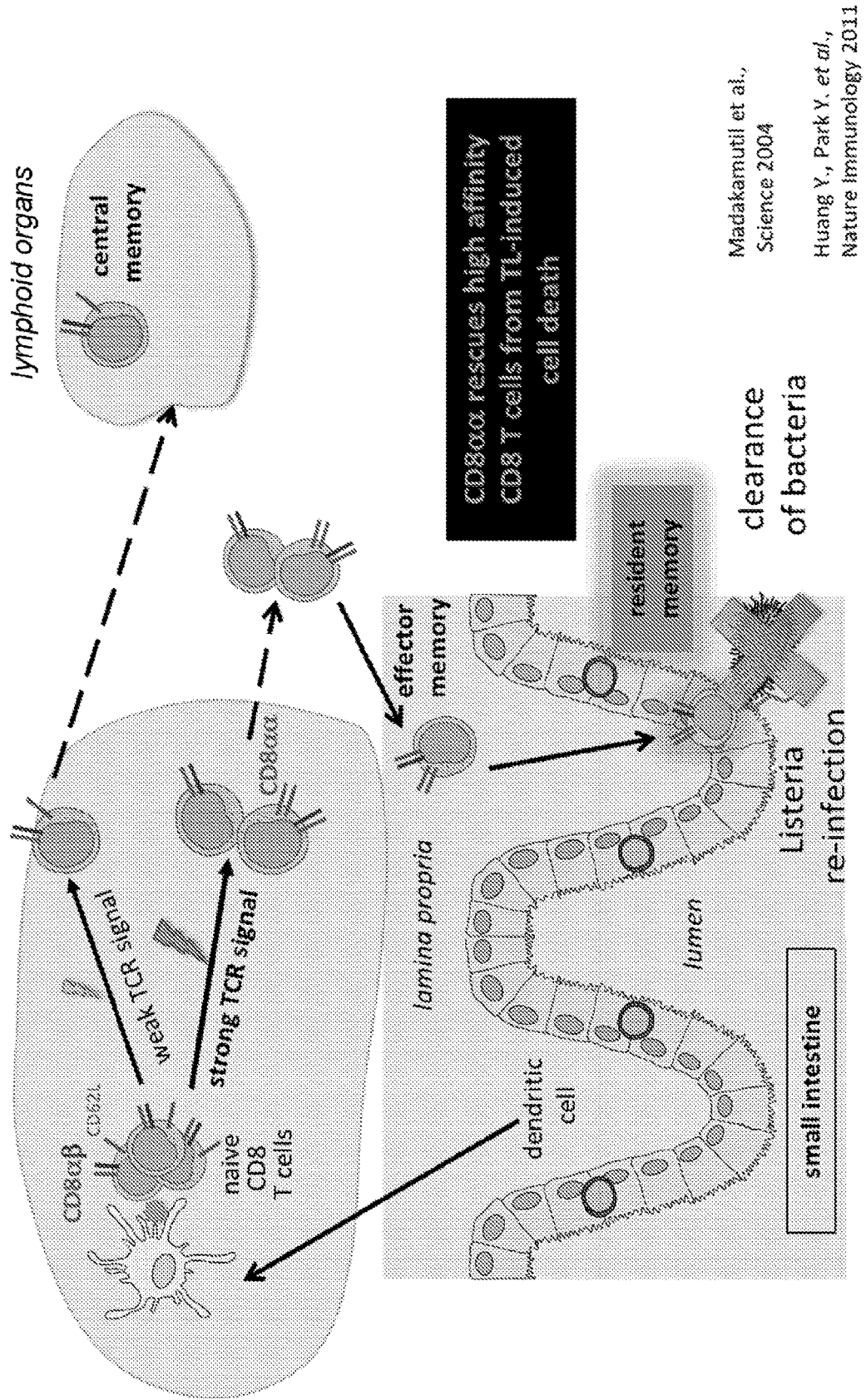
FIG. 13 shows a schematic demonstrating that CD8αα rescues high affinity CD8 cells from activation-induced cell death.
Figure 14:
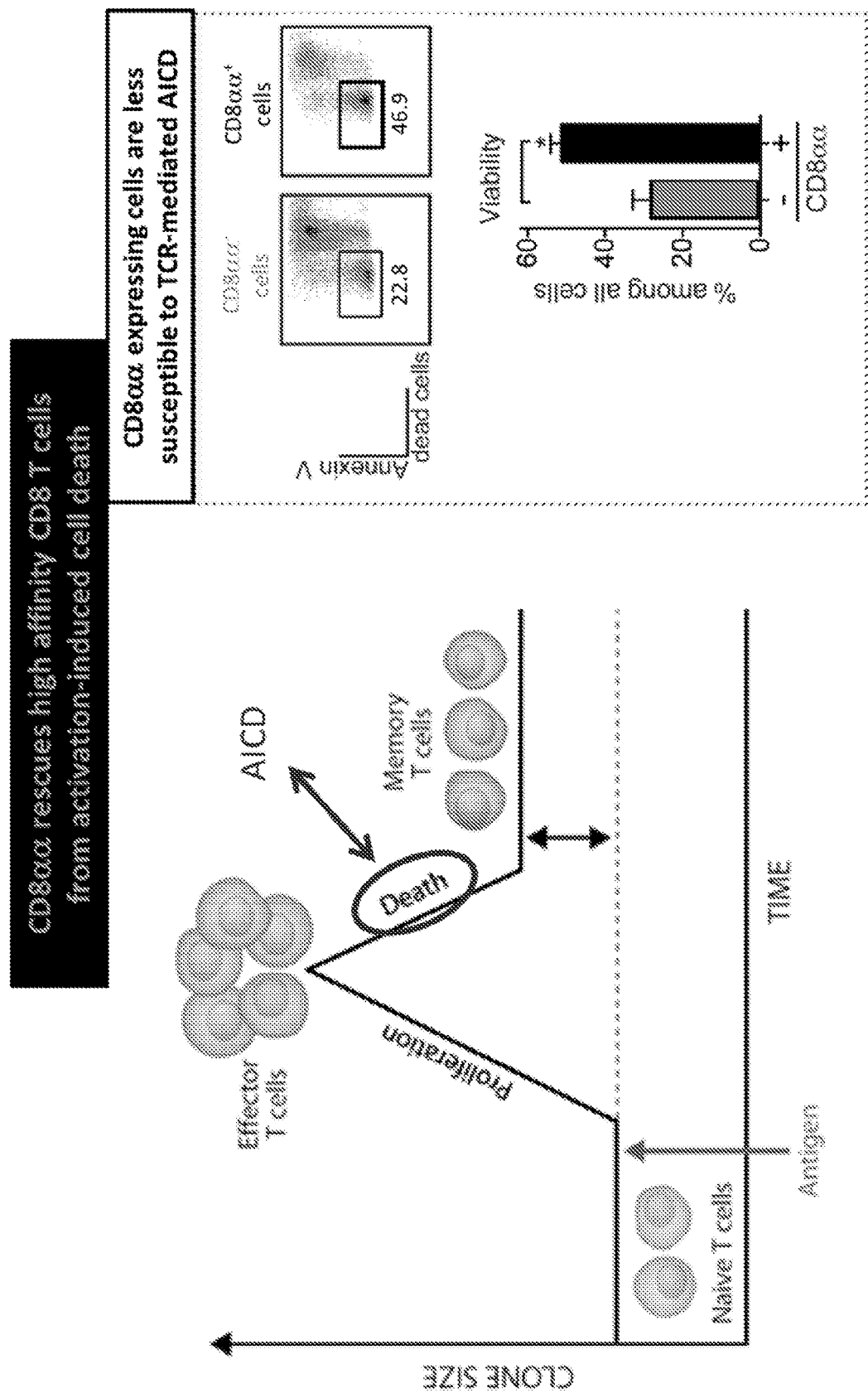
FIG. 14 shows a schematic showing activation induced cell death and a figure demonstrating CD8αα expressing cells are less susceptible to activation-induced cell death.
Figure 15:
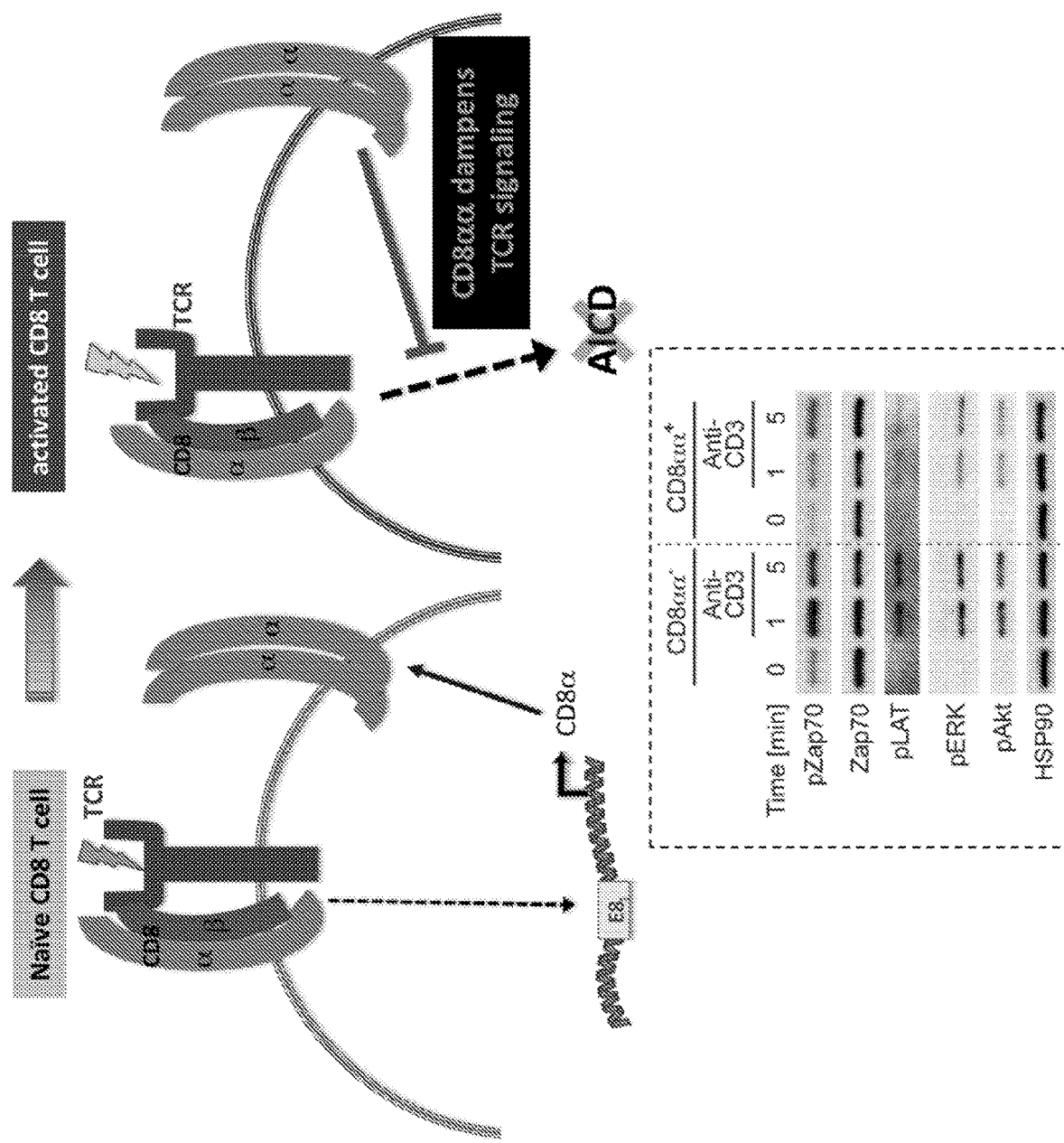
FIG. 15 shows a schematic demonstrating that CD8αα rescues high affinity CD8 cells from activation-induced cell death.
Figure 16:
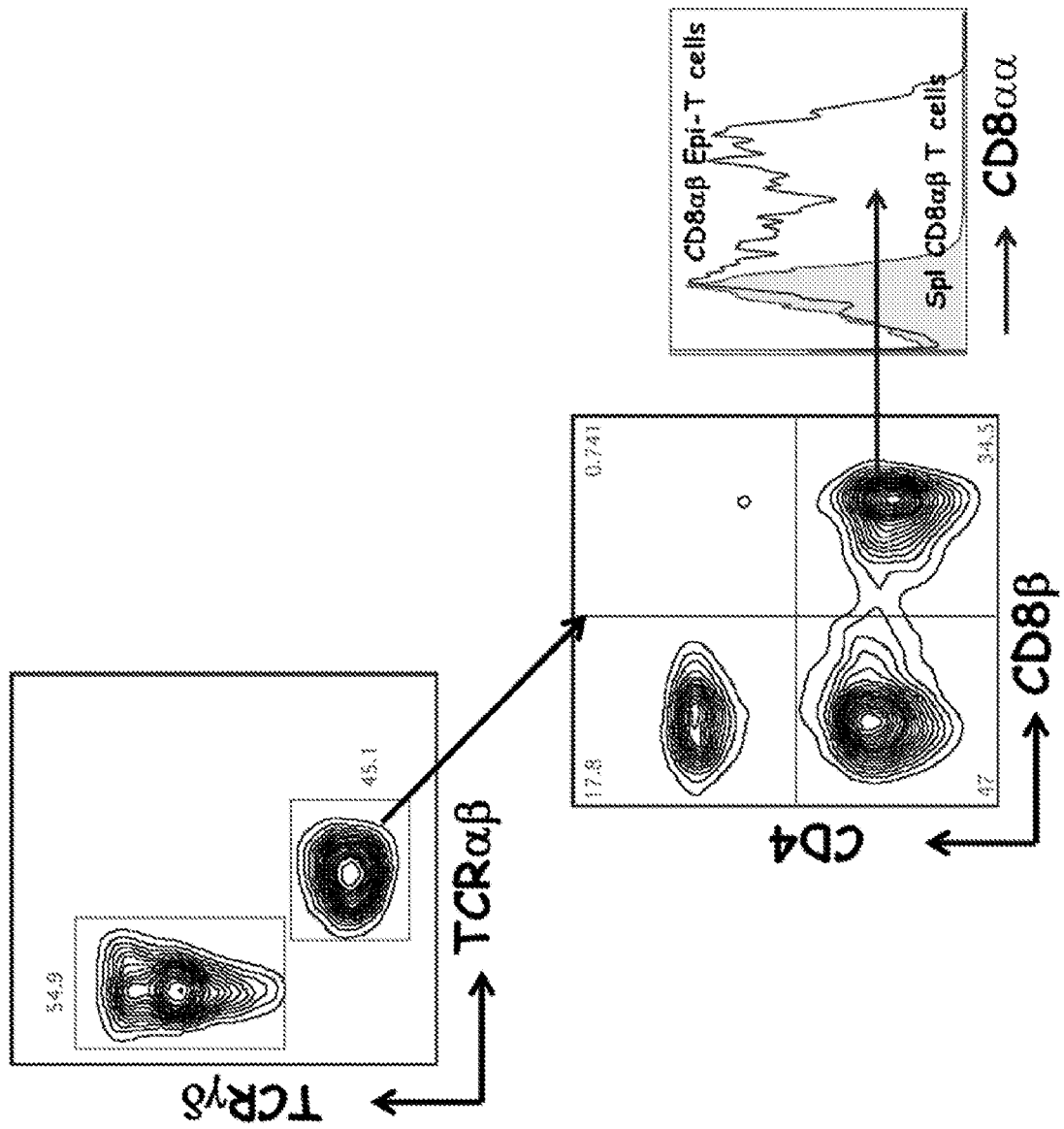
FIG. 16 demonstrates that CD8ab epithelial T-cells or other tissue residenT-cells are enriched in CD8αα co-expressing CD8 αβ(Tissue resident effector and effector memory T-cells) $T_{REM}$ cells.
Figure 17:
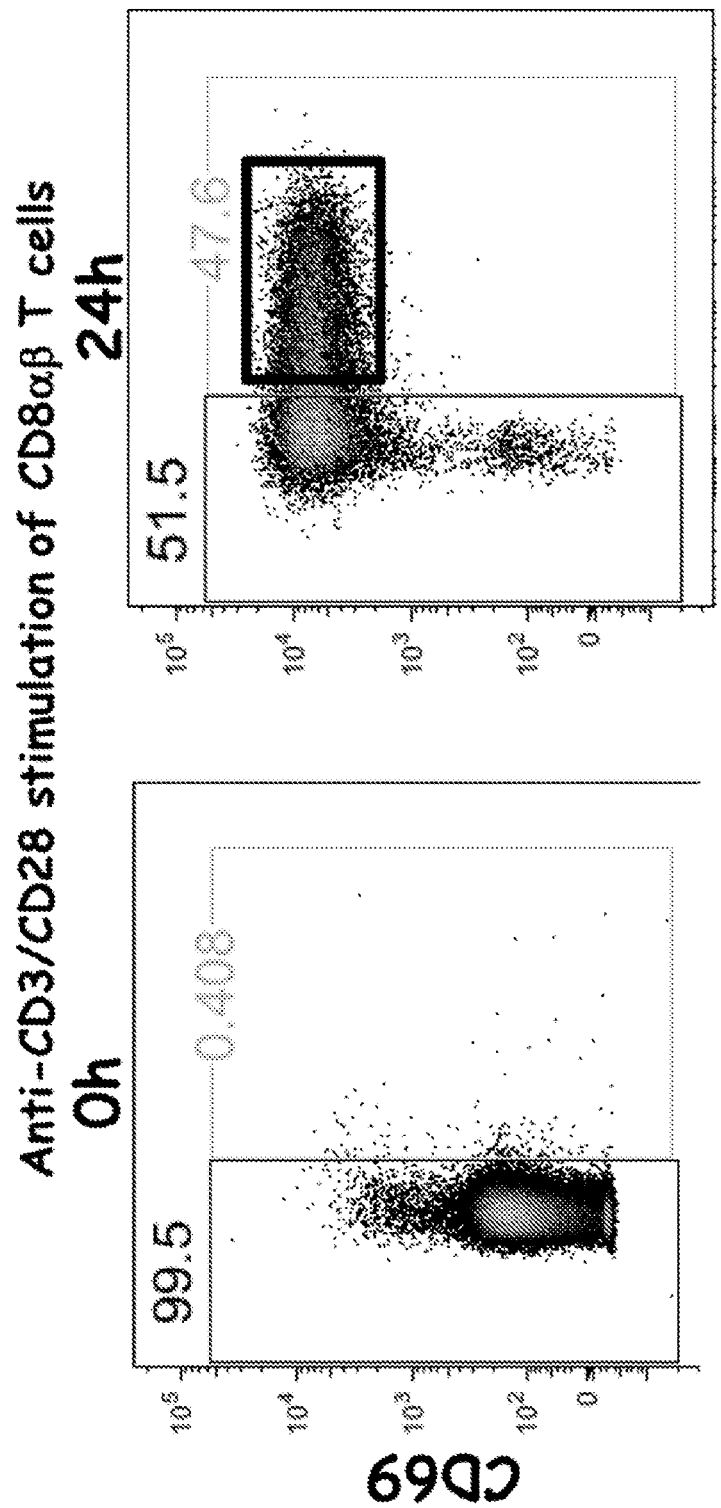
FIG. 17 demonstrates that strongly TCR-activated CD8αβ T-cells induce expression of CD8αα.
Figure 18:
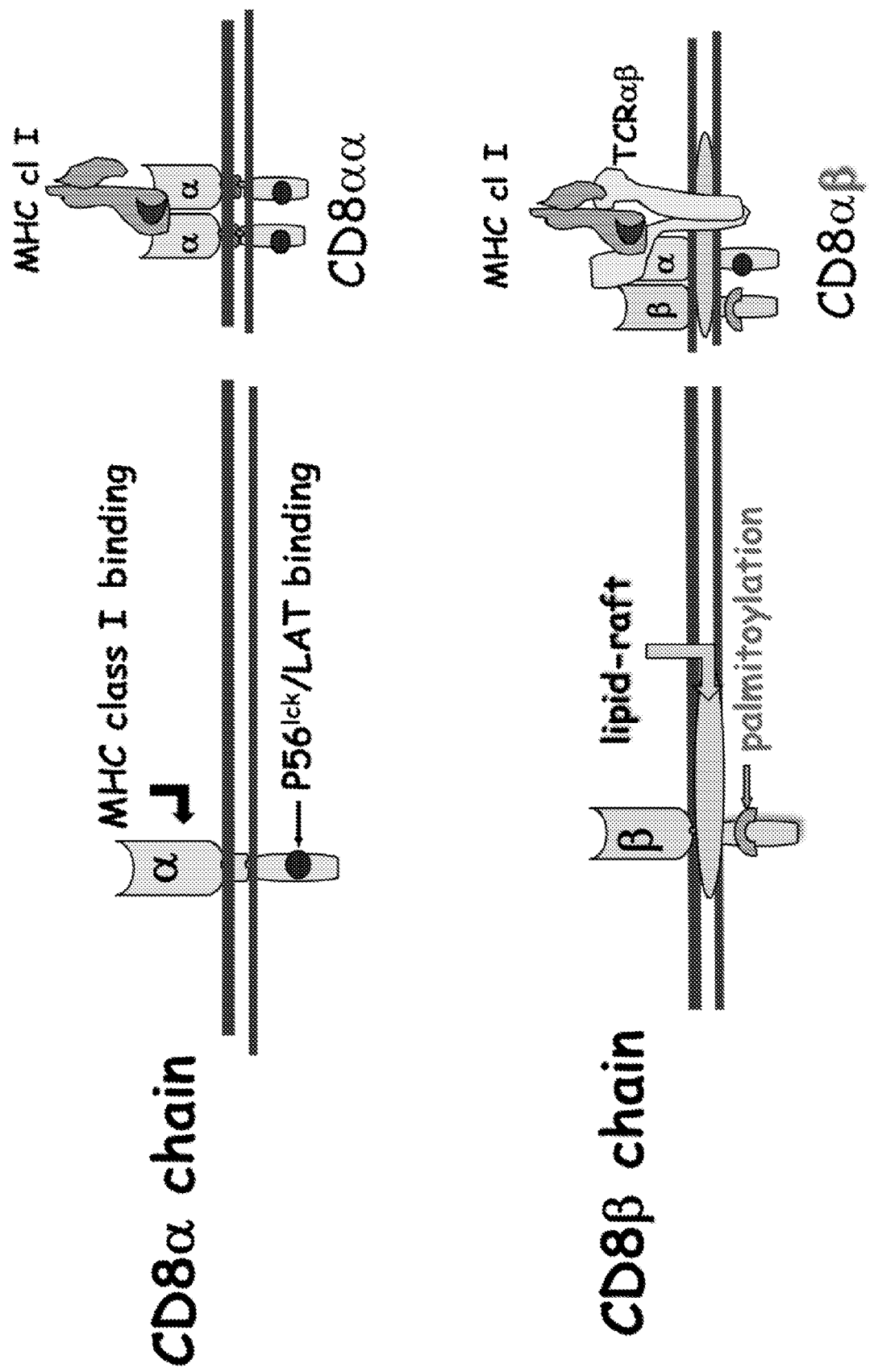
FIG. 18 is a schematic showing that, unlike CD8αβ, CD8αα cannot function as a TCR co-receptor. The cytoplasmic tail of CD8α recruits Lck and LAT. CD8b is palmitoylated and therefore recruits CD8α/lck/LAT into lipids rafts closest the TCR. In the absence of CD8b, CD8αα recruit lck and LAT but fail to join the TCR complex in the lipid rafts, thereby sequestering the signaling molecules away from the TCR rather than enhancing the signaling capacity of the TCR. Consequently, CD8ab functions as a co-receptor, whereas CD8αα functions as a co-repressor
Figure 19:
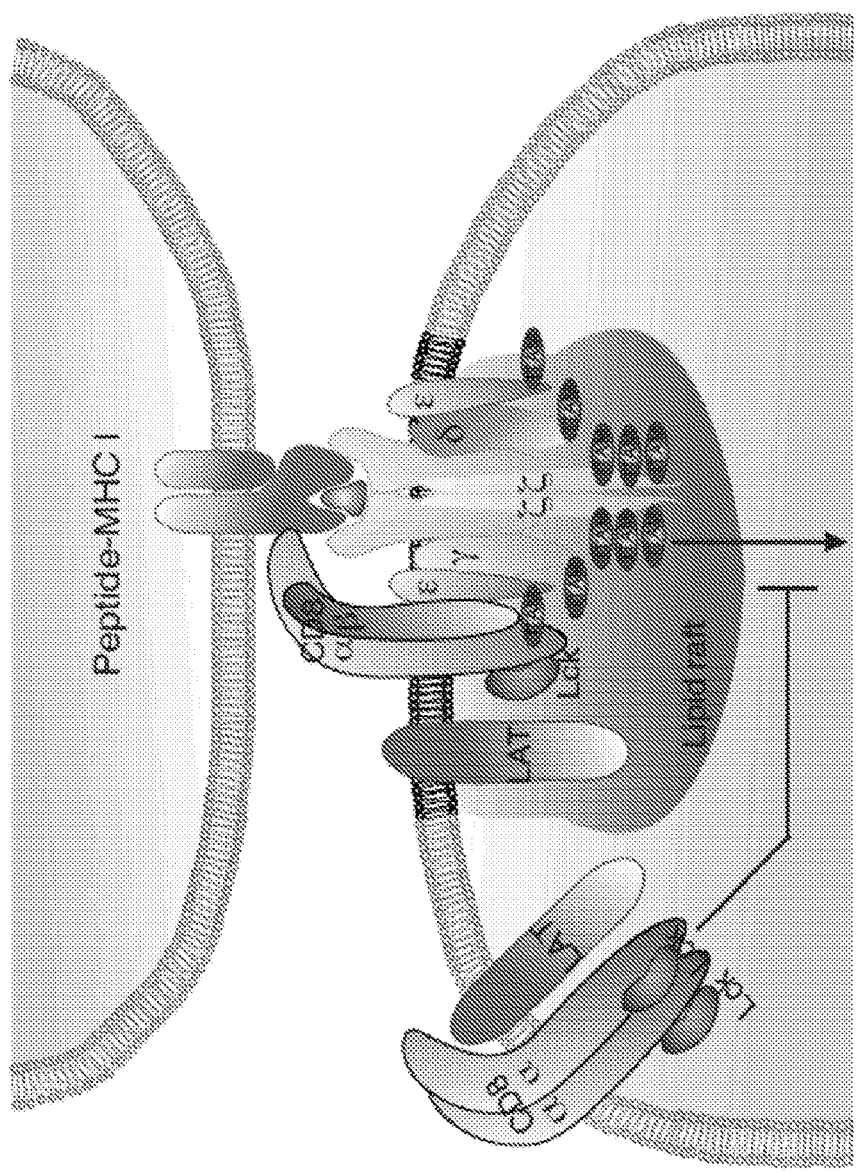
FIG. 19 is reproduced from Cheroutre et al. (2008) Immunity. 28(2):149-159 and provides a schematic showing that CD8αα is an anti TCR co-receptor and counteracts CD8αβ and CD4 TCR co-receptors. The cytoplasmic tail of CD8α recruits Lck and LAT. CD8β is palmitoylated and therefore recruits CD8α/lck/LAT into lipids rafts closest the TCR. In the absence of CD80, CD8αα recruit lck and LAT but fail to join the TCR complex in the lipid rafts, thereby sequestering the signaling molecules away from the TCR rather than enhancing the signaling capacity of the TCR. Consequently, CD8αβ functions as a co-receptor, whereas CD8αα functions as a co-repressor FIG. 20 demonstrates that strong avidity signals increase CD8αα expression on CD8αβ T-cells. CD8αβ T-cells were activated in vitro with various concentrations of a-CD3 and a-CD28 as indicated. T-cells were analyzed for the cell surface expression of CD8αα with TL tetramer and for IL7R.
Figure 20:
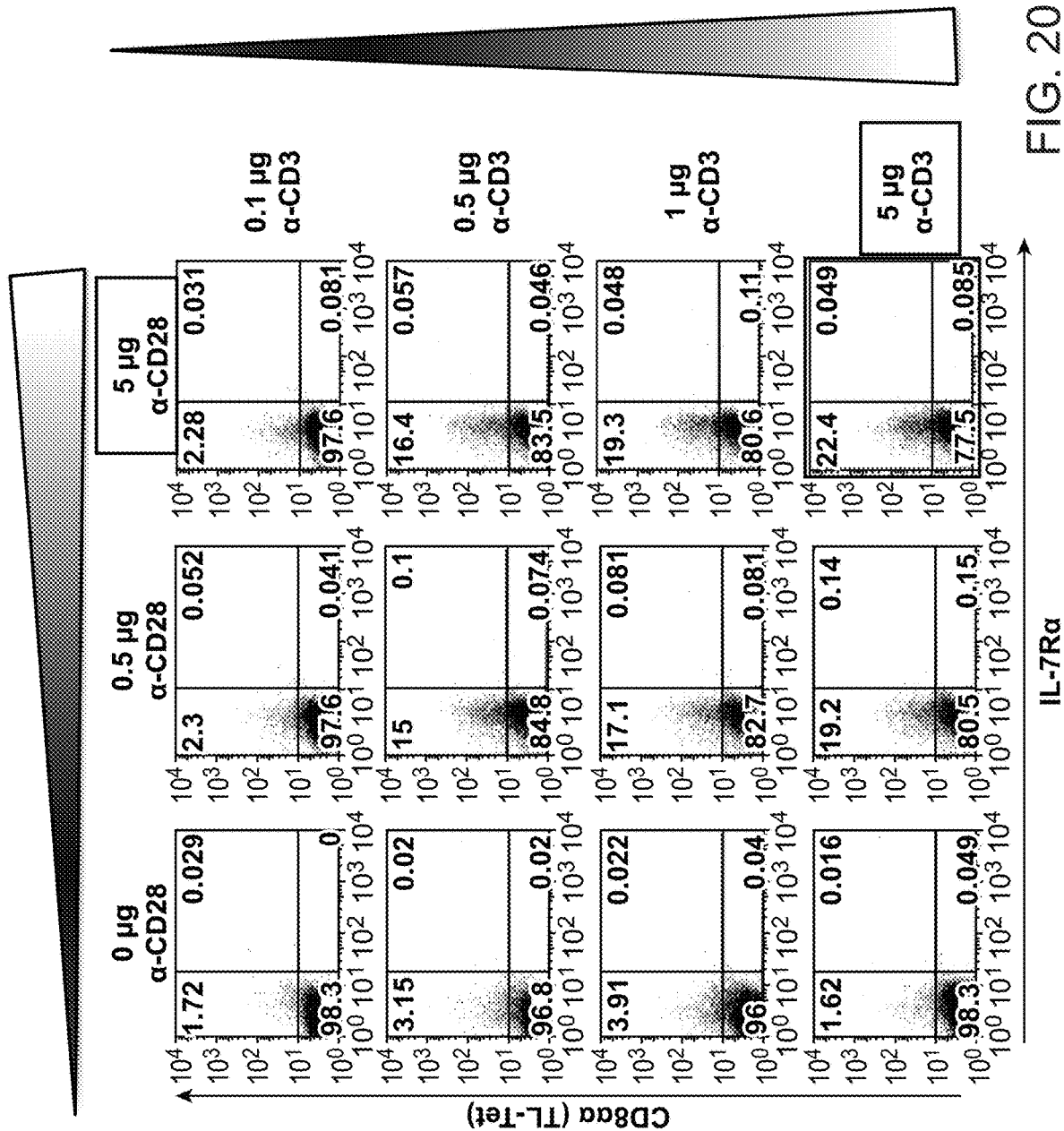
Figure 21:
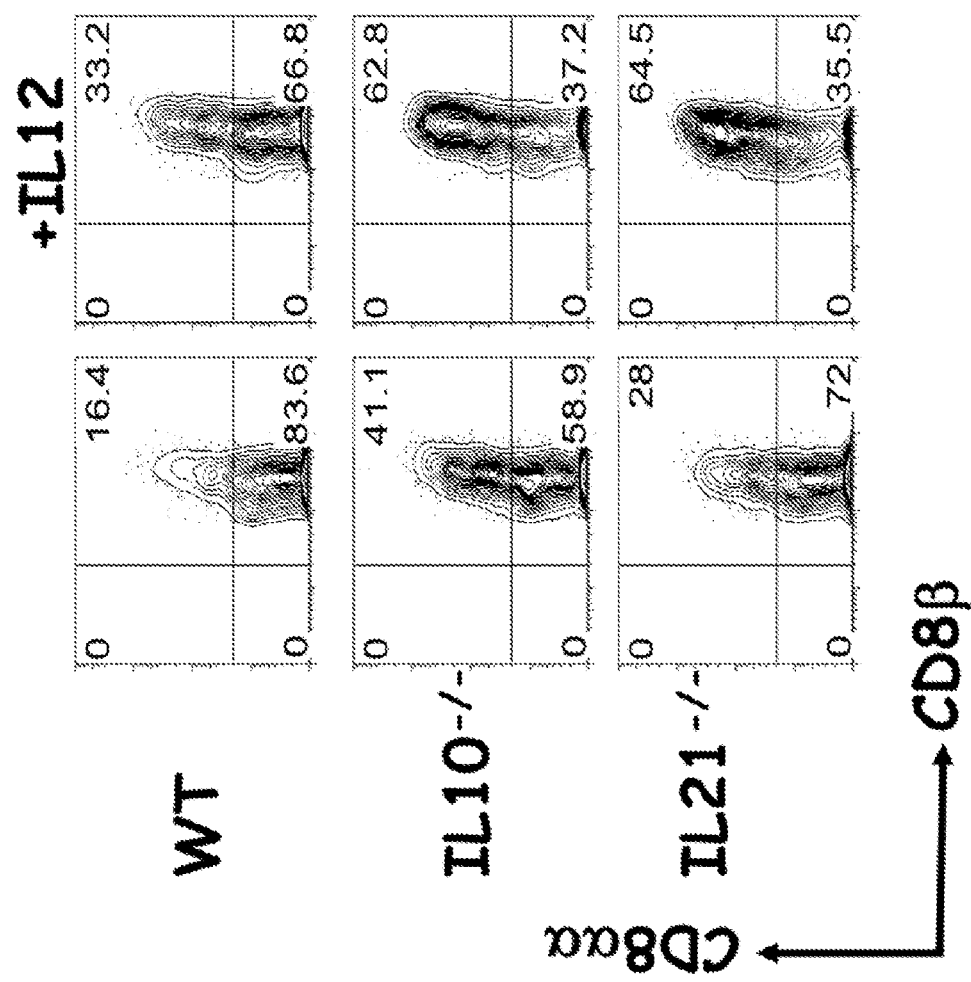
FIG. 21 demonstrates that anti-inflammatory IL-10 and IL-21 inhibit whereas pro-inflammatory IL-12 promotes the generation of CD8αα effector memory precursor cells. CD8ab T-cells isolated from wild type mice (WT) or IL10 deficient mice (IL10−/−), or IL21 deficient mice (IL21−/−) were activated in vitro with anti-CD3/CD28 and with or without IL12. Induction of CD8αα was measured using TL tetramer.
Figure 22:
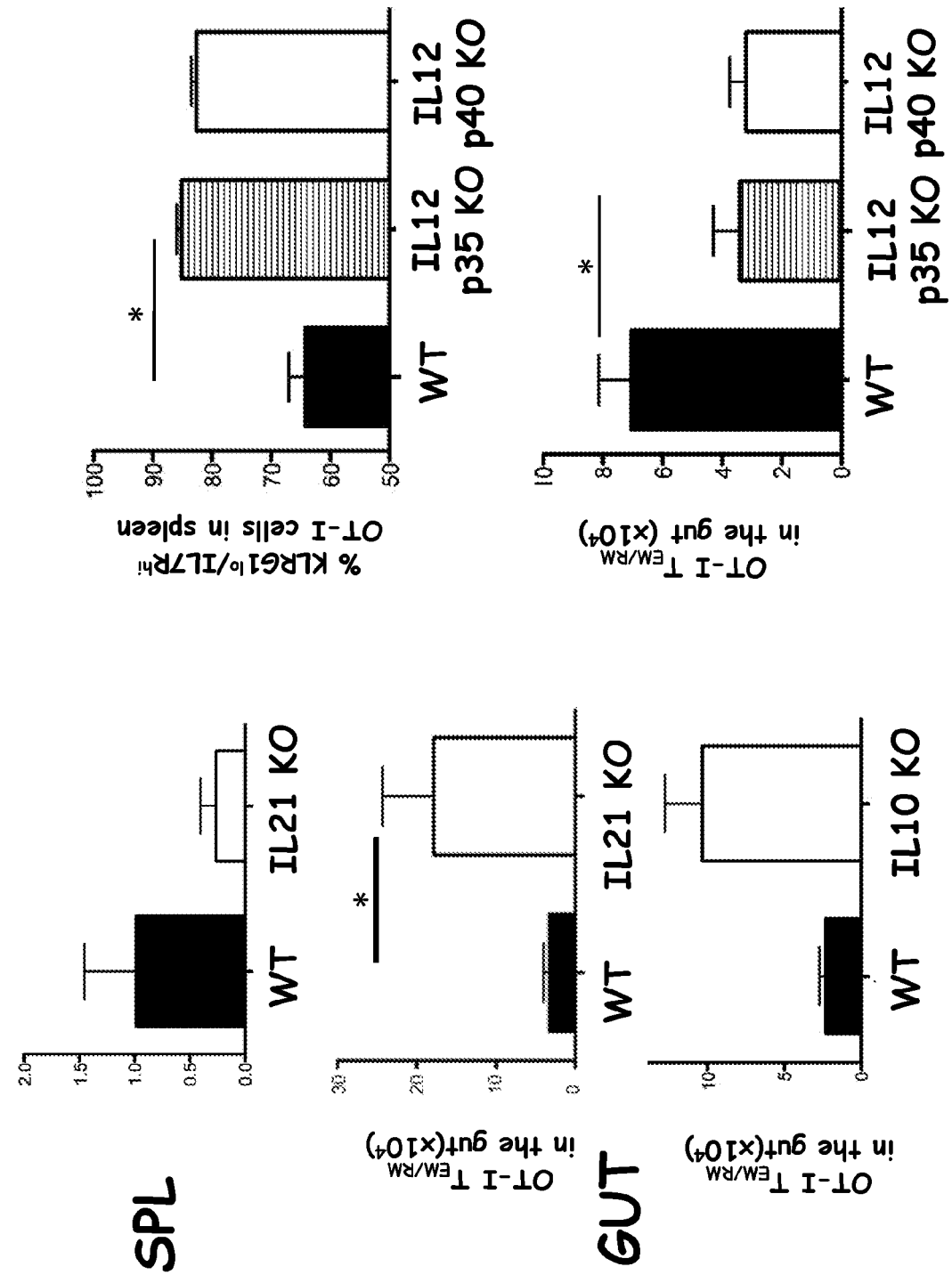
FIG. 22 demonstrates that IL-12 promotes the generation of CD8αβ $T_{EM/RM}$, whereas IL-10 and IL-21 counteract the generation of CD8αβ $T_{EM/RM}$.

Example 1: Generation of Tumor-Specific CD4+ Cytotoxic T-Cell Generation in Murine Model Following the procedure of FIG. 4, isolated CD4+ T-cells were cultured onto an anti-CD3 antibody coated plate with soluble CD28, TGFb, RA, and IL-27 for 1 day (1st culture). Next day, these CD4+ T-cells were re-plated onto a newly anti-CD3antibody coated plate with TGF-β, RA, and IL27 for 3 days (2nd culture), then re-plated and stimulated in the same manner as the 2nd culture (3rd culture). In some cases, CD4 T-cells are further stimulated on anti-CD3 antibody bound plates together with IL15.

This procedure is carried out through routine culture methods. For example, in a 96-well plate, the plate is first washed by complete RPMI1640 culture medium (supplemented with 10% FCS, 2-Me, and pen strep) and then coated with anti-CD3 antibody for over 4 h. The medium is removed completely, then 50 μL of soluble anti-CD28 antibody is added to the plate. Next, 100 μL of the RABI27 mixture (TGFb, RA, and IL27) is added to the plate. Lastly, 50 μL of the cell suspension is added to the plate and mixed well. In regard to 2nd and 3rd culture, after washing the coated plate, 50 μL of medium is added to the plate instead of anti-CD28 antibody.

The results of this experiment are shown in FIGS. 5-9.

It is further determined that regardless of CD8αα expression status (+/−). CD4+ cells were effective to control tumors (FIGS. 10A-D and 11A-C). While tested separately in these examples, it is believed that the combination of both subsets of CD8αα+/THPOK- and CD8αα-/THPOK-cells may further enhance anti-tumor efficacy.

Example 2: Isolation of Anti-Tumor CD8+ Cytotoxic T-Cells in Murine Model

Figure 23:
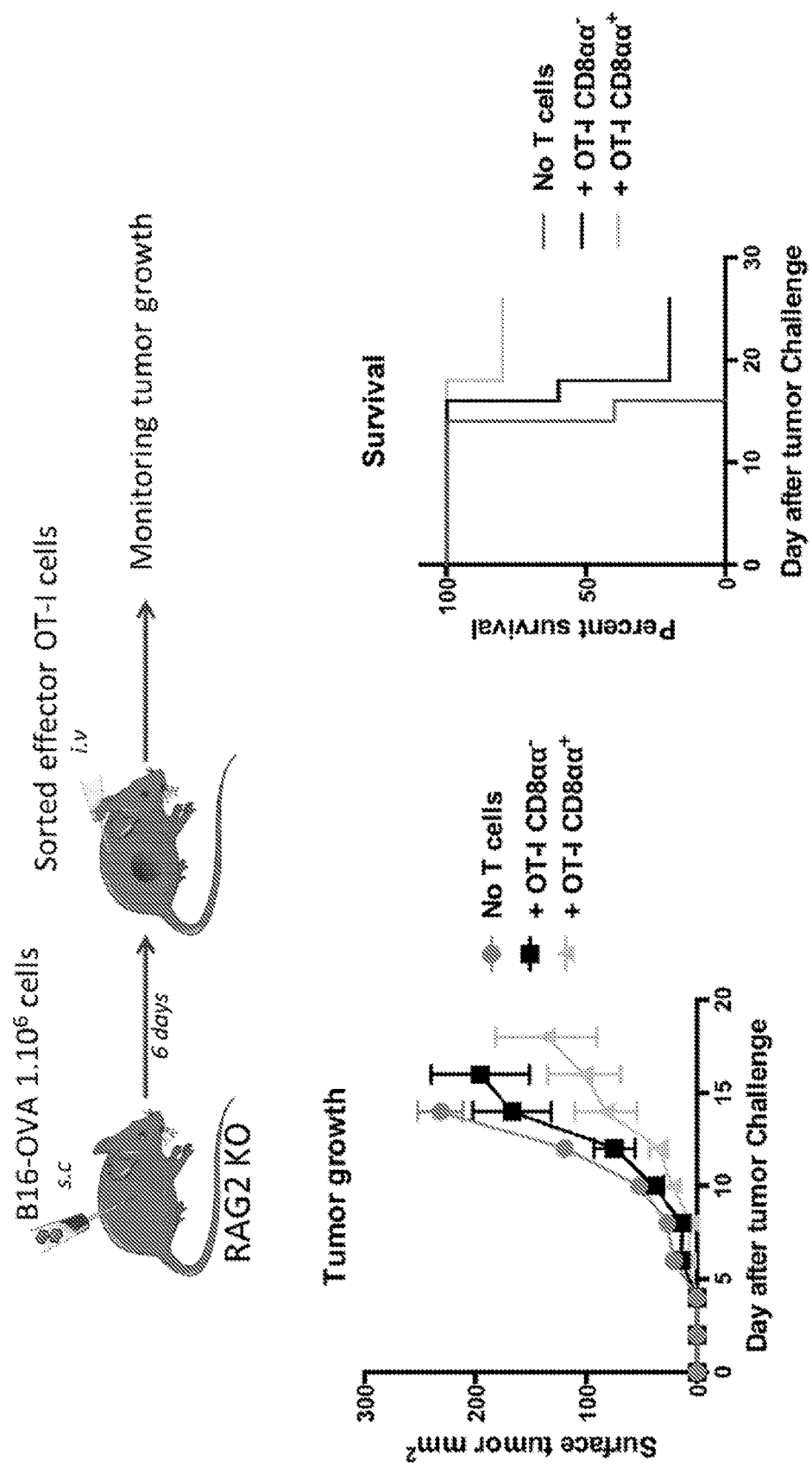
FIG. 23 provides an exemplary experimental set up and representative data.
Figure 25A:
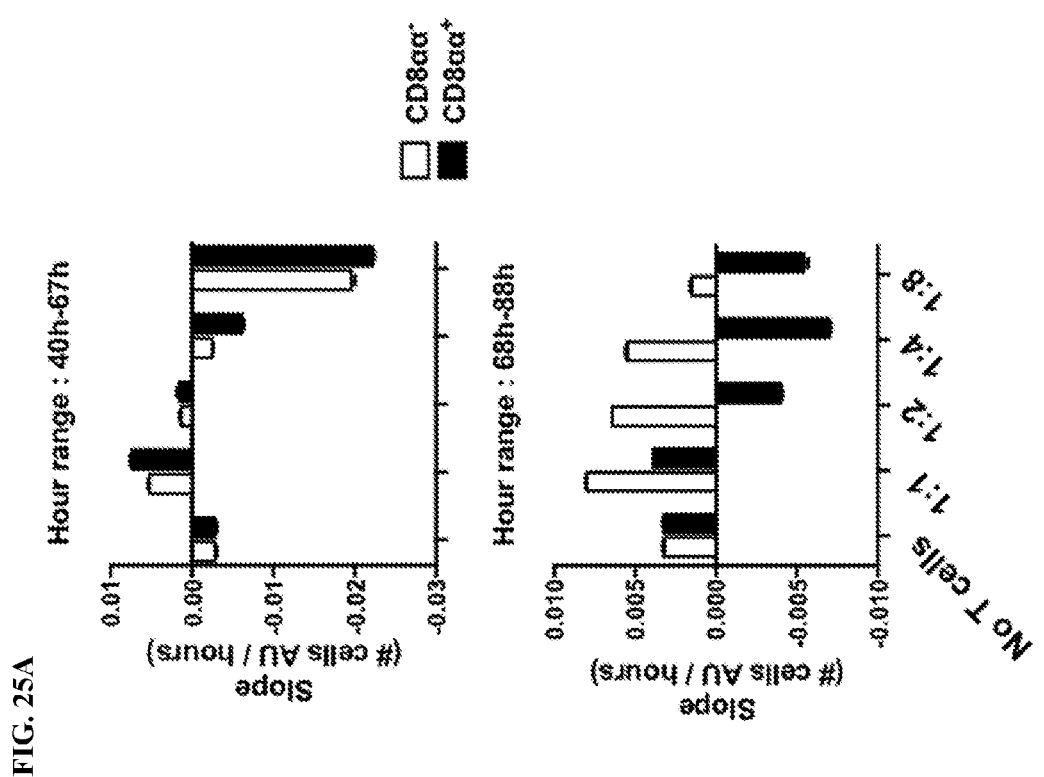
FIG. 25A shows naïve OT-I CD8+ T-cells activated with anti-CD3 and anti-CD28. After 48 h, CD8αα− or CD8αα+ live activated T-cells were sorted and their cytotoxic capacity against B16-OVA melanoma tumor cells was measured in vitro during 90 hours. Quantifications of slopes (targeT-cell number/hours) of each ratio (target:effectors) during 2 different time ranges. Each time point and histogram denote the mean of 3 technical replicates.
Figure 25C:
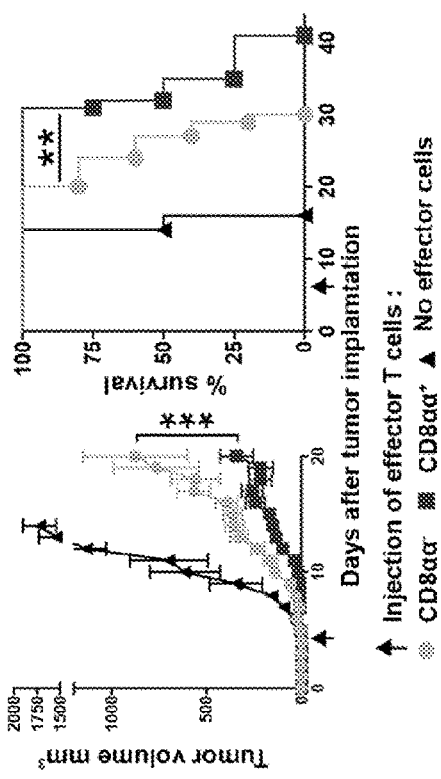
FIG. 25C has two panels. The left panel shows volume of B16-OVA tumor implanted in Rag2−/− mice injected or not with different effector CD8 T-cells. The right panel shows a survival curve of each group of mice after tumor challenge. ***P<0.001 by T-test for tumor volume (left) and log-rank test for survival analysis (right). n=2 mice (no effector cells group); n=4-5 mice (effector T-cells groups). Data are representative of three independent experiments.
Figure 25B:
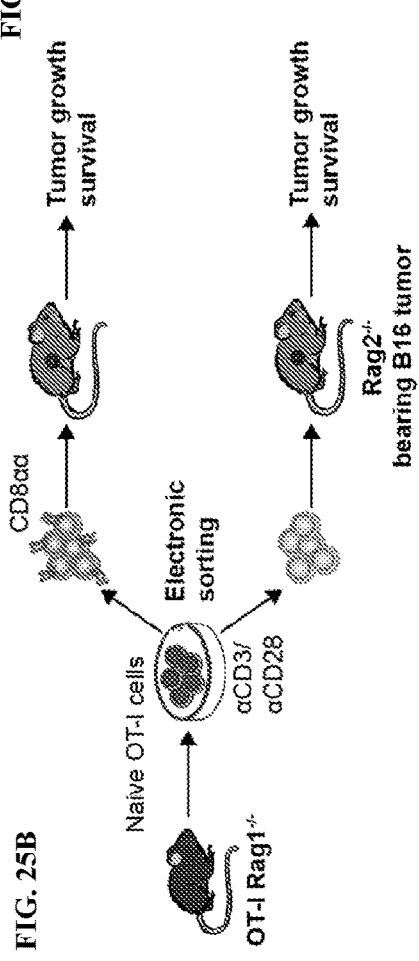
FIG. 25B shows naïve OT-I CD8+ T-cells were activated with anti-CD3 and anti- CD28. After 48 h, CD8αα− or CD8αα+ live activated T-cells were sorted and transferred to Rag−/− mice bearing B16-OVA melanoma tumors. Tumor volume and survival was then assessed every 2 days.
Figure 25E:
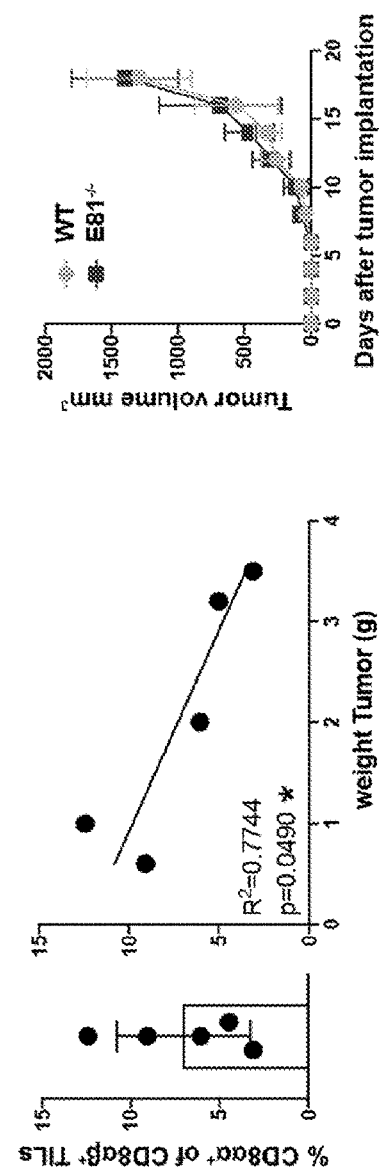
FIG. 25E shows the results of an experiment in which wild type or E81−/− mice were implanted with B16 tumor ($10^6$). Tumor volume was assessed over time. n=5-6 mice per group.
Figure 25D:
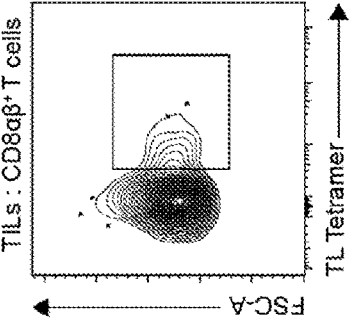
FIG. 25D shows the results of an experiment in which C57B/6 mice were implanted with B16 tumor ($10^6$) and analyzed after 10 days. The left panel shows low cytometry analyzing expression of CD8αα expression by TL-tetramer staining on electronically gated CD8αβ tumor infiltrating lymphocytes. The right panel shows quantification of CD8αα expression CD8αβ tumor infiltrating lymphocytes as a function of B16 tumor weight. Each symbol represents an individual mouse. Line represents the regression curves. n=5 mice.

CD8+ T-cells were isolated from the spleens of Rag1 KO OT-I mice using Miltenyi negative selection kit for CD8+ T-cells (untouched). Naïve CD8 (CD8b+CD44$^{low}$) T-cells were subsequently sorted using a BD Aria FACs sorter. Cells were then activated in vitro with coated anti-CD3e (cl. 2C11, 1 μg/ml) and soluble anti-CD28 (0.5 μg/ml) for 48 h. After 48 h, activated T-cells were stained with anti-CD8b and TL-tetramer PE (TL-tet, 1/100) for 20 min at room temperature, washed and sorted for TL-tet+(CD8αα+) and TL-tet-(CD8αα−) CD8+ T-cells using a BD Aria FACs sorter. 500,000 CD8αα− or CD8αα+OT-I cells were then injected intravenously into Rag1 KO mice bearing B16 or B16-OVA tumor on the flank. Progression of the tumor size was then assessed every day (FIG. 23).

CD8+ T-cells were isolated from the spleens of Rag1 KO OT-I mice using Miltenyi negative selection kit for CD8+ T-cells (untouched). Naïve CD8 (CD8b+CD44$^{low}$) T-cells were subsequently sorted using a BD Aria FACs sorter. Cells were then activated in vitro with coated anti-CD3e (cl. 2C11, 1 μg/ml) and soluble anti-CD28 (0.5 μg/ml) for 48 h. After 48 h, activated T-cells were stained with anti-CD8b and TL-tetramer PE (TL-tet, 1/100) for 20 min at room temperature, washed and sorted for TL-tet+(CD8αα+) and TL-tet-(CD8αα−) CD8+ T-cells using a BD Aria FACs sorter.

Example 3: Combination Treatment with Anti-Tumor CD8+ Cytotoxic T-Cells and Tumor-Specific CD4+ Cytotoxic T-Cells in Murine Model CD8αα+CD8+ T-cells are isolated according to the method of Example 2. ThPOK$^-$ CD4+ T-cells are generated according to the method of Example 1. Both cell populations are administered to one or more mice bearing tumors—simultaneously and sequentially in either order—and compared to a negative control and the results of just administering each of the cell populations alone. The sequential administration of the CD8αα+CD8+ T-cells and then the ThPOK$^-$ CD4+ T-cells yields superior results.

Not to be bound by theory, the sequential treatment of first MHC class I restricted CD8+ T-cells followed by MHC class II restricted CD4+ CTL is believed to be an attractive apporach for many tumors that escape immune surveillance under the pressure of the CD8+ T-cell response by inactivating the MHC class I pathway. Those tumors become invisible for CD8 effector cells (even in anti-PD1 or CTLA4 immune blockade or in some cases with the use of CAR T-cells). However, because during their initial response the CD8+ T-cells not only kill tumor cells but also produce IFNg that upregulates expression of MHC class II, the tumors might become invisible for CD8+ T-cells but they become visible for CD4+ T-cells. Hence, the sequential treatment with expanded anti-tumor CD8αα+CD8ab T-cells (selected by TL-tetramers) followed by in vitro differentiated (RABI27) CD4+ CTL could potentially represent a superior anti-cancer immuno therapy treatment. These new treatments (selection and expansion of TL-tetramer+CD8ab T-cells and in vitro differentiation of Treg TILs or anti-tumor naïve CD4+ T-cells to CTL could also be combined with existing immunotherapies and will greatly enhance the efficacy and prolonged duration of the anti-tumor response and surveillance."

This experiment is repeated with double-negative T-cells (CD3+, CD4−, CD8−), IFN γ, and/or aGalCer-stimulated NK T-cells in lieu of or in addition to the CD8αα+CD8+ T-cells. The same or similar results are expected.

Example 4: CD8αα CD4 T Cells Anti-Tumor Function

T Cell Isolation and Cell Sorting

Splenic CD4 T cells were purified by magnetic negative selection with the MACS CD4 T cell isolation kit according to the manufacturer's protocol (Miltenyi Biotec). Reprogrammed CD8+ ThPOK-GFP-CD4 T cells were sorted with a FACSAria (Becton Dickinson).

Immunofluorescence Staining and Flow Cytometry

Cells were pre-incubated with anti-CD16-CD32 (2.4G2; prepared 'in-house') to block binding of antibody to the Fc receptor, and then stained in cold PBS containing 0.5% (vol/vol) FBS and 0.05% (wt/vol) sodium azide with the relevant labeled antibodies and tetramers. The following antibodies were used: anti-CD8β (cl. H35-17.2, eBioscience) anti-CD4 (cl. RM4-5, BD) and anti-CD8α (cl. 53.6.7, BD).

In Vitro Stimulation of T Cells

For activation of T cells, 100,000 naïve CD8 T cells were cultured in 96-well plates in the presence of coated anti-CD3F (1.5 μg/ml, cl. 145-2C11, eBioscience), soluble anti-CD28 (0.5 μg/ml, cl. 37.51, eBioscience).

In some cases, the method further comprises contacting a population of tumor-specific CD4+ T-cells with an effective amount of anti-CD28 antibody, fragment or equivalent thereof and/or anti-CD3 antibody, fragment or equivalent thereof. In some cases, the anti-CD3 antibody, fragment or equivalent thereof is bound to a plate on which the population of tumor-specific CD4+ T-cells are plated. In further cases, the method further comprises contacting a population of tumor-specific CD4+ T-cells with an antigen, e.g., a tumor antigen. In further cases, the anti-CD28 antibody, fragment or equivalent thereof, optional antigen, and the combination comprising retinoic acid, TGF-β, and IL-27 are administered simultaneously or sequentially. In some cases, anti-CD28 antibody, fragment or equivalent thereof and, optionally, the antigen are administered once. In cases involving multiple administrations of the combination comprising retinoic acid, TGF-β, and IL-27, anti-CD28 antibody, fragment or equivalent thereof and/or anti-CD3 antibody, fragment or equivalent thereof and, optionally, the antigen are administered once, optionally concurrently or sequentially with the first administration of the combination comprising retinoic acid, TGF-β, and IL-27. In some cases, the anti-CD28 antibody, fragment or equivalent thereof is at a concentration greater than about 0.5 µg/mL, less than about 2 µg/mL, or between about 0.5 µg/mL and about 2 µg/mL, and concentration ranges in between. All the indicated concentrations are the final concentrations in solution. In some cases, anti-CD3 antibody, fragment or equivalent thereof and, optionally, the antigen is administered once. In cases involving multiple administrations of the combination comprising retinoic acid, TGF-β, and IL-27, anti-CD3 antibody, fragment or equivalent thereof is administered more than once, e.g., twice or thrice or multiple times thereafter as necessary, optionally concurrently or sequentially with the administration of the combination comprising retinoic acid, TGF-β, and IL-27. In some cases, the anti-CD3 is at a concentration of greater than about 1 µg/mL, less than about 2 µg/mL, or between about 1 µg/mL and about 2 µg/mL, and concentration ranges in between. All the indicated concentrations are the final concentrations in solution. In some cases, the combination comprises greater than about 5 ng/mL, less than about 25 ng/mL, or between about 5 ng/mL to about 25 ng/mL of Il-27; greater than, less than, or about 5 ng/mL or between about 2 ng/mL to about 10 ng/mL of TGF-β, and/or greater than about 100 nM, less than about 500 nM, or between about 100 nM to about 500 nM of retinoic acid, and concentration ranges in between.

Tumor Challenge $5 \times 10^5$ ovalbumin-expressing B16 melanoma cells were injected subcutaneously into Rag-/- mice. The same day, Rag-/- OT-II cells ($5 \times 10^5$) activated and sorted for their CD8αα expression were injected intravenously and tumor size was monitored by measurement in two dimensions with digital calipers.

Tumor Infiltrating Lymphocytes Isolation

The TILs isolation protocol has been adapted from Jonker et. al. Mouse tumors were harvested and stored in DMEM 5% FCS. Tumors were then weighed, cut into small pieces, and resuspended in DMEM (2.5 mL for 200 mg tissue) containing 20% FCS, 1 mg/mL collagenase D (Roche), and 25 µg/mL DNase I (Sigma). This was then agitated at 250 rpm for 90 minutes at 37° C. with vigorous pipetting every 20 minutes. The cell suspension was then filtered through a 40-µm cell strainer (BD Falcon) and washed in DMEM 5% FCS. Tumor-infiltrating lymphocytes (TIL) were isolated on a Percoll® (GE healthcare, Bio-science) gradient (70% and 40%) in DMEM 5% FCS from 70% to 40% interface and washed in DMEM 5% FCS. Jonker, et. al., Cancer Res 2006; 66:5443-5451

Example 5: CD8αα CD8 In Vivo Anti-Tumor Function

Naive OT-I CD8 T cells were activated with anti-CD3 and anti-CD28. After 48 h, CD8αα$^-$ or CD8αα$^+$ live activated T cells were sorted and transferred to Rag$^{-/-}$ mice bearing B16-OVA melanoma tumors. Tumor volume and survival was then assessed daily.

T Cell Isolation and Cell Sorting

Figure 26A:
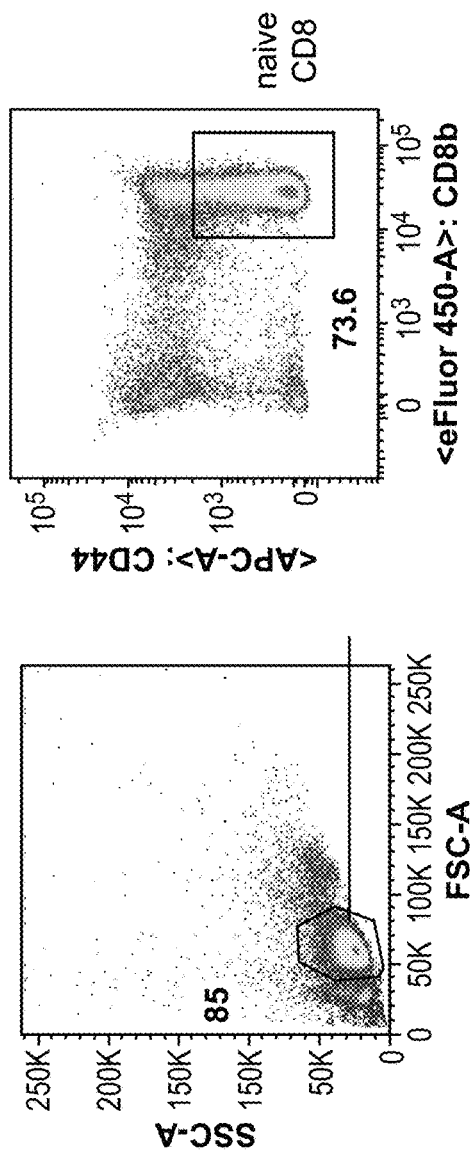
FIG. 26A shows a gating strategy for sorting of naïve CD8.

Splenic CD8 T cells were purified by magnetic negative selection with the MACS CD8α T cell isolation kit according to the manufacturer's protocol (Miltenyi Biotec). CD8β$^+$ CD44 low cells were sorted as naïve CD8 T cells with a FACSAria (Becton Dickinson) (FIG. 26A).

Immunofluorescence Staining and Flow Cytometry

Figure 26B:
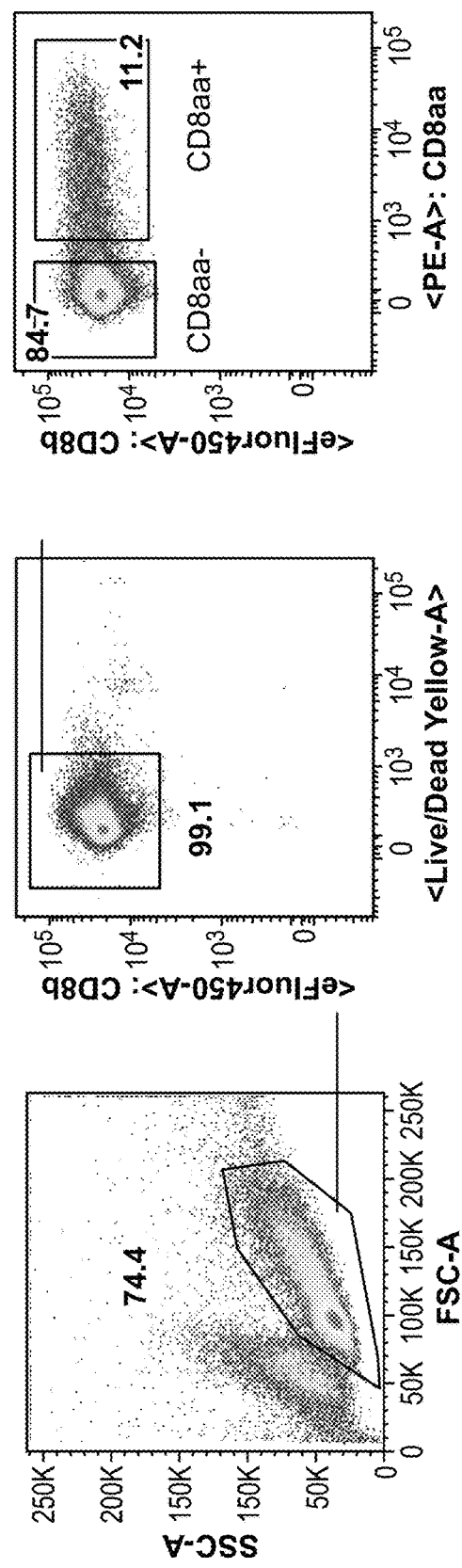
FIG. 26B shows a gating strategy for sorting of CD8αα− and CD8αα+ activated CD8+ T-cells.

Cells were pre-incubated with anti-CD16-CD32 (2.4G2; prepared 'in-house') to block binding of antibody to the Fc receptor, and then stained in cold PBS containing 0.5% (vol/vol) FBS and 0.05% (wt/vol) sodium azide with the relevant labeled antibodies and tetramers. The following antibodies were used: anti-CD8β (cl. H35-17.2) and anti-CD44 (cl. IM7) (all from eBioscience). CD8αα homodimers were specifically detected using TL-tetramer (Leishman et al., 2001). For detection of cell death, cells were stained with the Live/Dead fixable dead cell stain kit according to the manufacturer's protocol (Invitrogen) (FIG. 26B).

In Vitro Stimulation of T Cells

For activation of T cells, 100,000 naïve CD4 or CD8 T cells were cultured in 96-well plates in the presence of coated anti-CD3ε(1 µg/ml, cl. 145-2C11, eBioscience) and soluble anti-CD28 (0.5 µg/ml, cl. 37.51, eBioscience).

Tumor Challenge $1 \times 10^6$ ovalbumin-expressing B16 melanoma cells were injected subcutaneously into Rag$^{-/-}$ mice. Rag$^{-/-}$ OT-I cells ($5 \times 10^5$) activated and sorted for their CD8αα expression were injected intravenously 7 days after the injection of tumor cells, and tumor size was monitored by measurement in two dimensions with digital calipers. See Leishman, A. J., Naidenko, O. V., Attinger, A., Koning, F., Lena, C. J., Xiong, Y., Chang, H. C., Reinherz, E., Kronenberg, M., and Cheroutre, H. (2001). T cell responses modulated through interaction between CD8αalphaalpha and the nonclassical MHC class I molecule, TL. Science 294, 1936-1939.

Tumor Infiltrating Lymphocytes Isolation

This TILs isolation protocol has been adapted from Jonker et. al. Mouse tumors were harvested and stored in DMEM 5% FCS. Tumors were then weighed, cut into small pieces, and resuspended in DMEM (2.5 mL for 200 mg tissue) containing 20% FCS, 1 mg/mL collagenase D (Roche), and 25 µg/mL DNase I (Sigma). This was then agitated at 250 rpm for 90 minutes at 37° C. with vigorous pipetting every 20 minutes. The cell suspension was then filtered through a 40-µm cell strainer (BD Falcon) and washed in DMEM 5% FCS. Tumor-infiltrating lymphocytes (TILs) were isolated on a Percoll® (GE healthcare, Bio-science) gradient (70% and 40%) in DMEM 10% FCS from 70% to 40% interface and washed in DMEM 5% FCS. Jonker, et. al., Cancer Res 2006; 66:5443-5451

Example 6: CD8αα CD8 In Vitro Killing Assay

Naive OT-I CD8 T cells were activated with anti-CD3 and anti-CD28. After 48 h, CD8αα$^-$ or CD8αα$^+$ live activated T cells were sorted and their cytotoxic capacity against B16-OVA melanoma tumor cells was measured in vitro.

T Cell Isolation and Cell Sorting

Splenic CD8 T cells were purified by magnetic negative selection with the MACS CD8α+ T cell isolation kit according to the manufacturer's protocol (Miltenyi Biotec). CD8β+ CD44 low cells were sorted as naïve CD8 T cells with a FACSAria (Becton Dickinson) (FIG. 26A).

Immunofluorescence Staining and Flow Cytometry

Cells were pre-incubated with anti-CD16-CD32 (2.4G2; prepared 'in-house') to block binding of antibody to the Fc receptor, and then stained in cold PBS containing 0.5% (vol/vol) FBS and 0.05% (wt/vol) sodium azide with the relevant labeled antibodies and tetramers. The following antibodies were used: anti-CD8β (cl. H35-17.2) and anti-CD44 (cl. IM7) (all from eBioscience). CD8αα homodimers were specifically detected using TL-tetramer (Leishman et al., 2001). For detection of cell death, cells were stained with the Live/Dead fixable dead cell stain kit according to the manufacturer's protocol (Invitrogen) (FIG. 26B).

In Vitro Stimulation of T Cells

For activation of T cells, 100,000 naïve CD4 or CD8 T cells were cultured in 96-well plates in the presence of coated anti-CD3ε (1 µg/ml, cl. 145-2C11, eBioscience) and soluble anti-CD28 (0.5 µg/ml, cl. 37.51, eBioscience).

Real-Time Cytotoxicity Assay xCELLigence®

Target cells (B16 and B16-OVA) were seeded in 100 µl of complete RPMI 10% FCS medium at a density of 10,000 cells per well in 96 well E-plate xCELLigence®. Cell attachment and proliferation was monitored by measuring the electrical impedance using the Real Time Cell Aanalyser instrument xCELLigence® 24 h later, when the plateau phase was reached, T cells were added at different effector to target ratios (E:T) and impedance measurements were performed every 15 min for up to 81 h. All experiments were performed in triplicates. Changes in electrical impedance were expressed as a dimensionless cell index (AU), which derives from relative impedance changes corresponding to cellular coverage of the electrode sensors, normalized to baseline impedance values with medium only. To analyze the acquired data, the slope (Cell Index/hours) values were calculated at different time ranges. See Leishman, A. J., Naidenko, O. V., Attinger, A., Koning, F., Lena, C. J., Xiong, Y., Chang, H. C., Reinherz, E., Kronenberg, M., and Cheroutre, H. (2001). T cell responses modulated through interaction between CD8αalphaalpha and the nonclassical MHC class I molecule, TL. Science 294, 1936-1939.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

What is claimed is:

1. A method of generating a population of tumor-specific CD4+ cytotoxic T-cells comprising contacting a population of tumor-specific CD4+ T-cells with an effective amount of a combination comprising cytokines and retinoic acid thereby generating tumor-specific CD4+ cytotoxic T-cells, and wherein the cytokines consist of TGF-β, and IL-27.

2. The method of claim 1, wherein the population of tumor-specific CD4+ T-cells comprises one or more of naïve CD4+ T-cells, Th1 T-cells, Th17 T-cells, and T-regulatory cells.

3. A method of generating a population of tumor-specific CD4+ cytotoxic T-cells comprising contacting a population of tumor-specific CD4+ T-cells with an effective amount of a combination consisting of retinoic acid, TGF-β, IL-27 and an effective amount of an anti-CD3 or an anti-CD28 antibody thereby generating tumor-specific CD4+ cytotoxic T-cells.

4. The method of claim 1, further comprising contacting the population of tumor-specific CD4+ T-cells with an effective amount of IL-15.

5. The method of claim 1, wherein the IL-27 in the combination comprises between 5 ng/mL to 25 ng/mL of IL-27.

6. The method of claim 1, wherein the TGF-β in the combination comprises between 2 ng/mL to 10 ng/mL of TGF-β, optionally 5 ng/mL of TGF-β.

7. The method of claim 1, wherein the retinoic acid in the combination comprises between 100 nM to 500 nM of retinoic acid.

8. The method of claim 1, further comprising isolating the population of CD4+ cytotoxic T-cells.

* * * * *

SEQUENCE LISTING

```
<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5
```

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctcgagccca aatcttgtga caaaactcac acatgcccac cgtgcccg                48

<210> SEQ ID NO 3
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttttgggtgc tggtggtggt tggtggagtc ctggcttgct atagcttgct agtaacagtg     60
gcctttatta ttttctgggt g                                              81

<210> SEQ ID NO 4
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                              126

<210> SEQ ID NO 5
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aggagtaaga ggagcaggct cctgcacagt gactacatga acatgactcc ccgccgcccc     60
gggcccaccc gcaagcatta ccagccctat gccccaccac gcgacttcgc agcctatcgc    120
tcc                                                                 123

<210> SEQ ID NO 6
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
agagtgaagt tcagcaggag cgcagacgcc cccgcgtacc agcagggcca gaaccagctc     60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga agataagat ggcggaggcc tacagtgaga ttgggatgaa aggcgagcgc    240

```
cggaggggca aggggcacga tggcctttac cagggtctca gtacagccac caaggacacc    300
tacgacgccc ttcacatgca ggccctgccc cctcgctaa                           339
```

<210> SEQ ID NO 7
<211> LENGTH: 362
<212> TYPE: PRT
<213> ORGANISM: Mus musculus

<400> SEQUENCE: 7

| | | | | | | | | | | | | | | | |
|---|---|---|---|---|---|---|---|---|---|---|---|---|---|---|---|
| Met | Gly | Ala | Met | Ala | Pro | Arg | Thr | Leu | Leu | Leu | Leu | Ala | Ala | | |
| 1 | | | | 5 | | | | | 10 | | | | | 15 | |

Leu Ala Pro Thr Gln Thr Arg Ala Gly Pro His Ser Met Arg Tyr Phe
                20                  25                  30

Glu Thr Ala Val Ser Arg Pro Gly Leu Glu Glu Pro Arg Tyr Ile Ser
            35                  40                  45

Val Gly Tyr Val Asp Asn Lys Glu Phe Val Arg Phe Asp Ser Asp Ala
    50                  55                  60

Glu Asn Pro Arg Tyr Glu Pro Arg Ala Pro Trp Met Glu Gln Glu Gly
65                  70                  75                  80

Pro Glu Tyr Trp Glu Arg Glu Thr Gln Lys Ala Lys Gly Gln Glu Gln
                85                  90                  95

Trp Phe Arg Val Ser Leu Arg Asn Leu Leu Gly Tyr Tyr Asn Gln Ser
            100                 105                 110

Ala Gly Gly Ser His Thr Leu Gln Gln Met Ser Gly Cys Asp Leu Gly
    115                 120                 125

Ser Asp Trp Arg Leu Leu Arg Gly Tyr Leu Gln Phe Ala Tyr Glu Gly
130                 135                 140

Arg Asp Tyr Ile Ala Leu Asn Glu Asp Leu Lys Thr Trp Thr Ala Ala
145                 150                 155                 160

Asp Met Ala Ala Gln Ile Thr Arg Arg Lys Trp Glu Gln Ser Gly Ala
                165                 170                 175

Ala Glu His Tyr Lys Ala Tyr Leu Glu Gly Glu Cys Val Glu Trp Leu
            180                 185                 190

His Arg Tyr Leu Lys Asn Gly Asn Ala Thr Leu Leu Arg Thr Asp Ser
    195                 200                 205

Pro Lys Ala His Val Thr His His Pro Arg Ser Lys Gly Glu Val Thr
210                 215                 220

Leu Arg Cys Trp Ala Leu Gly Phe Tyr Pro Ala Asp Ile Thr Leu Thr
225                 230                 235                 240

Trp Gln Leu Asn Gly Glu Glu Leu Thr Gln Asp Met Glu Leu Val Glu
                245                 250                 255

Thr Arg Pro Ala Gly Asp Gly Thr Phe Gln Lys Trp Ala Ser Val Val
            260                 265                 270

Val Pro Leu Gly Lys Glu Gln Asn Tyr Thr Cys Arg Val Tyr His Glu
    275                 280                 285

Gly Leu Pro Glu Pro Leu Thr Leu Arg Trp Glu Pro Pro Ser Thr
290                 295                 300

Asp Ser Tyr Met Val Ile Val Ala Val Leu Gly Val Leu Gly Ala Met
305                 310                 315                 320

Ala Ile Ile Gly Ala Val Val Ala Phe Val Met Lys Arg Arg Arg Asn
                325                 330                 335

Thr Gly Gly Lys Gly Gly Asp Tyr Ala Leu Ala Pro Gly Ser Gln Ser
            340                 345                 350

```
Ser Glu Met Ser Leu Arg Asp Cys Lys Ala
        355                 360

<210> SEQ ID NO 8
<211> LENGTH: 33
<212> TYPE: PRT
<213> ORGANISM: Mus musculus

<400> SEQUENCE: 8

Gly Asn Gly Asp Asp Asn Thr Ala Ala Tyr Gln Asn Glu Arg Glu His
1               5                   10                  15

Leu Ser Leu Thr Leu Gly Leu Asn Leu Arg His Ser Gly Trp Lys Leu
            20                  25                  30

Gly

<210> SEQ ID NO 9
<211> LENGTH: 384
<212> TYPE: PRT
<213> ORGANISM: Mus musculus

<400> SEQUENCE: 9

Met Arg Met Gly Thr Met Val Pro Gly Thr Leu Leu Ile Leu Leu Ala
1               5                   10                  15

Ala Ser Gln Gly Gln Thr Gln Thr Cys Pro Gly Ser His Ser Leu Arg
            20                  25                  30

Tyr Phe Tyr Thr Ala Leu Ser Arg Pro Ala Ile Ser Glu Pro Trp Tyr
        35                  40                  45

Ile Ala Val Gly Tyr Leu Asp Asp Thr Gln Phe Val Arg Phe Asn Ser
50                  55                  60

Ser Gly Glu Thr Ala Thr Tyr Lys Leu Ser Ala Pro Trp Val Glu Gln
65                  70                  75                  80

Glu Gly Pro Glu Tyr Trp Ala Arg Glu Thr Glu Ile Val Thr Ser Asn
                85                  90                  95

Ala Gln Phe Phe Arg Glu Asn Leu Gln Thr Met Leu Asp Tyr Tyr Asn
            100                 105                 110

Leu Ser Gln Asn Gly Ser His Thr Ile Gln Val Met Tyr Gly Cys Glu
        115                 120                 125

Val Glu Phe Phe Gly Ser Leu Phe Arg Ala Tyr Glu Gln His Gly Tyr
130                 135                 140

Asp Gly Arg Asp Tyr Ile Ala Leu Asn Glu Asp Leu Lys Thr Trp Thr
145                 150                 155                 160

Ala Ala Asp Thr Ala Ala Glu Ile Thr Arg Ser Lys Trp Glu Gln Ala
                165                 170                 175

Gly Tyr Thr Glu Leu Arg Arg Thr Tyr Leu Glu Gly Pro Cys Lys Asp
            180                 185                 190

Ser Leu Leu Arg Tyr Leu Glu Asn Arg Lys Lys Thr Gln Glu Cys Thr
        195                 200                 205

Asp Pro Pro Lys Thr His Val Thr His His Pro Arg Pro Glu Gly Tyr
    210                 215                 220

Val Thr Leu Arg Cys Trp Ala Leu Arg Phe Tyr Pro Ala Asp Ile Thr
225                 230                 235                 240

Leu Thr Trp Gln Leu Asn Gly Glu Glu Leu Ile Gln Asp Thr Glu Leu
                245                 250                 255

Val Glu Thr Arg Pro Ala Gly Asp Gly Thr Phe Gln Lys Trp Ala Ala
            260                 265                 270

Val Val Val Pro Leu Gly Lys Glu Gln Lys Tyr Thr Cys His Val Tyr
```

```
                        275                 280                 285
His Glu Gly Leu Pro Glu Pro Leu Thr Leu Arg Trp Glu Pro Pro Gln
            290                 295                 300

Thr Ser Met Pro Asn Arg Thr Thr Val Arg Ala Leu Leu Gly Ala Met
305                 310                 315                 320

Ile Ile Leu Gly Phe Met Ser Gly Ser Val Met Met Trp Met Arg Lys
                325                 330                 335

Asn Asn Gly Gly Asn Gly Asp Asp Asn Thr Ala Ala Tyr Gln Asn Glu
            340                 345                 350

Arg Glu His Leu Ser Leu Ser Pro Arg Ala Glu Ser Glu Ala Leu Gly
                355                 360                 365

Val Glu Ala Gly Met Lys Asp Leu Pro Ser Ala Pro Pro Leu Val Ser
            370                 375                 380

<210> SEQ ID NO 10
<211> LENGTH: 384
<212> TYPE: PRT
<213> ORGANISM: Mus musculus

<400> SEQUENCE: 10

Met Arg Met Gly Thr Pro Val Pro Gly Thr Leu Leu Ile Leu Leu Ala
1               5                   10                  15

Ala Ser Gln Gly Gln Thr Gln Thr Cys Pro Gly Ser His Ser Leu Arg
            20                  25                  30

Tyr Phe Tyr Thr Ala Leu Ser Arg Pro Ala Ile Ser Glu Pro Trp Tyr
                35                  40                  45

Ile Ala Val Gly Tyr Leu Asp Asp Thr Gln Phe Val Arg Phe Asn Ser
        50                  55                  60

Ser Gly Glu Thr Ala Thr Tyr Lys Leu Ser Ala Pro Trp Val Glu Gln
65                  70                  75                  80

Glu Gly Pro Glu Tyr Trp Ala Arg Glu Thr Glu Ile Val Thr Ser Asn
                85                  90                  95

Ala Gln Phe Phe Arg Glu Asn Leu Gln Thr Met Leu Asp Tyr Tyr Asn
            100                 105                 110

Leu Ser Gln Asn Gly Ser His Thr Ile Gln Val Met Tyr Gly Cys Glu
        115                 120                 125

Val Glu Phe Phe Gly Ser Leu Phe Arg Ala Tyr Glu Gln His Gly Tyr
    130                 135                 140

Asp Gly Pro Asp Tyr Ile Ala Leu Asn Glu Asp Leu Lys Thr Trp Thr
145                 150                 155                 160

Ala Ala Asp Thr Ala Ala Glu Ile Thr Arg Ser Lys Trp Glu Gln Ala
                165                 170                 175

Gly Tyr Thr Glu Leu Arg Arg Thr Tyr Leu Glu Gly Pro Cys Lys Asp
            180                 185                 190

Ser Leu Leu Arg Tyr Leu Glu Asn Arg Lys Lys Thr Gln Glu Cys Thr
        195                 200                 205

Asp Pro Pro Lys Thr His Val Thr His His Pro Arg Pro Glu Gly Tyr
    210                 215                 220

Val Thr Leu Arg Cys Trp Ala Leu Arg Phe Tyr Pro Ala Asp Ile Thr
225                 230                 235                 240

Leu Thr Trp Gln Leu Asn Gly Glu Glu Leu Ile Gln Asp Thr Glu Leu
                245                 250                 255

Val Glu Thr Arg Pro Ala Gly Asp Gly Thr Phe Gln Lys Trp Ala Ala
            260                 265                 270
```

```
Val Val Val Pro Leu Gly Lys Glu Gln Lys Tyr Thr Cys His Val Tyr
            275                 280                 285

His Glu Gly Leu Pro Glu Pro Leu Thr Leu Arg Trp Glu Pro Pro Gln
290                 295                 300

Thr Ser Met Pro Asn Arg Thr Thr Val Arg Ala Leu Leu Gly Ala Met
305                 310                 315                 320

Ile Ile Leu Gly Phe Met Ser Gly Ser Val Met Met Trp Met Arg Lys
                325                 330                 335

Asn Asn Gly Gly Asn Gly Asp Asp Asn Thr Ala Ala Tyr Gln Asn Glu
            340                 345                 350

Arg Glu His Leu Ser Leu Asp Pro Arg Ala Glu Ser Glu Ala Leu Gly
            355                 360                 365

Val Glu Ala Gly Met Lys Asp Leu Pro Ser Ala Pro Pro Leu Val Ser
            370                 375                 380

<210> SEQ ID NO 11
<211> LENGTH: 365
<212> TYPE: PRT
<213> ORGANISM: Homo sapiens

<400> SEQUENCE: 11

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270
```

```
Val Pro Ser Gly Gln Glu Gln Arg Tyr Thr Cys His Val Gln His Glu
        275                 280                 285
Gly Leu Pro Lys Pro Leu Thr Leu Arg Trp Glu Pro Ser Ser Gln Pro
        290                 295                 300
Thr Ile Pro Ile Val Gly Ile Ile Ala Gly Leu Val Leu Phe Gly Ala
305                 310                 315                 320
Val Ile Thr Gly Ala Val Val Ala Ala Val Met Trp Arg Arg Lys Ser
                325                 330                 335
Ser Asp Arg Lys Gly Gly Ser Tyr Ser Gln Ala Ala Ser Ser Asp Ser
                340                 345                 350
Ala Gln Gly Ser Asp Val Ser Leu Thr Ala Cys Lys Val
        355                 360                 365

<210> SEQ ID NO 12
<211> LENGTH: 166
<212> TYPE: PRT
<213> ORGANISM: Homo sapiens

<400> SEQUENCE: 12

Phe Phe Thr Ser Val Ser Arg Pro Gly Arg Gly Glu Pro Arg Phe Ile
1               5                   10                  15
Ala Val Gly Tyr Val Asp Asp Thr Gln Phe Val Arg Phe Asp Ser Asp
                20                  25                  30
Ala Ala Ser Gln Arg Met Glu Pro Arg Ala Pro Trp Ile Glu Gln Glu
            35                  40                  45
Gly Pro Glu Tyr Trp Asp Gly Glu Thr Arg Lys Val Lys Ala His Ser
        50                  55                  60
Gln Thr His Arg Val Asp Leu Gly Thr Leu Arg Gly Tyr Tyr Asn Gln
65                  70                  75                  80
Ser Glu Ala Gly Ser His Thr Val Gln Arg Met Cys Gly Cys Asp Val
                85                  90                  95
Gly Ser Asp Trp Arg Phe Leu Arg Gly Tyr His Gln Tyr Ala Tyr Asp
                100                 105                 110
Gly Lys Asp Tyr Ile Ala Leu Lys Glu Asp Leu Arg Ser Trp Thr Ala
            115                 120                 125
Ala Asp Met Ala Ala Gln Thr Thr Lys His Lys Trp Glu Ala Ala His
        130                 135                 140
Val Ala Glu Gln Leu Arg Ala Tyr Leu Glu Gly Thr Cys Val Glu Trp
145                 150                 155                 160
Leu Arg Arg Tyr Leu Glu
                165
```